United States Patent
Lee et al.

(10) Patent No.: US 11,091,516 B2
(45) Date of Patent: Aug. 17, 2021

(54) SYNTHETIC BINDER OF BREAST CANCER STEM CELLS

(71) Applicant: Board of Regents, The University of Texas System, Austin, TX (US)

(72) Inventors: Jiyong Lee, Plano, TX (US); Luxi Chen, Allen, TX (US); Chao Long, Richardson, TX (US); Zhenpeng Qin, Allen, TX (US); Jonghae Youn, Plano, TX (US); Peiyuan Kang, Arlington, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 16/739,516

(22) Filed: Jan. 10, 2020

(65) Prior Publication Data
US 2020/0231627 A1 Jul. 23, 2020

Related U.S. Application Data

(60) Provisional application No. 62/791,531, filed on Jan. 11, 2019.

(51) Int. Cl.
| | |
|---|---|
| C07K 7/06 | (2006.01) |
| A61K 47/69 | (2017.01) |
| G01N 33/50 | (2006.01) |
| A61K 38/00 | (2006.01) |

(52) U.S. Cl.
CPC ............ *C07K 7/06* (2013.01); *A61K 47/6925* (2017.08); *G01N 33/5073* (2013.01); *A61K 38/00* (2013.01)

(58) Field of Classification Search
None
See application file for complete search history.

(56) References Cited

PUBLICATIONS

Park, Hye-Yeon et al; "Screening of peptides bound to breast cancer stem cell specific surface marker cd44 by phage display." Mol. Biotechnol. (2012) 51 p. 212-220.*
Chen, Luxi et al; "A synthetic binder of breast cancer stem cells." Chem. Eur. J. (2018) 24, p. 3694-3698.*
Long, Chao; "IDentification of ligands selectively targeting breast cancer stem cells via combinatorial chemical library screening." PhD thesis, Aug. 2018, University of Texas at Dallas.*
P. G. Alluri, M. M. Reddy, K. Bachhawat-Sikder, H. J. Olivos, T. Kodadek, "Isolation of Protein Ligands from Large Peptoid Libraries," *Journal of the American Chemical Society* 2003, 125, 13995-4004.
Chen, L.; Long, C.; Tran, K. A. M.; Lee, J., "A Synthetic Binder of Breast Cancer Stem Cells," *Chem. Eur. J.* 2018, 24, 3694-3698.
K. S. Lam, M. Lebl, V. Krchnak, "The "One-Bead-One-Compound" Combinatorial Library Method," *Chemical reviews* 1997, 97, 411-448.
J. Lee, M. M. Reddy, T. Kodadek, "Discovery of an Orexin Receptor Positive Potentiator," *Chemical science* 2010, 1, 48-54.
J. M. Matharage, J. D. Minna, R. A. Brekken, D. G. Udugamasooriya, "Unbiased Selection of Peptide-Peptoid Hybrids Specific for Lung Cancer Compared to Normal Lung Epithelial Cells," *ACS Chem Biol* 2015, 10, 2891-2899.
D. G. Udugamasooriya, S. P. Dineen, R. A. Brekken, T. Kodadek, "A peptoid "antibody surrogate" that antagonizes VEGF receptor 2 activity," *Journal of the American Chemical Society* 2008, 130, 5744-5752.
N. Yao, W. Xiao, X. Wang, J. Marik, S. H. Park, Y. Takada, K. S. Lam, "Discovery of targeting ligands for breast cancer cells using the one-bead one-compound combinatorial method," *J Med Chem* 2009, 52, 126-133.

* cited by examiner

*Primary Examiner* — Fred H Reynolds
(74) *Attorney, Agent, or Firm* — Parker Highlander PLLC

(57) ABSTRACT

The present disclosure provides a for peptoid compounds that bind selective to cancer stem cells (CSCs), particularly those associated with breast cancer. Conjugates of the peptoids to detactable labels and therapeutic agent are contemplated as are methods of diagnosing and treating breast cancer.

24 Claims, 25 Drawing Sheets
(22 of 25 Drawing Sheet(s) Filed in Color)

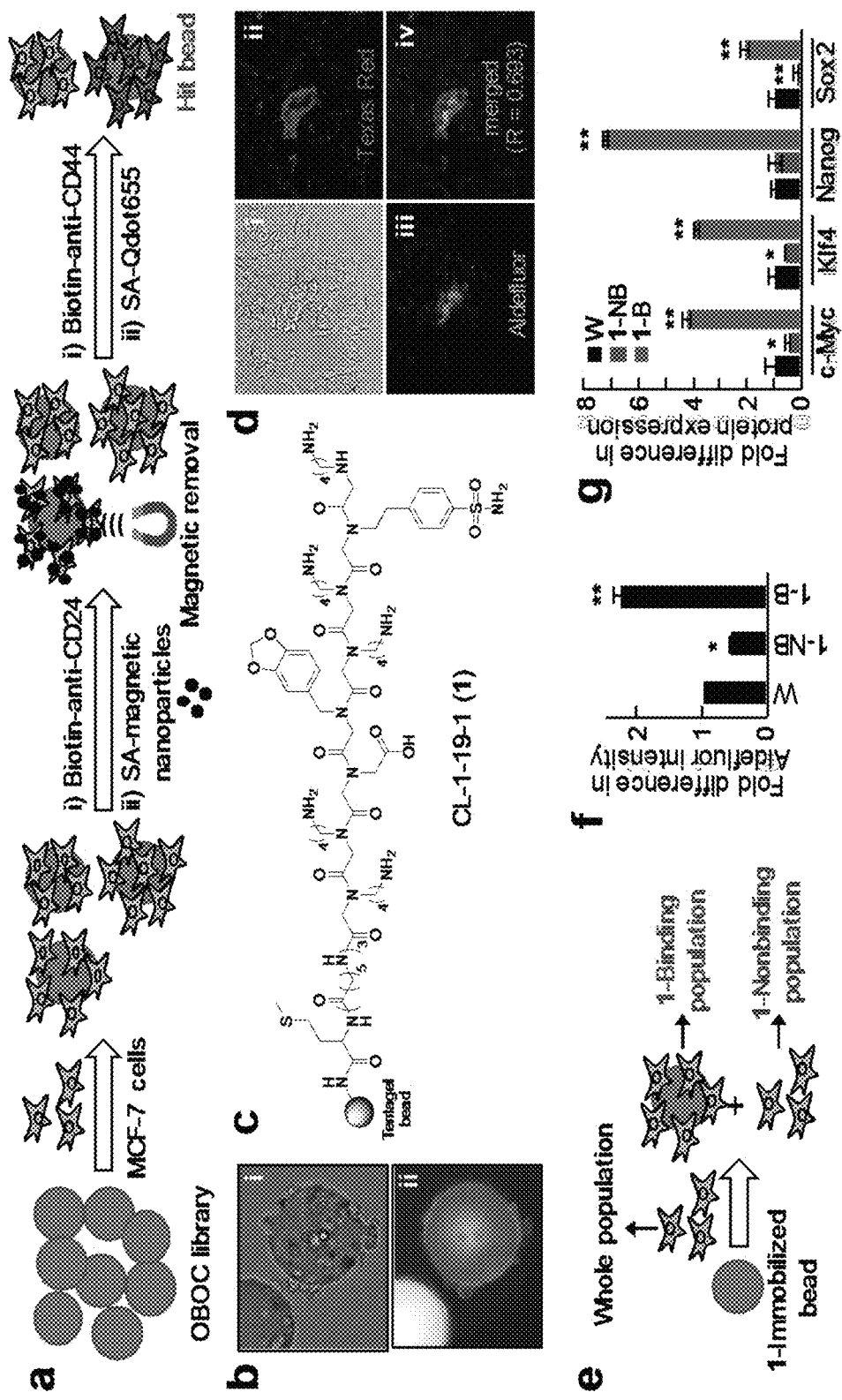
FIGS. 1A-G

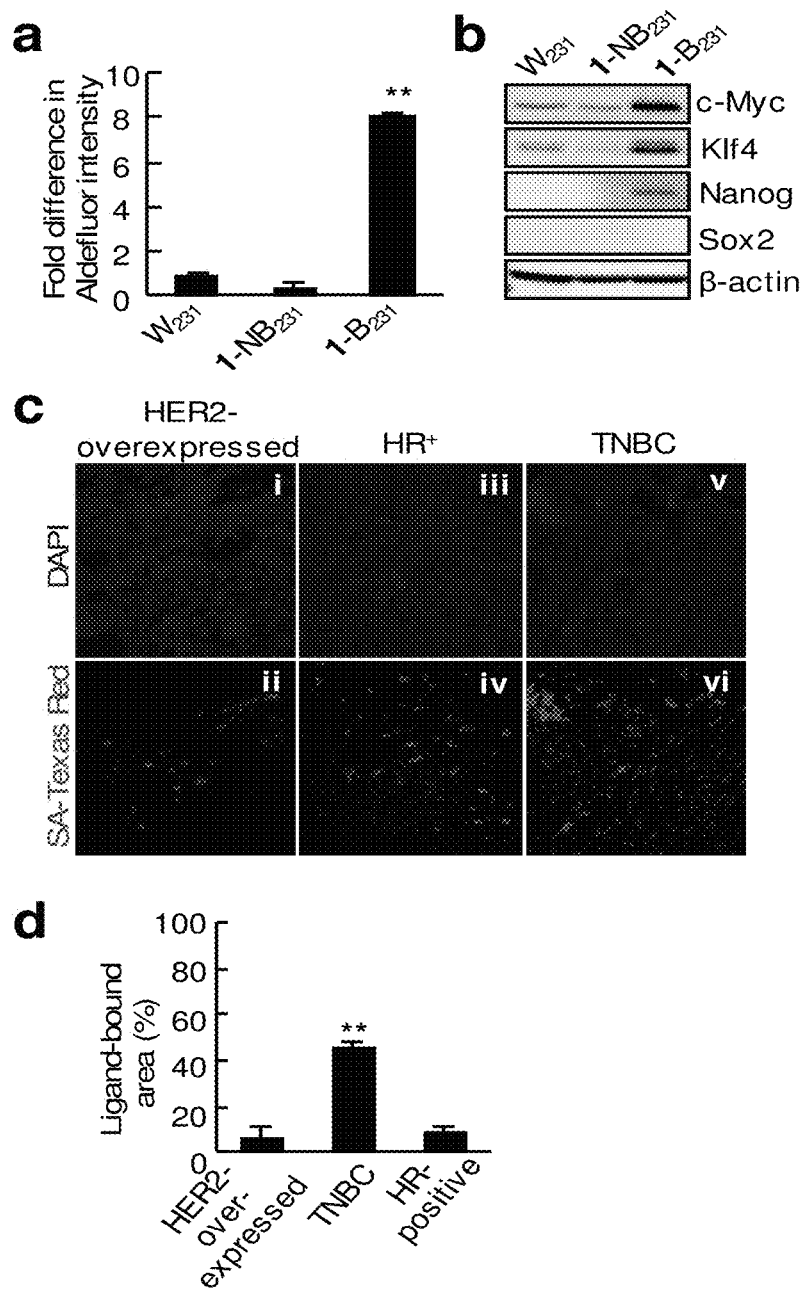
FIGS. 2A-D

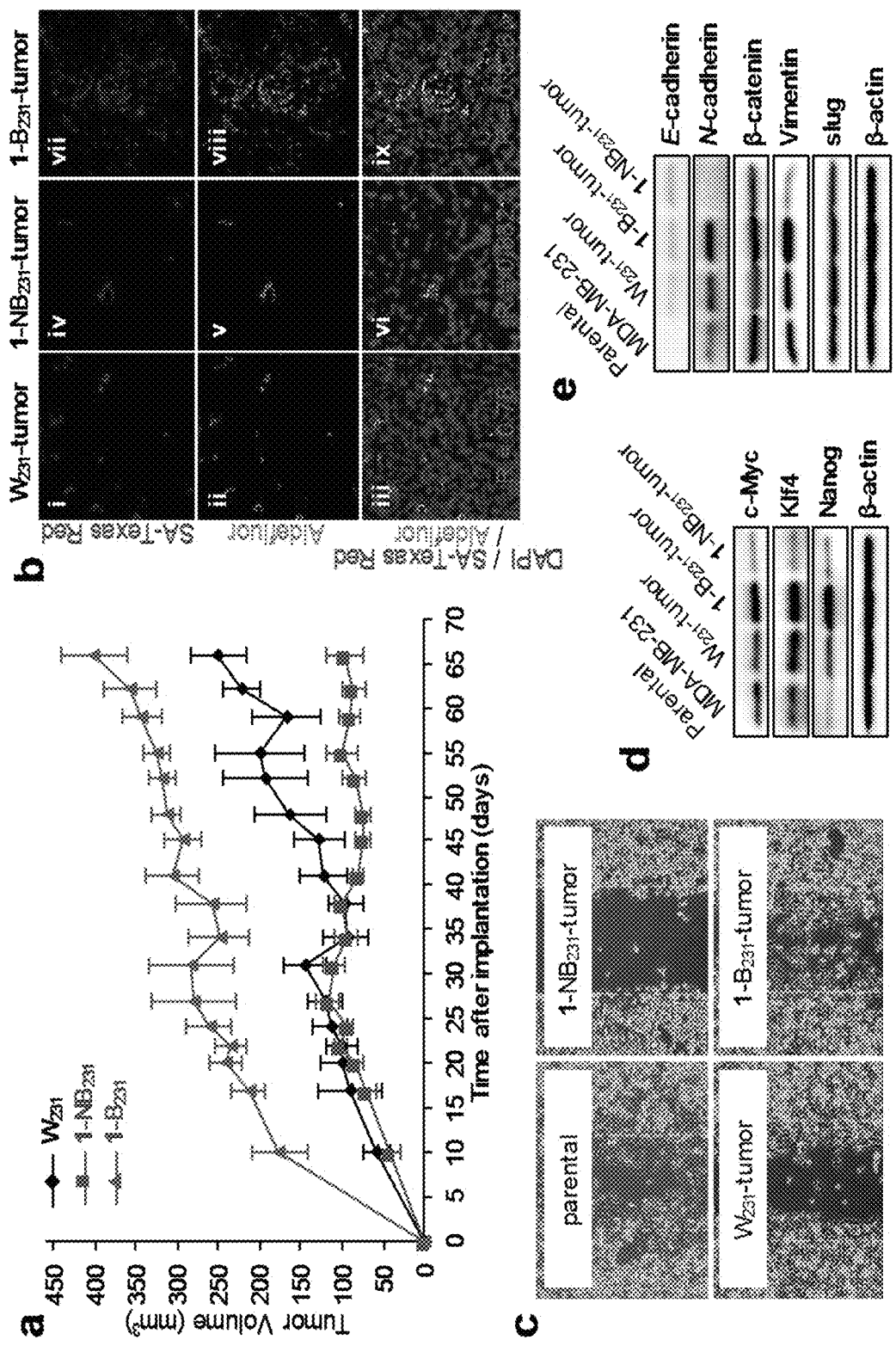
FIGS. 3A-E

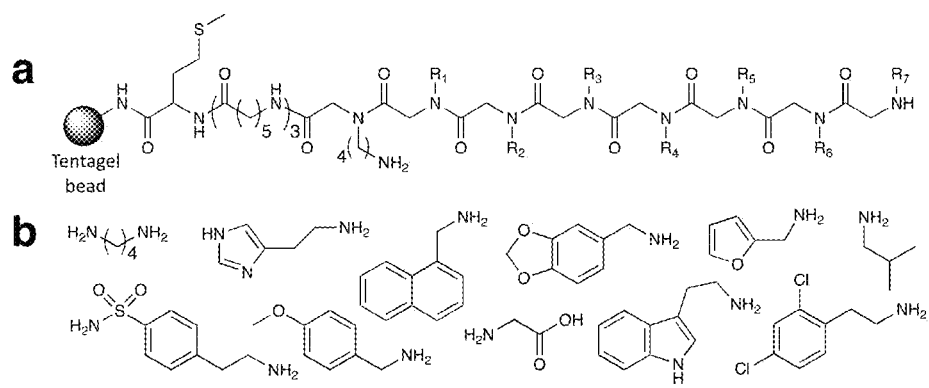
11 different amines used. Theoretical diversity of OBOC library = $11^7$ =19,487,171
FIGS. 4A-B
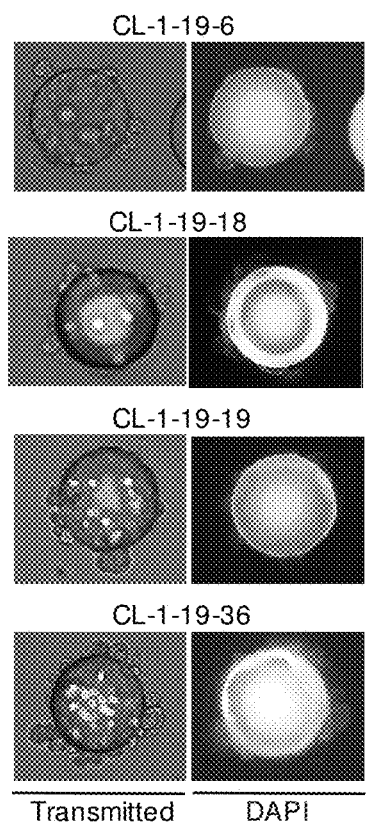
FIG. 5 a
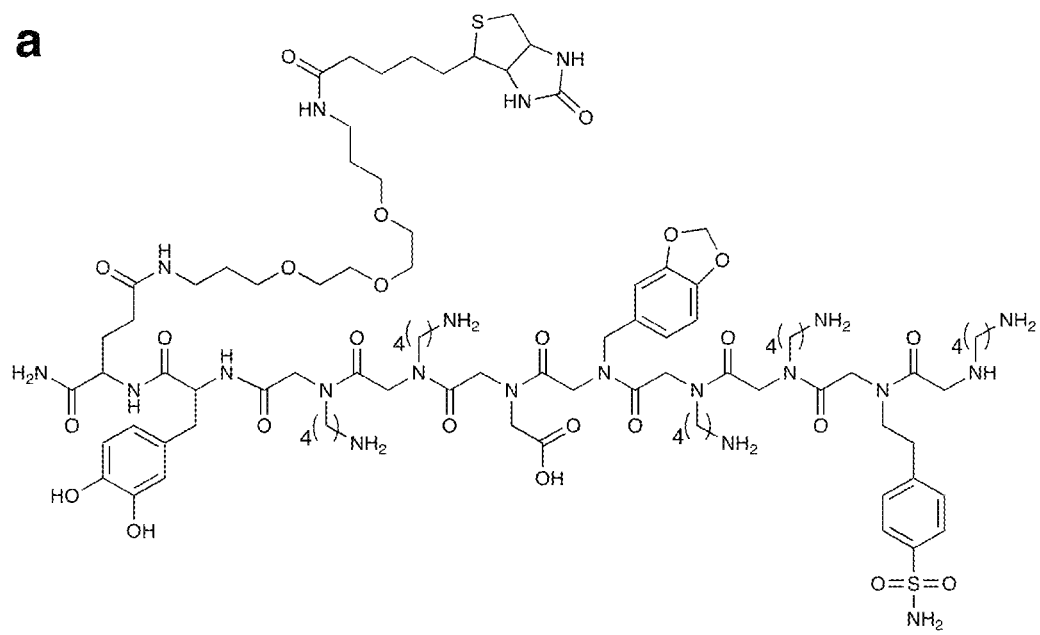
b
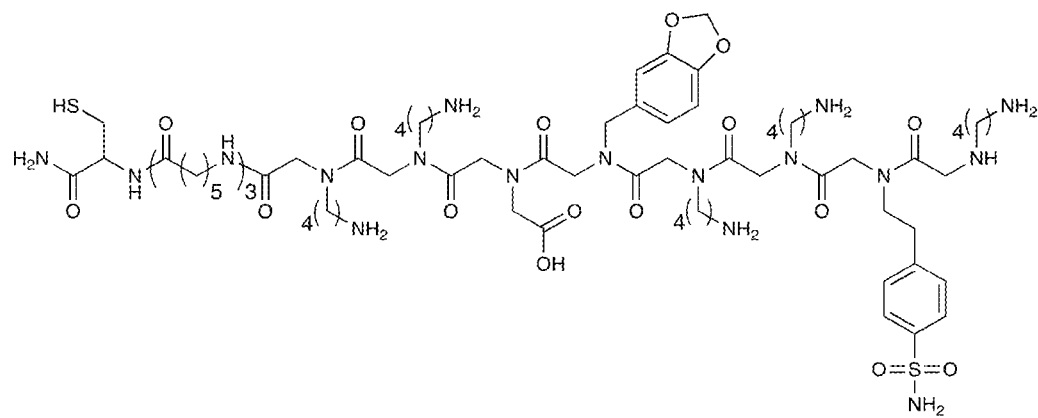
FIGS. 8A-B

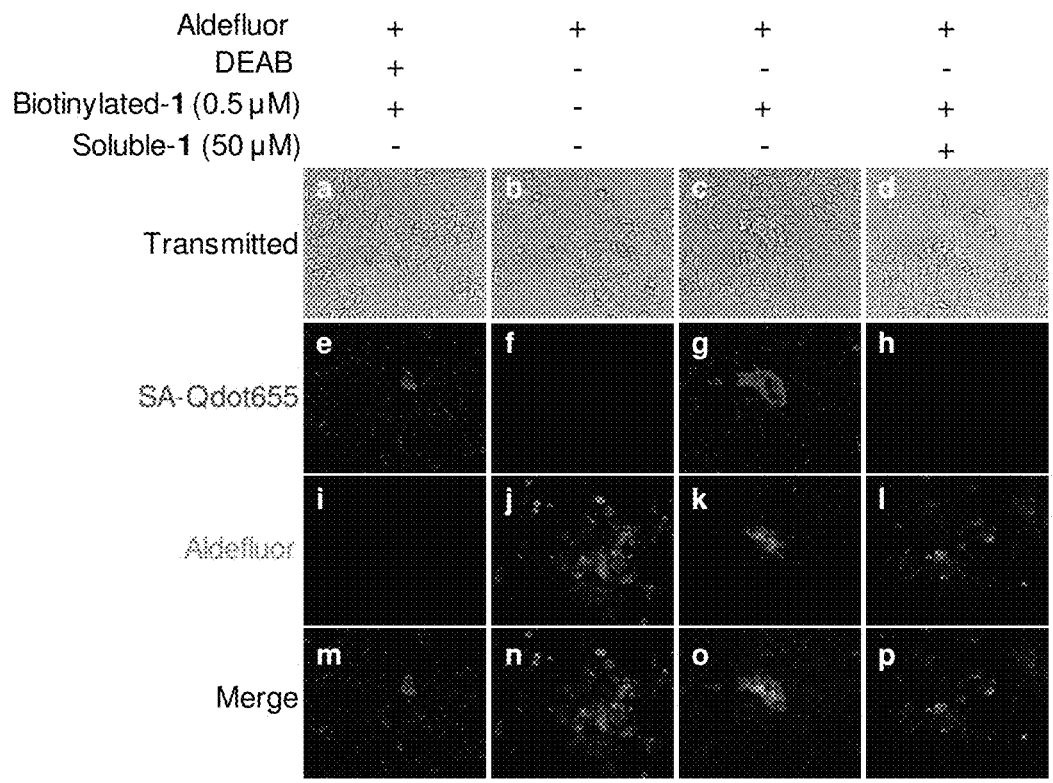
FIG. 9
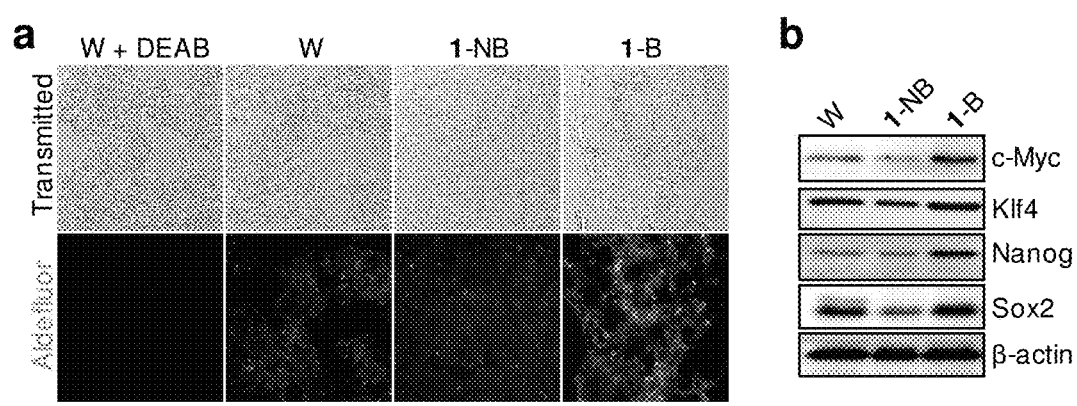
FIGS. 10A-B

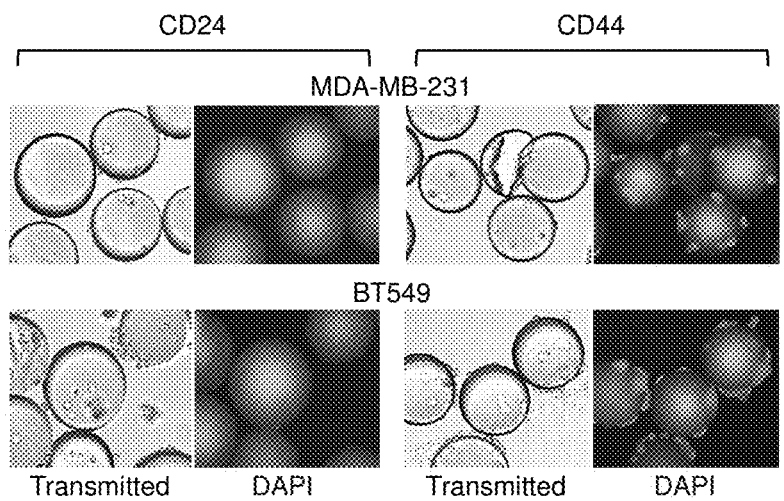
FIG. 11
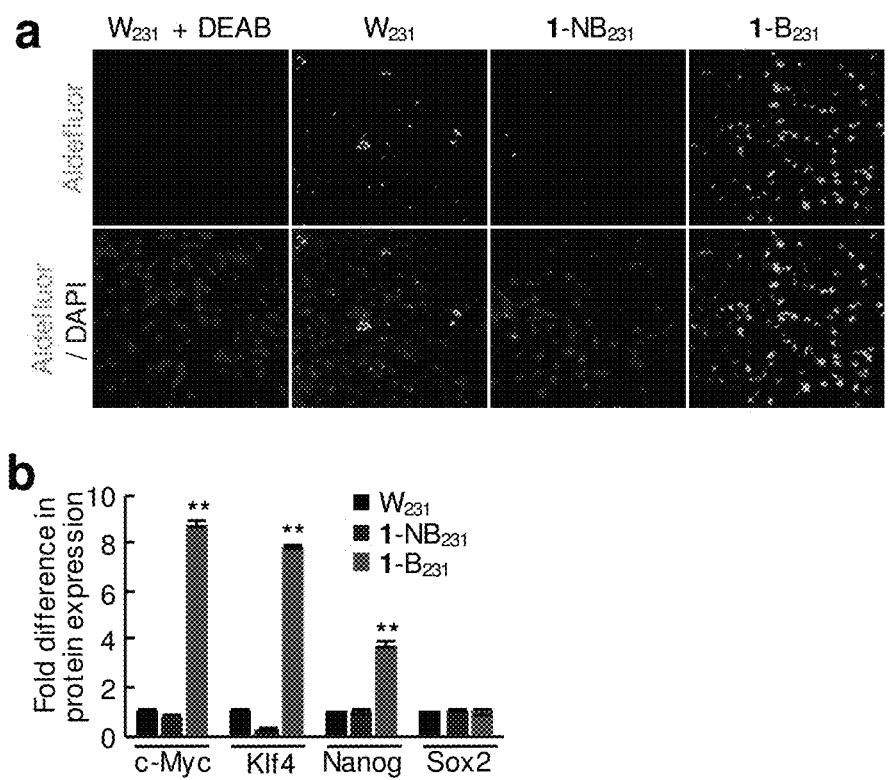
FIGS. 12A-B

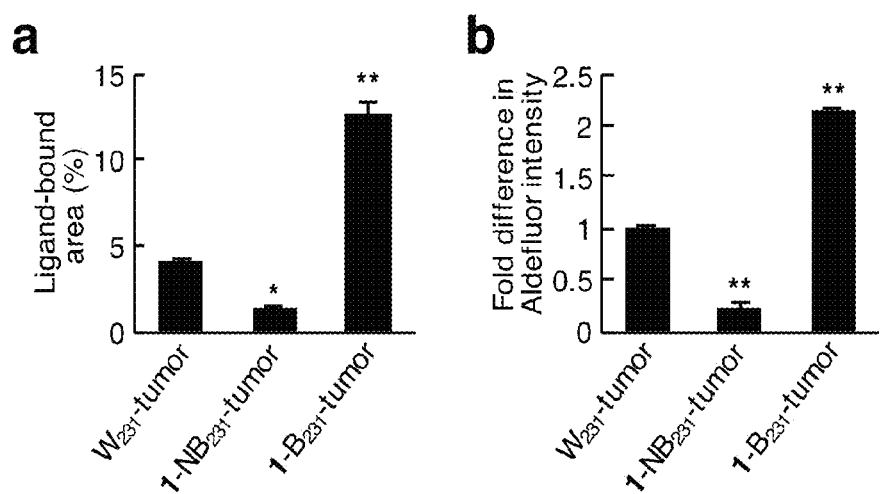
FIGS. 13A-B
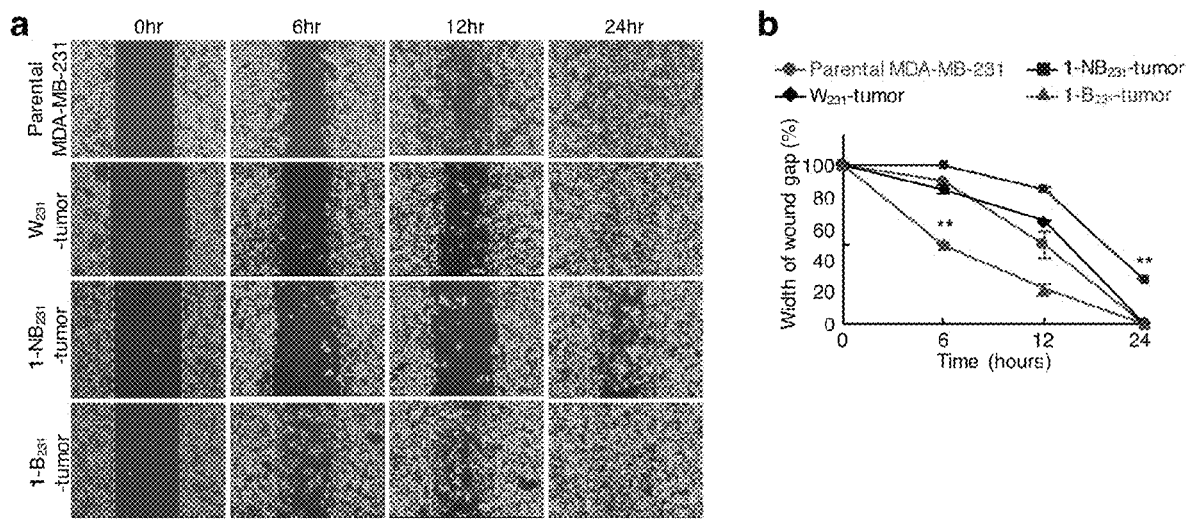
FIGS. 14A-B

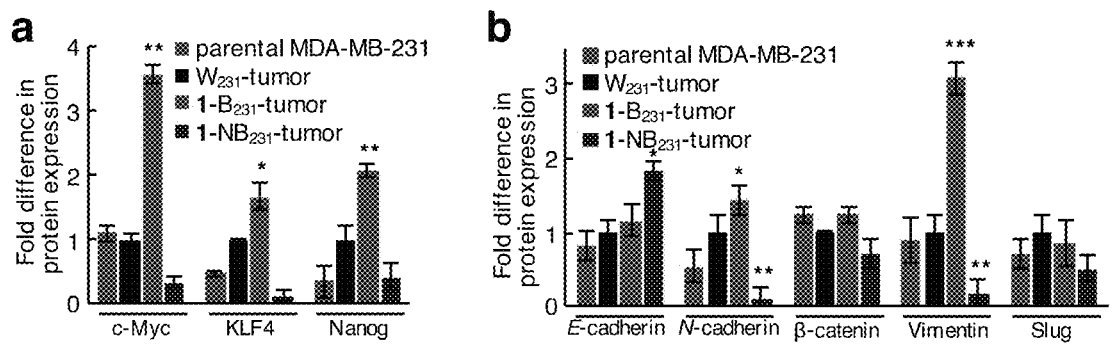
FIGS. 15A-B
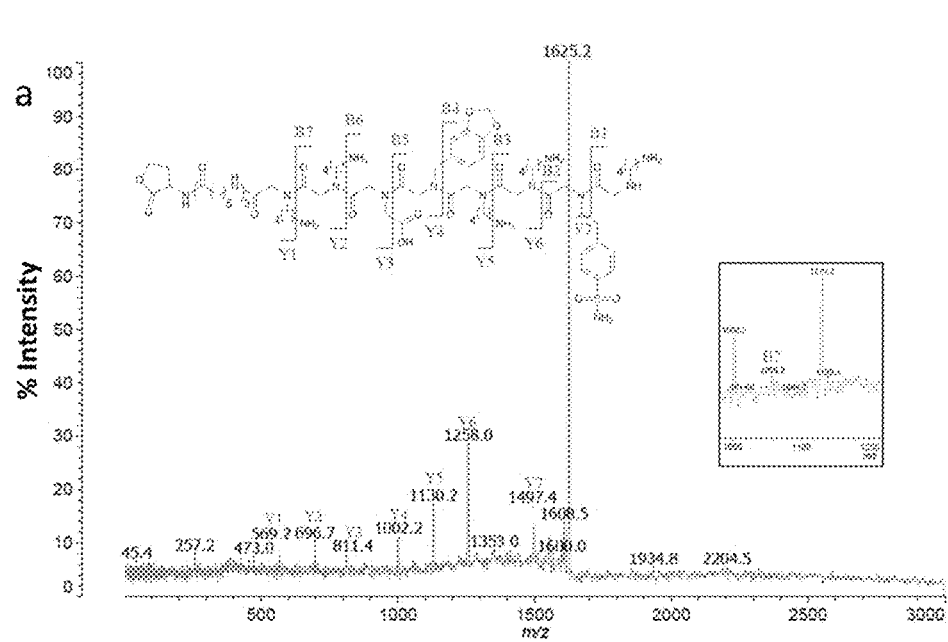
FIG. 16A

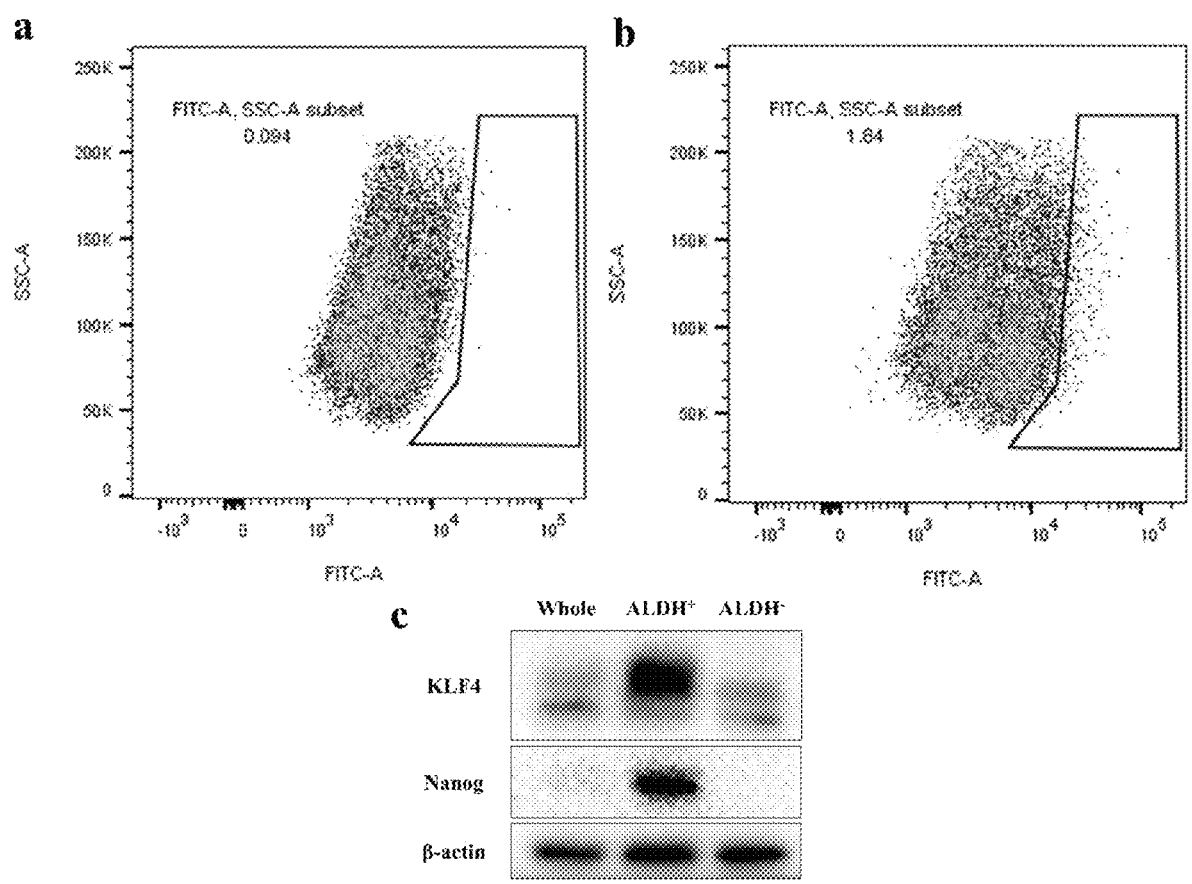
FIGS. 25A-C

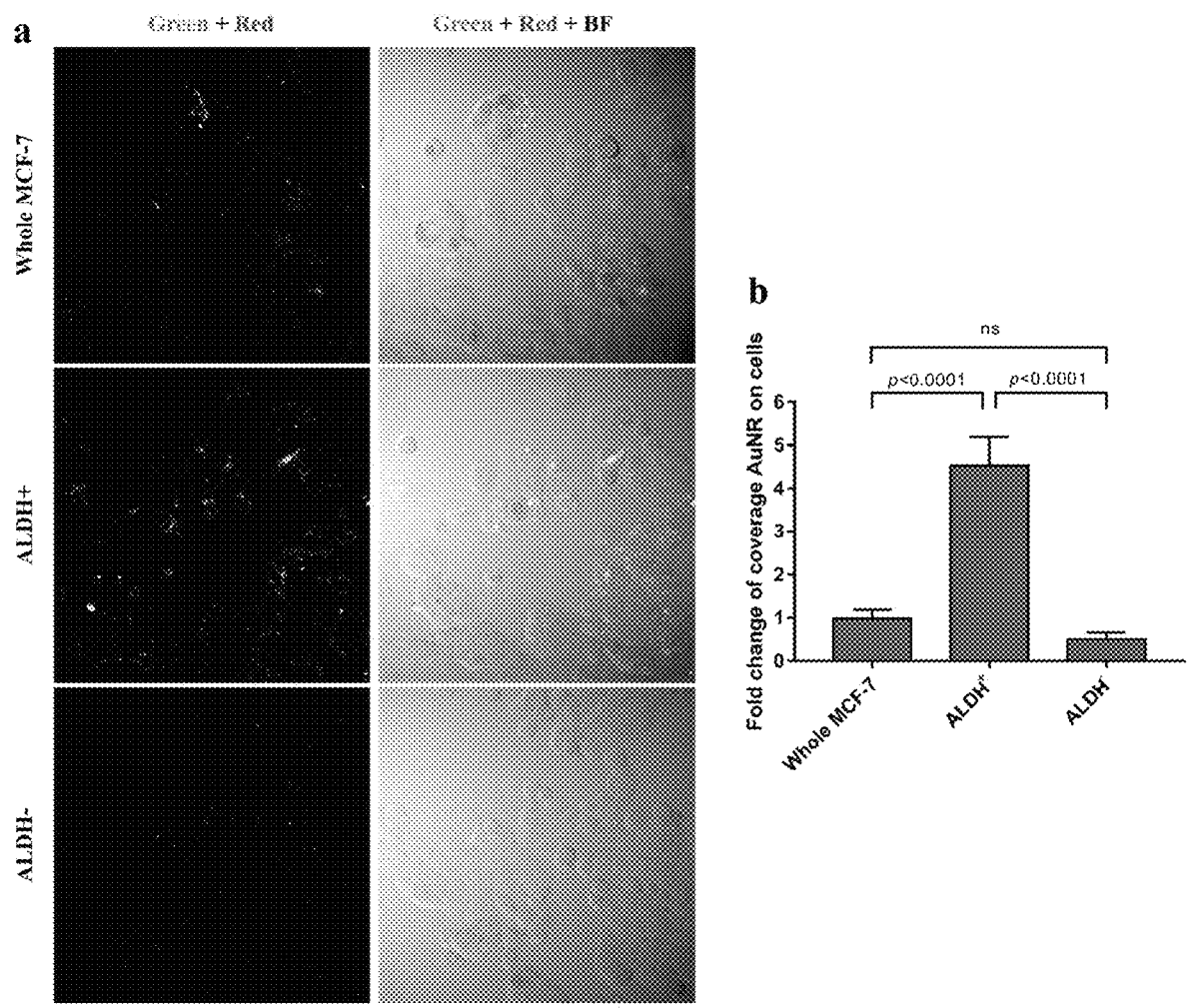
FIGS. 26A-B

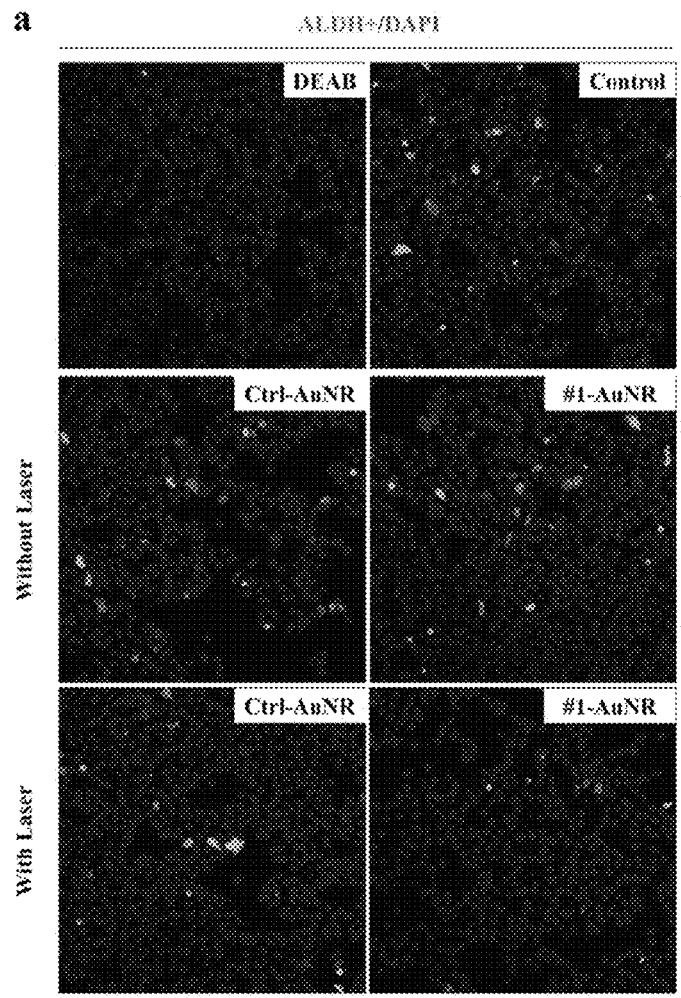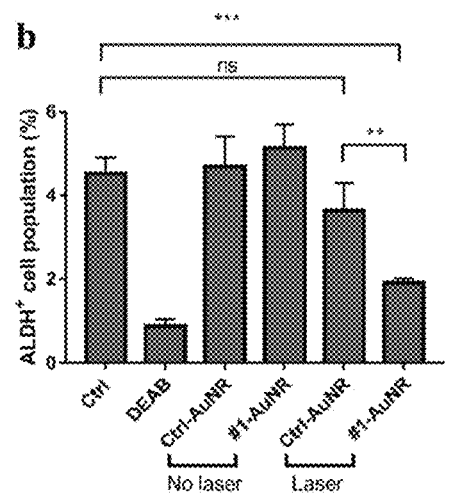
FIGS. 27A-B

SYNTHETIC BINDER OF BREAST CANCER STEM CELLS

This application claims benefit of priority to U.S. Provisional Application Ser. No. 62/791,531, filed Jan. 11, 2019, the entire contents of which are hereby incorporated by reference.

BACKGROUND

Field

The present disclosure relates generally to the fields of oncology, molecular biology, chemistry and medicine. More particularly, the disclosure relates to use of cancer stem cell binding ligands and their use to diagnose and treat cancers such as breast cancer.

Description of Related Art

The initial treatment for breast cancer is usually effective in approximately 90% of breast cancer patients resulting in a clinical remission (Gonzalez-Angulo et al., 2007). However, breast cancer survivors still have a high risk of tumor recurrence after about 5 years of the initial treatment (Brewster et al., 2008). Recurrent cancers are typically resistant to conventional therapies resulting in poor patient survival rates. A recent model for the development of recurrent cancer involves self-renewing malignant progenitors known as cancer stem cells (CSCs) that possess phenotypic heterogeneity from the bulk cancer cell populations (Dick, 2008; Clevers, 2011; Reya et al., 2001; Jordan et al., 2006). The CSC model hypothesizes that cancers are hierarchically organized and are maintained by CSCs that exist as a small population within the tumor. Moreover, CSCs are resistant to the contemporary anti-cancer therapies, and hence become a root of tumor recurrence. Therefore, novel therapeutic agents targeting CSCs hold a great promise in eradicating breast cancer without tumor recurrence. However, as CSCs exist as a small population, identification of CSCs in tumor poses a great challenge to developing CSC-targeting therapeutics. Limited numbers of cell-surface and intracellular markers are currently available to identify CSCs (Pattabiraman and Weinberg, 2014). For breast cancer, cells with a $CD24^-/CD44^+$ phenotype have been known to represent a breast CSC population (Al-Hajj et al., 2003). However, as the combination of multiple antibodies for these surface markers is necessary to detect CSC, application of these markers for in vivo studies are greatly challenged. Another issue with antibody-based detection agents is the inherent instability of antibody due to its proteinaceous nature. Therefore, there is great interest in developing a novel synthetic agent to detect breast CSCs.

SUMMARY

Thus, in accordance with the present disclosure, there is provided a compound having the formula:

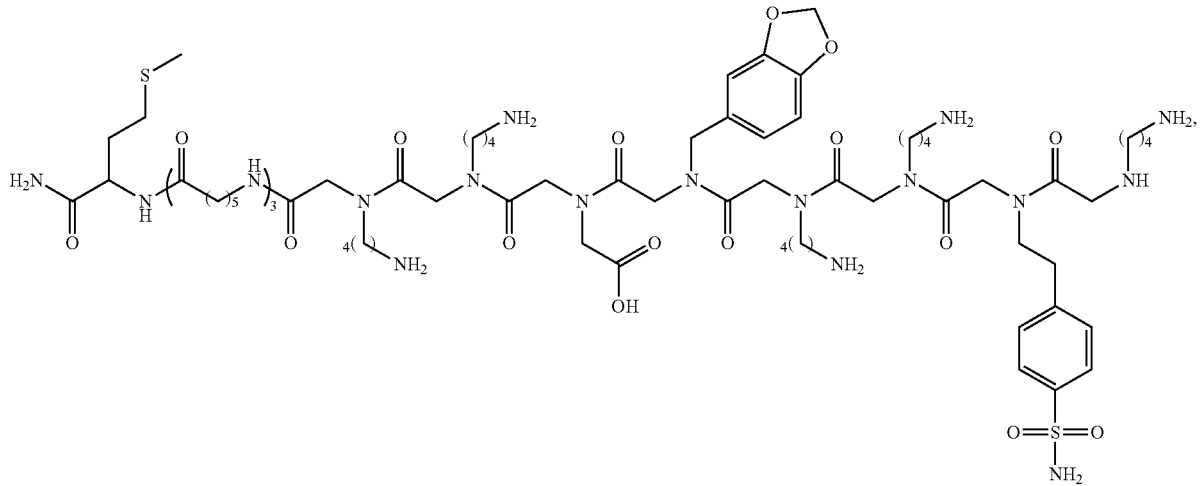

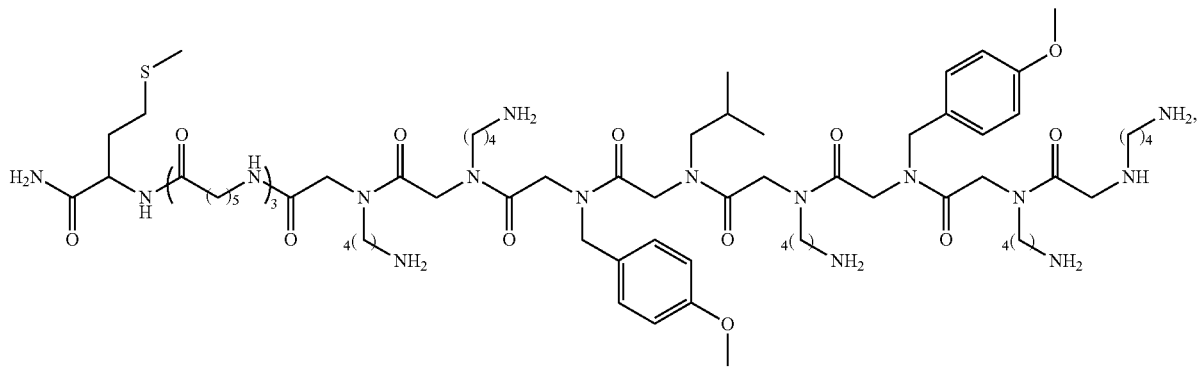

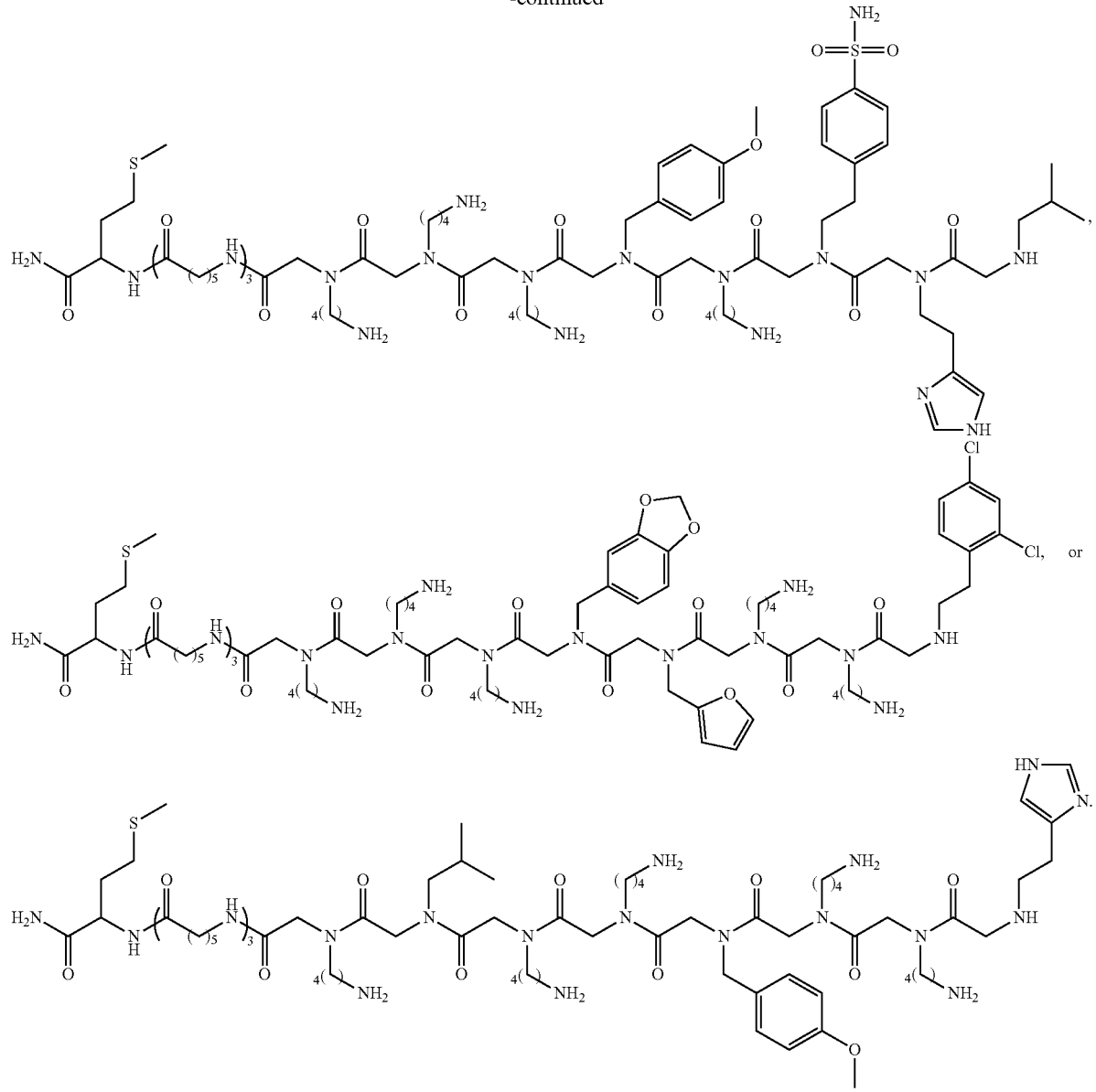

The compound may be linked through the terminal amide group to a detectable agent, a therapeutic agent, or a scaffold. Alternatively, the compound maybe modified to contain a sulfhydril functional group (such as through cysteine coupling) and conjugated to a detectable agent, a therapeutic agent, or a scaffold via a thioether linkage, wherein the detectable agent, therapeutic agent, or scaffold comprise sulfhydril reactive molecules (such as a maleimide).

Also provided is method of binding a compound to a cancer stem cell (CSC) comprising contacting a composition as described above with a CSC. The CSC may exhibit a phenotype of CD24**, CD44+ and/or ALDH+. The CSC may be a breast CSC, such as a breast CSC that is hormone receptor negative, that may be Her2/Neu negative, or that may be both hormone receptor negative and Her2/Neu negative.

Further provided is a method of identifying a cancer stem cell (CSC) in a subject with breast cancer comprising contacting said subject or a sample from said subject with a compound of claim 1 conjugated to a detectable agent. The method may further comprise treating said subject for cancer following detection of a CSC.

In another embodiment, there is provided a method of treating a subject with breast cancer comprising contacting said subject with a compound of claim 1 conjugated to a therapeutic agent. The breast cancer may be primary, recurrent, metastatic or drug resistant. The breast cancer may be hormone receptor negative, Her2/Neu negative or both hormone receptor negative and Her2/Neu negative. The method may further comprise treating said subject with a second cancer therapy, such as radiotherapy, chemotherapy, immunotherapy, toxin therapy, hormonal therapy or surgery. The therapeutic agent may be a radioisotope, chemotherapeutic agent, immunotherapeutic agent, a toxin, or hormonal therapeutic. The therapeutic agent may be a hyperthermal therapeutic agent, such as a gold nanorod. The subject may be treated more than one with said compound, such as weekly, monthly or chronically.

Any embodiment discussed with respect to one aspect of the disclosure applies to other aspects of the disclosure as well.

The embodiments in the Examples section are understood to be embodiments of the disclosure that are applicable to all aspects of the disclosure.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

The following figures form part of the present specification and are included to further demonstrate certain aspects of the present disclosure. The disclosure may be better understood by reference to one or more of these figures in combination with the detailed description of specific embodiments presented herein.

FIGS. 1A-G. Isolation of CSC-specific ligands using cell-binding screening of a combinatorial chemical library. (FIG. 1A) Illustration of the screening. SA=streptavidin. (FIG. 1B) Transmitted (i) and fluorescence (ii, DAPI channel) images of the hit bead displaying CL-1-19-1 (1). The hit bead shows bead-bound red fluorescent cells. The bead itself emits blue fluorescence at DAPI channel. See FIG. 5 for images of other hit beads. (FIG. 1C) Chemical structure of the hit bead 1. See FIG. 6 for structures of other hits. (FIG. 1D) Transmitted (i), fluorescence (ii and iii) and merged (iv) images of a monolayer of MCF-7 cells incubated with Aldefluor™ reagent (a green fluorescence dye for ALDH activity), and then biotinylated-1 (FIG. 8A) followed by streptavidin-conjugated Qdot655 (SA-Qdot655). R: Pearson correlation coefficient. See FIG. 9 for the full images. (FIG. 1E) Affinity isolation of 1-binding (1-B) and 1-nonbinding (1-NB) population from MCF-7 cells. (FIG. 1F) Quantitative analysis of Aldefluor™ staining of W, 1-NB, and 1-B of MCF-7 cells. W represents whole MCF-7 population. Error bars represent s.d. from three independent experiments. Statistical comparison performed by Student's t-test ($^*p<0.05$, $^{**}p<0.005$). See FIG. 10A for fluorescence images of all three populations stained with Aldefluor™. (FIG. 1G) Western blot analysis of stemness-associated transcription factors of W, 1-NB, and 1-B of MCF-7 cells. Error bars represent s.d. from three independent experiments. Statistical comparison performed by Student's t-test ($^*p<0.05$, $^{**}p<0.005$). See FIG. 10B for representative image of Western blot.

FIGS. 2A-D. Binding of 1 to CSC population in triple-negative breast cancer (TNBC). (FIG. 2A) Quantitative analysis of Aldefluor™ staining of $W_{231}$, $1\text{-NB}_{231}$, and $1\text{-B}_{231}$ of MDA-MB-231 cells. Error bars represent s.d. from three independent experiments. Statistical comparison performed by Student's t-test ($^{**}p<0.005$). See FIG. 12A$a$ for fluorescence images of three different populations stained by Aldefluor™. (FIG. 2B) Western blot analysis of stemness-associated transcription factors of $W_{231}$, $1\text{-NB}_{231}$, and $1\text{-B}_{231}$ of MDA-MB-231 cells. No difference is observed for Sox2 expression level among three populations. See FIG. 12B for quantitative analysis. (FIG. 2C) Tissue microarray (TMA) slide containing tissues of patient-derived HER2-overexpressed (n=3), HR$^+$ (n=3), and TNBC (n=3) was incubated with biotinylated-1 followed by streptavidin-conjugated Texas Red (SA-Texas Red). Fluorescence images of representative tissues were shown. DAPI is for nuclear staining. (FIG. 2E) Quantitation of biotinylated-1-binding area in the TMA analysis.

FIGS. 3A-E. Tumorigenicity of 1-binding population of MDA-MB-231 cells. (FIG. 3A) 0.5 million cells of $W_{231}$, $1\text{-NB}_{231}$, or $1\text{-B}_{231}$ of MDA-MB-231 cells were injected into the right flank of female nude mice (n=3 for each population) and tumor growth was monitored over 66 days. See Table 2 for statistical analysis. (FIG. 3B) Sections of tumors derived from $W_{231}$, $1\text{-NB}_{231}$, and $1\text{-B}_{231}$ were incubated with Aldefluor™, and then biotinylated-1 followed by SA-Texas Red. DAPI is for nuclear staining. See FIGS. 13A-B for quantitation. (FIG. 3C) Wound healing after 12 hr the wounds were generated of the cells harvested from tumors derived from $W_{231}$, $1\text{-NB}_{231}$, and $1\text{-B}_{231}$ of MDA-MB-231 cells. Parental MDA-MB-231 was also included in the assay for comparison. See FIGS. 14A-B for time course of wound healing. (FIGS. 3D-E) Western blot analysis of stemness-associated transcription factors (FIG. 3D) and epithelial-mesenchymal markers (FIG. 3E) of cells harvested from tumors. See FIGS. 15A-B for quantitative analysis.

FIGS. 4A-B. (FIG. 4A) Chemical structure of one-bead-one-compound peptoid library. (FIG. 4B) Primary amines used for residues $R_1 \sim R_7$ of the library.

FIG. 5. Transmitted (left column) and fluorescence (right column, DAPI channel) images of hit beads (CL-1-19-6, -18, -19, and -36).

FIGS. 8A-B. Chemical structures of biotinylated-1 (FIG. 8A) and soluble-1 (FIG. 8B).

FIG. 9. Binding of biotinylated-1 to ALDH-positive population in MCF-7 cells. Transmitted and fluorescence images of cells were taken after incubation under indicated conditions. DEAB (N,N-diethylaminobenzaldehyde) is an inhibitor of aldehyde dehydrogenase.

FIGS. 10A-B. (FIG. 10A) Aldefluor™ staining of W, 1-NB, and 1-B of MCF-7 cells. (FIG. 10B) Western blot analysis of stemness-associated transcription factors of W, 1-NB, and 1-B of MCF-7 cells.

FIG. 11. 1-immobilized beads were incubated with MDA-MB-231 or BT549 and excess unbound cells were washed off. The resulting cell-bound beads were incubated with biotin-anti-CD24 or biotin-anti-CD44 followed by strepta-vidin-conjugated Qdot655. Transmitted and fluorescence (QDot655 at DAPI channel) images were shown.

FIGS. 12A-B. (FIG. 12A) Aldefluor™ staining of $W_{231}$, 1-$NB_{231}$, and 1-$B_{231}$ of MDA-MB-231 cells. DAPI is for nuclear staining. (FIG. 12B) Western blot analysis of stemness-associated transcription factors of $W_{231}$, 1-$NB_{231}$, and 1-$B_{231}$ of MDA-MB-231 cells. Error bars represent s.d. from three independent experiments. Statistical comparison performed by Student's t-test ($^{**}p<0.005$).

FIGS. 13A-B. Quantitative analysis Texas Red fluorescence of (FIG. 13A) and Aldefluor™ fluorescence (FIG. 13B) of images in FIG. 3b. Error bars represent s.d. from measurements of three different images taken. Statistical comparison performed by Student's t-test ($^{*}p<0.05$, $^{**}p<0.005$).

FIGS. 14A-B. Images (FIG. 14A) and quantitative analysis (FIG. 14B) of wound healing of the cells harvest from tumors derived from $W_{231}$, 1-$NB_{231}$, and 1-$B_{231}$ of MDA-MB-231 cells at the indicated time after the wound was generated. Statistical comparison performed by Student's t-test ($^{**}p<0.005$).

FIGS. 15A-B. Western blot analysis of stemness-associated transcription factors (FIG. 15A) and epithelial-mesenchymal markers (FIG. 15B) of cells harvested from tumors derived from $W_{231}$, 1-$NB_{231}$, and 1-$B_{231}$ of MDA-MB-231 cells. Error bars represent s.d. from three independent experiments. Statistical comparison performed by Student's t-test ($^{*}p<0.05$, $^{**}p<0.005$).

FIGS. 16A-E. The MALDI-TOF sequence analyses of CL-1-19-1 (FIG. 16A), CL-1-19-6 (FIG. 16B), CL-1-19-18 (FIG. 16C), CL-1-19-19 (FIG. 16D), and CL-1-19-36 (FIG. 16E) after CNBr reaction.

(FIG. 17A) MALDI-TOF data of soluble-1. (FIG. 17B) Analytical HPLC chromatogram of soluble-1. The gradient was a 25 min from 0% to 100% acetonitrile at a flow rate of 1 mL/min.

(FIG. 18A) MALDI-TOF data of biotinylated-1. (FIG. 18B) Analytical HPLC chromatogram of biotinylated-1. The gradient was a 25 min from 30% to 100% acetonitrile at a flow rate of 1 mL/min.

(FIG. 20A) Stability of AuNRs with different concentration of mPEG in 0.2 M NaCl solution. (FIG. 20B) ζ-potential values after/before conjugation and mPEGylated #1-AuNRs with different concentration of #1 ligand. Stability of #1-(FIG. 20C) and Ctrl-AuNRs (FIG. 20D) in 0.2 M NaCl solution, respectively.

(FIG. 21A) UV-Vis spectra of AuNRs with different ligand conjugations. Each absorption peak was normalized to the maximum absorbance value. (FIG. 21B) Hydrodynamic diameter distribution of AuNRs before and after conjugation with #1 and Ctrl ligands. (FIG. 21C) and (FIG. 21D) TEM images of #1- and Ctrl-AuNRs, respectively.

FIGS. 25A-C. FACS analysis of ALDH+ subpopulation in MCF-7 cells using the ALDEFLUOR™ assay. (FIG. 25A) FACS analysis MCF-7 cells treated by DEAB, aldehyde dehydrogenase inhibitor (negative control). This sample was used to establish the baseline of FITC fluorescence to determine the region for ALDH+ subpopulation. (FIG. 25B) FACS analysis of MCF-7 cells treated by ALDELFUOR substrate (BAAA). (FIG. 25C) Western blotting analysis of expressions of stemness transcription factors in MCF-7 whole population, sorted ALDH+ and ALDH−.

FIGS. 26A-B. Examination of selectivity of #1-AuNR toward CSCs. (FIG. 26A) Two-photon luminescence images of whole-MCF-7, ALDH+ and ALDH-subpopulation after incubation with 0.2 nM #1-AuNRs. (FIG. 26B) Quantification of the AuNR on cell surface. Error bars indicate standard deviation from 8 different locations is two samples. Statistical significance was evaluated using ANOVA. ns=not significant.

FIGS. 27A-B. Analysis of CSC subpopulation in MCF-7 under the AuNR-mediated hyperthermia via in situ ALDELFUOR assay. (FIG. 27A) Laser scanning confocal microscope images of MCF-7 cells treated with Ctrl- and #1-AuNR with or without laser irradiation. (FIG. 27B) Quantification of ALDH+ subpopulation in each group ($^{}P=0.001$, $^{*}P<0.001$, ns=not significant.

DESCRIPTION OF ILLUSTRATIVE EMBODIMENTS

Figure 6:
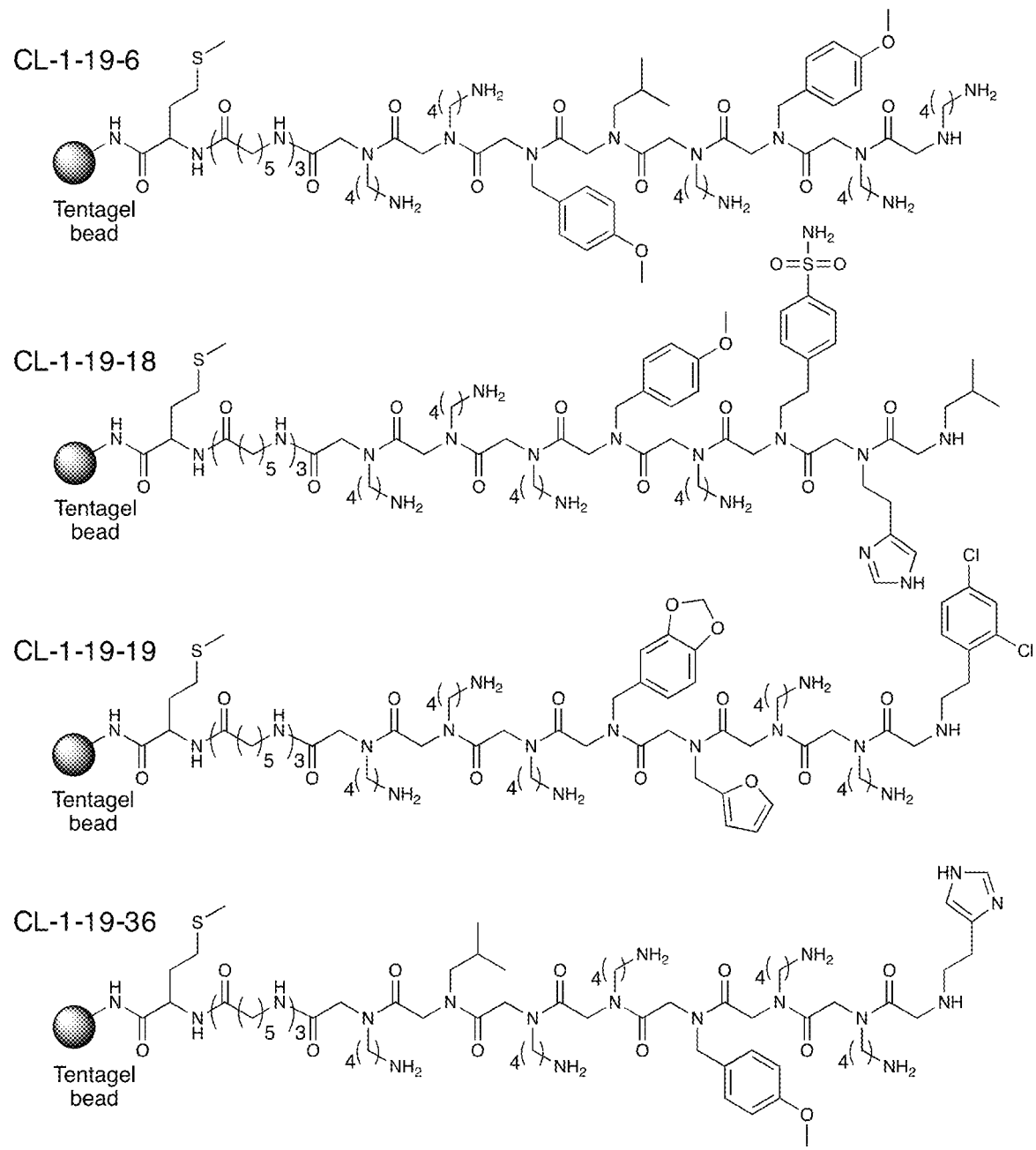
FIG. 6. Chemical structures of the hit beads (CL-1-19-6, -18, -19, and -36).

As discussed above, breast cancer survivors have a high risk of tumor recurrence after about 5 years of the initial treatment, and recurrent cancers are typically resistant to conventional therapies. Recurrent cancer likely involves CSCs that possess phenotypic heterogeneity from the bulk cancer cell populations, and new therapeutic agents targeting CSCs are of great potential value. Here, the inventors describe the isolation of the first synthetic ligands that bind preferentially to CSCs as compared to non-CSCs of breast cancer cells. The ligands were isolated from a cell-binding screen of a combinatorial chemical library under the hypothesis that CSCs carry characteristic cell surface biomolecules that distinguish from non-CSCs. Moreover, the inventors have now employed these ligands in a targeted therapy to treat cancer. These and other aspects of the disclosure are described in detail below.

I. CANCER STEM CELLS

Despite advances in cancer treatment, cancer recurrence, metastasis, and therapy resistance lead to cancer remaining as one of the most fatal diseases. Several studies for a few decades have identified that a small population of cancer cells, which are called cancer stem cells (CSCs), are implicated with a poor prognosis of cancer (Sancho et al., 2015). Recent studies have strongly supported the CSC hypothesis, which demonstrates that a minor population of CSCs are capable of self-renewal, differentiation, proliferation and immune regulation, thereby playing important roles in tumor initiation, recurrence, metastasis, and therapy resistance (Borah et al., 2015; Batlle and Clevers, 2017; Ye et al., 2015). The first experimental evidence for the CSC hypothesis was reported in 1997 from Dick's group (Bonnet et al., 1997). They provided the evidence that human leukemias were driven from a small population of leukemic stem cells. This hypothesis has been extended by providing specific CSC surface markers $CD44^+/CD24^-/lin^-$ in human breast cancers (Al-Hajj et al., 2003; Dontu et al., 2003; Ginestier et al., 2007). Afterward, in many cancers including melanoma, prostate cancer, brain cancer, colon, pancreatic, and head and neck cancers, the biomarkers to identify CSCs have been validated in vitro and in mouse models (Fang et al., 2005; Collins et al., 2005; Wilson et al., 2004; O'Brien et al., 2006; Li et al., 2007; Prince et al., 2007). In recent studies, distinct properties of CSCs compared to non-CSCs have been discovered, such as improvement of DNA damage repair, epithelial-mesenchymal transition, enhanced resistance to physiologic oxidative stress, metabolic reprogramming, and immune invasion and suppression (Ye et al., 2015; Skvortsov et al., 2015; Maugeri-Sacca et al., 2012; Tothova et al., 2007; Ryall et al., 2015; Simsek et al., 2010; Rodriguez-Colman et al., 2017; Beerling et al., 2016; Spranger et al., 2015; Tan et al., 2016). Therefore, successful targeting of CSC is an ultimate goal to overcome challenges of current cancer treatments.

CSCs have been identified as therapeutic targets to overcome the limitations of current cancer drugs and they have inspired the innovative designs of drugs and treatment strategies. Identifying signaling pathways and functional regulators of CSCs in human cancers have contributed to the development of CSC targeted drug design and therapeutic strategies. Direct targeting of CSCs is one of the strategies to eliminate CSC populations. Advanced techniques, such as fluorescence-activated cell sorting (FACS)-based transplantation, barcode-tagging and tracing, lineage tracing, and other biological assays, have identified markers of CSCs (Sancho et al., 215; Ye et al., 2015; Dreissens et al., 2012). For instances, nerve growth factor receptor (CD271) was identified a specific marker of human melanoma (Boiko et al., 2010). Pascual et al. found CD36, the fatty acid receptor, as a target of melanoma and breast cancer (Pacual et al., 2017). As mentioned above, heterogeneous CSC markers, $CD44^+/CD24^-$, are closely associated with breast cancer stem cells. Based on CSC markers, antibody-drug conjugate (ADC) targeting markers of CSCs have been emerged as one of the most promising therapeutic strategies to eliminate CSCs, and many anti-CSC ADCs have been studied and some of these are currently being in clinical trials (de Goeij and Lambert, 2016; Mullard, 20130. For example, cell surface leucine-rich repeat-containing G protein-coupled receptor 5 (LGRS) is a well characterized CSC marker in colon cancer (Junttila et al., 2015). Junttila et al. conjugated monomethyl auristatin E (MMAE; a potent microtubule inhibitor) or NMS818 (topoisomerase-inhibiting anthracycline PNU159682) to human LGRS antibody. The anti-LGRS ADC efficiently shrank tumor size and extended the survival of an aggressive $APC^{min};Kras^{G12D}$ model due to the decrease of the CSC populations (Junttila et al., 2015). Besides, inhibition of mitochondrial oxidative phosphorylation (OxPhos) diminished CSC populations and overcame multidrug resistance in melanoma and pancreatic cancer (Sancho et al., Roesch et al., 2014; Viale et al., 2014).

Identified signaling pathways of CSCs have been facilitated for the development of CSC therapeutic strategies. The well-known CSC pathways are Notch, DLL-3, DDL-4, Wnt, STAT3, Hedgehog, FAK and Nanog (Borah et al., 2015; Takebe et al., 2015; Saunders et al., 2015).

Some CSC signaling pathway-targeted therapies are currently being evaluated in clinical trials. Among them, Hedgehog pathway inhibitor, Vismodegib, has received FDA approval and is in Phase II clinical trials for treating basal cell carcinoma (BCC) (Von Hoff et al., 2009).

Although tremendous research has been devoted to developing therapeutic tools targeting CSC regulators or signaling pathways, several concerns have surfaced concerning safety, efficacy, mutational process, and clinical impact. In the case of CSC-directed therapies, even the same type of cancer can display variability in CSC markers and signaling pathways. In other words, there is a lack of universal CSC-specific markers. Therefore, targeting every CSC in all patients is limited (Frank et al., 2010). In addition, because expression of genes and signaling pathways of CSCs overlap with normal stem cells, these approaches may damage normal stem cells and induce mis-regulation of gene expression (Batlle and Clevers, 2017; Ramos et al., 2017).

Since elimination of CSCs is still a challenging goal in conventional therapies, extensive research has been carried out to develop novel therapeutic strategies. The clinical field of hyperthermia therapy has been a focus due to its potency of direct cancer cell killing, radiosensitizer, and promotion of tumor reoxygenation (Qin and Bischoff, 2010; Rasulov et al., 2016; Dewhirst et al., 2011). Increasing the temperature approximately greater than 41-50° C. halts cellular functions and causes cell death (Pantano et al., 2017). Hyperthermia therapy has shown advances in several cancers. Recently, clinical trials have clearly demonstrated that combined hyperthermia and radiation therapy and/or chemotherapy for treatment of recurrent melanoma, breast cancer, prostate cancer, cervix, head and neck cancer (Rasulov et al., 2016; van Valenberg et al., 2016; Hurwitz et al.,2009; Huang et al., 2018; Overgaard et al., 2009; Hurwitz et al., 2010; Dtta et al., 2016; Zwirner et al., 2019; Harima et al., 2016; Refaat et al., 2015; Mantso et al., 2018; Hoopes et al., 2018; Hove et al., 2019; Mu et al., 2018; Ozhinsky et al., 2018).

II. BREAST CANCER

A. Background

Breast cancer is a cancer that starts in the breast, usually in the inner lining of the milk ducts or lobules. There are different types of breast cancer, with different stages (spread), aggressiveness, and genetic makeup. With best treatment, 10-year disease-free survival varies from 98% to 10%. Treatment is selected from surgery, drugs (chemotherapy), and radiation. In the United States, there were 216,000 cases of invasive breast cancer and 40,000 deaths in 2004. Worldwide, breast cancer is the second most common type of cancer after lung cancer (10.4% of all cancer incidence, both sexes counted) and the fifth most common cause of cancer death. In 2004, breast cancer caused 519,000 deaths worldwide (7% of cancer deaths; almost 1% of all deaths). Breast cancer is about 100 times as frequent among women as among men, but survival rates are equal in both sexes.

B. Symptoms

The first symptom, or subjective sign, of breast cancer is typically a lump that feels different from the surrounding breast tissue. According to the The Merck Manual, more than 80% of breast cancer cases are discovered when the woman feels a lump. According to the American Cancer Society, the first medical sign, or objective indication of breast cancer as detected by a physician, is discovered by mammogram. Lumps found in lymph nodes located in the armpits can also indicate breast cancer. Indications of breast cancer other than a lump may include changes in breast size or shape, skin dimpling, nipple inversion, or spontaneous single-nipple discharge. Pain ("mastodynia") is an unreliable tool in determining the presence or absence of breast cancer, but may be indicative of other breast health issues.

When breast cancer cells invade the dermal lymphatics—small lymph vessels in the skin of the breast—its presentation can resemble skin inflammation and thus is known as inflammatory breast cancer (IBC). Symptoms of inflammatory breast cancer include pain, swelling, warmth and redness throughout the breast, as well as an orange-peel texture to the skin referred to as "peau d' orange." Another reported symptom complex of breast cancer is Paget's disease of the breast. This syndrome presents as eczematoid skin changes such as redness and mild flaking of the nipple skin. As Paget's advances, symptoms may include tingling, itching, increased sensitivity, burning, and pain. There may also be discharge from the nipple. Approximately half of women diagnosed with Paget's also have a lump in the breast.

Occasionally, breast cancer presents as metastatic disease, that is, cancer that has spread beyond the original organ. Metastatic breast cancer will cause symptoms that depend on the location of metastasis. Common sites of metastasis include bone, liver, lung and brain. Unexplained weight loss can occasionally herald an occult breast cancer, as can symptoms of fevers or chills. Bone or joint pains can sometimes be manifestations of metastatic breast cancer, as can jaundice or neurological symptoms. These symptoms are "non-specific," meaning they can also be manifestations of many other illnesses.

C. Risk Factors

The primary risk factors that have been identified are sex, age, childbearing, hormones, a high-fat diet, alcohol intake, obesity, and environmental factors such as tobacco use, radiation and shiftwork. No etiology is known for 95% of breast cancer cases, while approximately 5% of new breast cancers are attributable to hereditary syndromes. In particular, carriers of the breast cancer susceptibility genes, BRCA1 and BRCA2, are at a 30-40% increased risk for breast and ovarian cancer, depending on in which portion of the protein the mutation occurs. Experts believe that 95% of inherited breast cancer can be traced to one of these two genes. Hereditary breast cancers can take the form of a site-specific hereditary breast cancer—cancers affecting the breast only—or breast-ovarian and other cancer syndromes. Breast cancer can be inherited both from female and male relatives.

D. Subtypes

Breast cancer subtypes are typically categorized on an immunohistochemical basis. Subtype definitions are general as follows:

normal (ER+, PR+, HER2+, cytokeratin 5/6+, and HER1+)
luminal A (ER+ and/or PR+, HER2+)
luminal B (ER+ and/or PR+, HER2+)
triple-negative (ER−, PR−, HER2−)
HER2+/ER−(ER−, PR−, and HER2+)
unclassified (ER−, PR−, HER2−, cytokeratin 5/6−, and HER1−)

In the case of triple-negative breast cancer cells, the cancer's growth is not driven by estrogen or progesterone, or by growth signals coming from the HER2 protein. By the same token, such cancer cells do not respond to hormonal therapy, such as tamoxifen or aromatase inhibitors, or therapies that target HER2 receptors, such as Herceptin®. About 10-20% of breast cancers are found to be triple-negative. It is important to identify these types of cancer so that one can avoid costly and toxic effects of therapies that are unlike to succeed, and to focus on treatments that can be used to treat triple-negative breast cancer. Like other forms of breast cancer, triple-negative breast cancer can be treated with surgery, radiation therapy, and/or chemotherapy. One particularly promising approach is "neoadjuvant" therapy, where chemo- and/or radiotherapy is provided prior to surgery. Another drug therapy is the use of poly (ADP-ribose) polymerase, or PARP inhibitors.

E. Traditional Screening and Diagnosis

While screening techniques discussed above are useful in determining the possibility of cancer, a further testing is necessary to confirm whether a lump detected on screening is cancer, as opposed to a benign alternative such as a simple cyst. In a clinical setting, breast cancer is commonly diagnosed using a "triple test" of clinical breast examination (breast examination by a trained medical practitioner), mammography, and fine needle aspiration cytology. Both mammography and clinical breast exam, also used for screening, can indicate an approximate likelihood that a lump is cancer, and may also identify any other lesions. Fine Needle Aspiration and Cytology (FNAC), performed as an outpatient procedure using local anesthetic, involves attempting to extract a small portion of fluid from the lump. Clear fluid makes the lump highly unlikely to be cancerous, but bloody fluid may be sent off for inspection under a microscope for cancerous cells. Together, these three tools can be used to diagnose breast cancer with a good degree of accuracy. Other options for biopsy include core biopsy, where a section of the breast lump is removed, and an excisional biopsy, where the entire lump is removed.

Breast cancer screening is an attempt to find cancer in otherwise healthy individuals. The most common screening method for women is a combination of x-ray mammography and clinical breast exam. In women at higher than normal risk, such as those with a strong family history of cancer, additional tools may include genetic testing or breast Magnetic Resonance Imaging.

Breast self-examination was a form of screening that was heavily advocated in the past but has since fallen into disfavour since several large studies have shown that it does not have a survival benefit for women and often causes considerably anxiety. This is thought to be because cancers that could be detected tended to be at a relatively advanced stage already, whereas other methods push to identify the cancer at an earlier stage where curative treatment is more often possible.

X-ray mammography uses x-rays to examine the breast for any uncharacteristic masses or lumps. Regular mammograms are recommended in several countries in women over a certain age as a screening tool. Genetic testing for breast cancer typically involves testing for mutations in the BRCA genes. This is not generally a recommended technique except for those at elevated risk for breast cancer.

F. Treatments

The mainstay of breast cancer treatment is surgery when the tumor is localized, with possible adjuvant hormonal therapy (with tamoxifen or an aromatase inhibitor), chemotherapy, and/or radiotherapy. At present, the treatment recommendations after surgery (adjuvant therapy) follow a pattern. Depending on clinical criteria (age, type of cancer, size, metastasis) patients are roughly divided into high risk and low risk cases, with each risk category following different rules for therapy. Treatment possibilities include radiation therapy, chemotherapy, hormone therapy, and immune therapy.

Targeted cancer therapies are treatments that target specific characteristics of cancer cells, such as a protein that allows the cancer cells to grow in a rapid or abnormal way. Targeted therapies are generally less likely than chemotherapy to harm normal, healthy cells. Some targeted therapies are antibodies that work like the antibodies made naturally by one's immune system. These types of targeted therapies are sometimes called immune-targeted therapies.

There are currently 3 targeted therapies doctors use to treat breast cancer. Herceptin® (trastuzumab) works against HER2-positive breast cancers by blocking the ability of the cancer cells to receive chemical signals that tell the cells to grow. Tykerb® (lapatinib) works against HER2-positive breast cancers by blocking certain proteins that can cause uncontrolled cell growth. Avastin® (bevacizumab) works by blocking the growth of new blood vessels that cancer cells depend on to grow and function.

Hormonal (anti-estrogen) therapy works against hormone-receptor-positive breast cancer in two ways: first, by lowering the amount of the hormone estrogen in the body, and second, by blocking the action of estrogen in the body. Most of the estrogen in women's bodies is made by the ovaries. Estrogen makes hormone-receptor-positive breast cancers grow. So reducing the amount of estrogen or blocking its action can help shrink hormone-receptor-positive breast cancers and reduce the risk of hormone-receptor-positive breast cancers coming back (recurring). Hormonal therapy medicines are not effective against hormone-receptor-negative breast cancers.

There are several types of hormonal therapy medicines, including aromatase inhibitors, selective estrogen receptor modulators, and estrogen receptor downregulators. In some cases, the ovaries and fallopian tubes may be surgically removed to treat hormone-receptor-positive breast cancer or as a preventive measure for women at very high risk of breast cancer. The ovaries also may be shut down temporarily using medication.

In planning treatment, doctors can also use PCR tests like Oncotype DX or microarray tests that predict breast cancer recurrence risk based on gene expression. In February 2007, the first breast cancer predictor test won formal approval from the Food and Drug Administration. This is a new gene test to help predict whether women with early-stage breast cancer will relapse in 5 or 10 years, this could help influence how aggressively the initial tumor is treated.

Radiation therapy is also used to help destroy cancer cells that may linger after surgery. Radiation can reduce the risk of recurrence by 50-66% when delivered in the correct dose.

III. LIGANDS

Peptoids, or poly-N-substituted glycines, are a class of peptidomimetics whose side chains are appended to the nitrogen atom of the peptide backbone, rather than to the α-carbons (as they are in amino acids). Peptoid-based ligands are advantageous as compared to peptide or protein-based targeting ligands as peptoids are resistant to preolytic degradation and therefore increase serum or plasma stability.

The present inventors generated a one-bead-one-compound combinatorial peptoid library. From this library the following molecules were selected:

[CL-1-19-1]

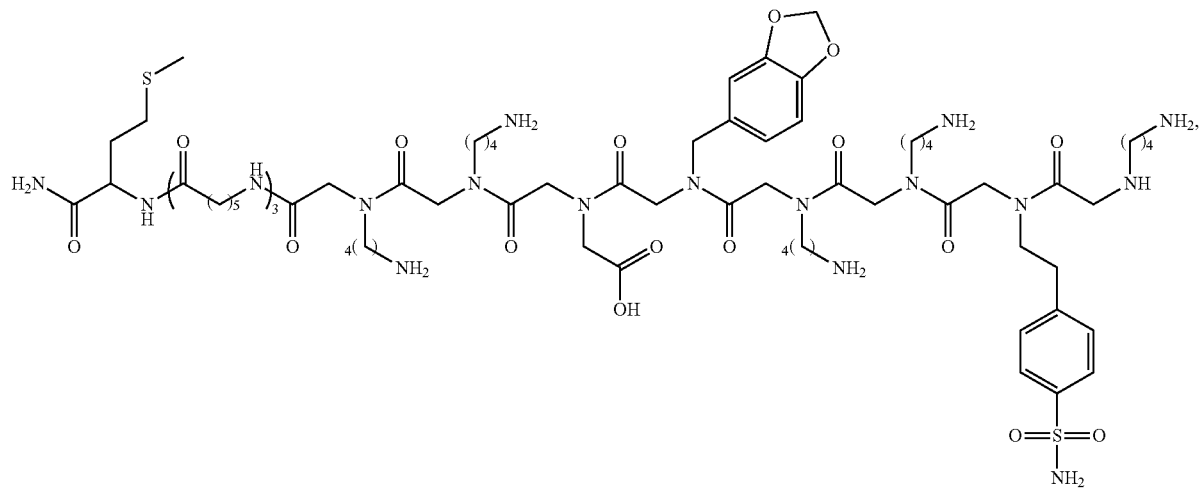

[CL-1-19-6]

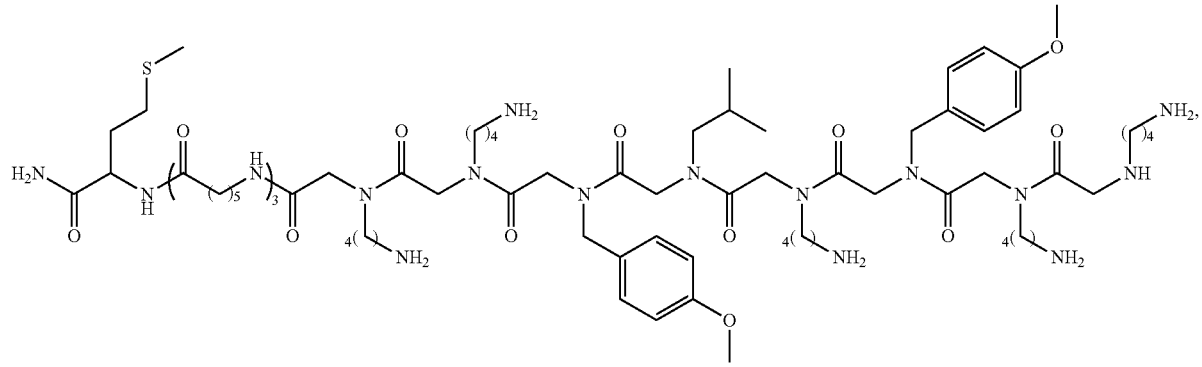

-continued

[CL-1-19-18]

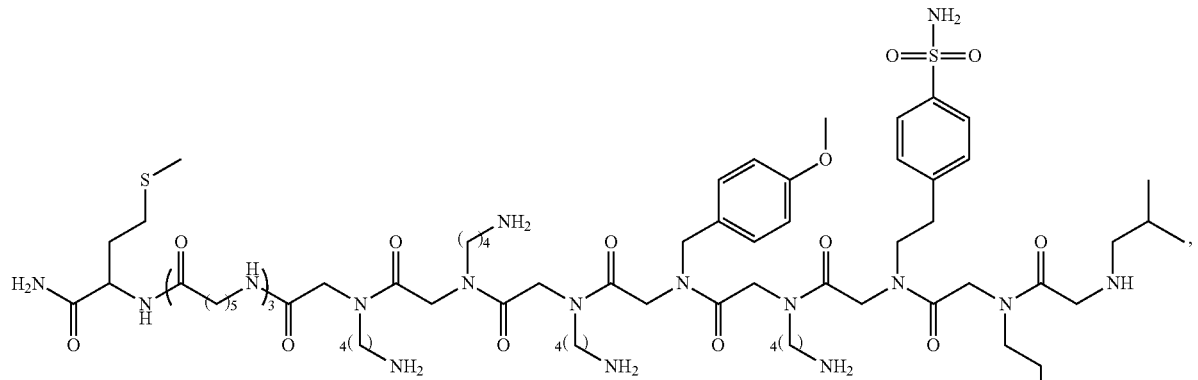

[CL-1-19-19]

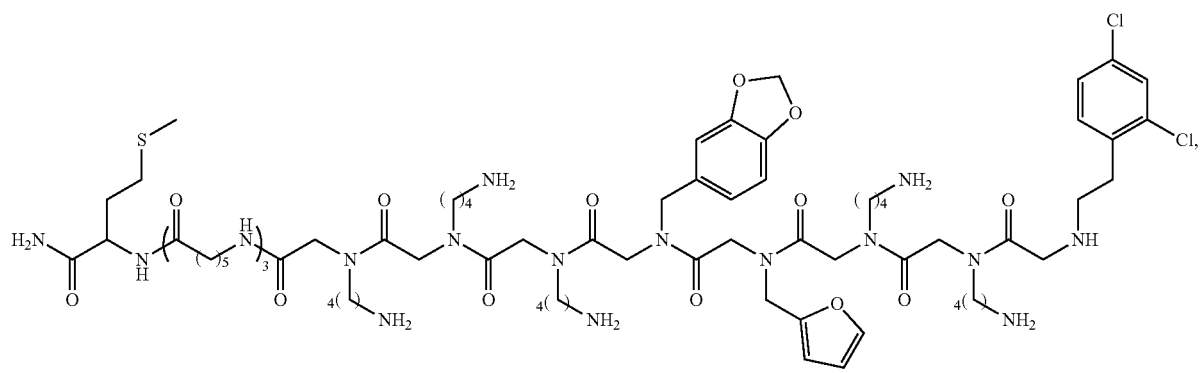

[CL-1-19-36]

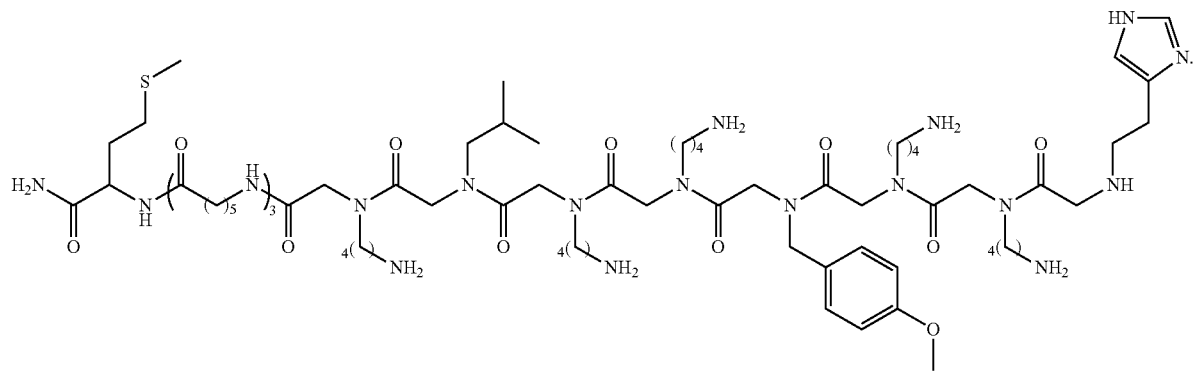

These five compounds were identified as cancer stem cell binders (selectively or specifically) and were then resynthesized for additional testing.

The compounds described herein are advantageously conjugated to other agents so as to take advantage of the CSC targeting properties thereof. Conjugation may involve a direct conjugation with the compound or may involve a linker molecule. An advantageous point of conjugation is the terminal amide group resulting in a structure:

[AGENT]-NH—C(O)-[PEPTOID]

Another conjugation method is possible in which the compound is modified to have sulfhydril functional group (such as through cysteine coupling) and then conjugated via a thioether linkage to other agents that are modified with sulfhydril reactive molecules such as a maleimide.

IV. NANORODS AND PHOTOTHERMAL THERAPY

A. Nanorods

Nanorods are one morphology of nanoscale objects. Each of their dimensions range from 1-100 nm. They may be synthesized from metals or semiconducting materials. Standard aspect ratios (length divided by width) are 3-5. Nanorods are produced by direct chemical synthesis. A combination of ligands acts as shape control agents and bond to different facets of the nanorod with different strengths. This allows different faces of the nanorod to grow at different rates, producing an elongated object.

Nanorods may be made of gold, zinc oxide or even cationic exchange materials. Nanorods based on semiconducting materials have also been investigated for application as energy harvesting and light emitting devices. ZnO nanorods exhibit electric-field mediated tunable photoluminescence with potential for application as novel sources of near-ultraviolet radiation.

One potential application of nanorods is in display technologies, because the reflectivity of the rods can be changed by changing their orientation with an applied electric field. Another application is for microelectromechanical systems (MEMS). Nanorods, along with other noble metal nanoparticles, also function as theragnostic agents. Nanorods absorb in the near IR and generate heat when excited with IR light. This property has led to the use of nanorods as cancer therapeutics. Nanorods can be conjugated with tumor targeting motifs and ingested. When a patient is exposed to IR light (which passes through body tissue), nanorods selectively taken up by tumor cells are locally heated, destroying only the cancerous tissue while leaving healthy cells intact.

The seed-mediated growth method is the most common and achieved method for synthesizing high-quality gold nanorods. A typical growth protocol involves the addition of citrate-capped gold nanospheres, served as seeds, to the bulk $HAuCl_4$ growth solution. The growth solution is obtained by the reduction of $HAuCl_4$ with ascorbic acid in the presence of cetyltrimethylammonium bromide (CTAB) surfactant and silver ions. Longer nanorods (up to an aspect ratio of 25) can be obtained in the absence of silver nitrate by use of a three-step addition procedure. In this protocol, seeds are sequentially added to growth solution in order to control the rate of heterogeneous deposition and thereby the rate of crystal growth.

The shortcoming of this method is the formation of gold nanospheres, which requires non-trivial separations and cleanings. In one modifications of this method sodium citrate is replaced with a stronger CTAB stabilizer in the nucleation and growth procedures. Another improvement is to introduce silver ions to the growth solution, which results in the nanorods of aspect ratios less than five in greater than 90% yield. Silver, of a lower reduction potential than gold, can be reduced on the surface of the rods to form a monolayer by underpotential deposition. Here, silver deposition competes with that of gold, thereby retarding the growth rate of specific crystal facets, allowing for one-directional growth and rod formation. Another shortcoming of this method is the high toxicity of CTAB. Polymers, such as Polyethylene glycol (PEG), Polyallylamine hydrochloride (PAH) coating, or dietary fibers, such as chitosan, to displace the CTAB out from the nanorod surface without affecting the stability has been reported.

B. Photothermal Therapy

Photothermal therapy (PTT) refers to efforts to use electromagnetic radiation (most often in infrared wavelengths) for the treatment of various medical conditions, including cancer. This approach is an extension of photodynamic therapy, in which a photosensitizer is excited with specific band light. This activation brings the sensitizer to an excited state where it then releases vibrational energy (heat), which is what kills the targeted cells.

Unlike photodynamic therapy, photothermal therapy does not require oxygen to interact with the target cells or tissues. Current studies also show that photothermal therapy is able to use longer wavelength light, which is less energetic and therefore less harmful to other cells and tissues.

Most materials of interest currently being investigated for photothermal therapy are on the nanoscale. One of the key reasons behind this is the enhanced permeability and retention effect observed with particles in a certain size range (typically 20-300 nm). Molecules in this range have been observed to preferentially accumulate in tumor tissue. When a tumor forms, it requires new blood vessels in order to fuel its growth; these new blood vessels in/near tumors have different properties as compared to regular blood vessels, such as poor lymphatic drainage and a disorganized, leaky vasculature. These factors lead to a significantly higher concentration of certain particles in a tumor as compared to the rest of the body. Coupling this phenomenon with active targeting modalities (e.g., antibodies) has recently been investigated by researchers.

The feasibility of using gold nanorods for both cancer cell imaging as well as photothermal therapy has been investigated. For example, antibodies (anti-EGFR monoclonal antibodies) conjugated to the surface of gold nanorods allows the nanorods to bind specifically to certain malignant cancer cells (HSC and HOC malignant cells). After incubating the cells with the gold nanorods, a laser (e.g., 800 nm Ti:sapphire) can be used to irradiate the cells at varying powers. Successful destruction of malignant cancer cells has been reported while nonmalignant cells were unharmed.

When AuNRs are exposed to NIR light, the oscillating electromagnetic field of the light causes the free electrons of the AuNR to collectively coherently oscillate. Changing the size and shape of AuNRs changes the wavelength that gets absorbed. A desired wavelength would be between 700-1000 nm because biological tissue is optically transparent at these wavelengths. While all AuNP properties are sensitive to change in their shape and size, Au nanorods properties are extremely sensitive to any change in any of their dimensions regarding their length and width or their aspect ratio. When light is shone on a metal NP, the NP forms a dipole oscillation along the direction of the electric field. When the oscillation reaches its maximum, this frequency is called the surface plasmon resonance (SPR). AuNR have two SPR spectrum bands: one in the NIR region caused by its longitudinal oscillation which tends to be stronger with a longer wavelength and one in the visible region caused by the transverse electronic oscillation which tends to be weaker with a shorter wavelength. The SPR characteristics account for the increase in light absorption for the particle. As the AuNR aspect ratio increases, the absorption wavelength is redshifted and light scattering efficiency is increased. The electrons excited by the NIR lose energy quickly after absorption via electron-electron collisions, and as these electrons relax back down, the energy is released as a phonon that then heats the environment of the AuNP which in cancer treatments would be the cancerous cells. This process is observed when a laser has a continuous wave onto the AuNP. Pulsed laser light beams generally results in the AuNP melting or ablation of the particle. Continuous wave lasers take minutes rather than a single pulse time for a pulsed laser, continues wave lasers are able to heat larger areas at once.

V. METHODS OF DIAGNOSIS AND THERAPY

The present disclosure contemplates the use of compounds as described herein to target cancer cells for both diagnostic and therapeutic purposes.

"Treatment" and "treating" refer to administration or application of a therapeutic agent to a subject or performance of a procedure or modality on a subject for the purpose of obtaining a therapeutic benefit of a disease or health-related condition, in this case cancer.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease, in this case a prolonged life span, reduced tumor growth, tumor regression, reduced metastasis, reduction in likelihood of recurrence, induction of remission, or improved quality of life.

"Prevention" and "preventing" are used according to their ordinary and plain meaning to mean "acting before" or such an act. In the context of a particular disease, those terms refer to administration or application of an agent, drug, or remedy to a subject or performance of a procedure or modality on a subject for the purpose of blocking the onset of a disease or health-related condition, in this case cancer.

The subject can be a subject who is known or suspected of being free of a particular disease or health-related condition, in this case cancer, at the time the relevant preventive agent is administered. The subject, for example, can be a subject with no known disease or health-related condition (i.e., a healthy subject).

In additional embodiments of the disclosure, methods include identifying a patient in need of treatment. A patient may be identified, for example, based on taking a patient history or based on findings on clinical examination.

A. Diagnosis

In some embodiments, the disclosure provides a method of diagnosing using compounds according to the present disclosure. In some cases, the compounds may be intrinsically labeled, such as constructed or radioisotopes. In other embodiments, the compounds will be linked to a diagnostic agent or "label" and the compounds will help deliver the label to the CSC in a cell-selective or cell-specific fashion.

Potential diagnostic agents that may be linked to compounds of the present disclosure include radioactive tracers, MRI contrast agents, dyes, fluorescent molecules, chemiluminescent molecules, and diagnostic nanoparticles.

B. Therapy

In some embodiments, the disclosure provides a method of treating using compounds according to the present disclosure. The compounds are not in and of themselves therapeutic as they function as CSC binding agents. Thus, the compounds will be linked to a therapeutic cargo or payload and the compounds will help deliver the therapeutic agent to the CSC in a cell-selective or cell-specific fashion.

Potential therapeutic agents that may be linked to compounds of the present disclosure include chemotherapeutic agents, radiotherapeutic agents, toxins, hormonal therapeutics, immunotherapeutics, photothermal therapy agents (e.g., gold nanorods), and photodynamic therapy agents.

C. Formulations and Routes for Administration to Patients

Where clinical (e.g., diagnostic and therapeutic) applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions. Of particular interest is direct intratumoral administration, perfusion of a tumor, or administration local or regional to a tumor, for example, in the local or regional vasculature or lymphatic system, or in a resected tumor bed (e.g., post-operative catheter). For practically any tumor, systemic delivery also is contemplated. This will prove especially important for attacking microscopic or metastatic cancer.

The active compounds may also be administered as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agent, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The actual dosage amount of a composition of the present disclosure administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

D. Cancer Combination Treatments

As discussed above, the disclosure contemplates cancer therapy. One goal of current cancer research is to find ways to improve the efficacy of conventional chemo-, radio-, immuno- and hormonal therapy by combining such traditional therapies with other anti-cancer treatments like those described here. It also is conceivable that more than one administration of the treatment will be desired. Here, the methods of the present disclosure, i.e., CSC targeted therapies, may be advantageously combined with one or more distinct conventional therapies.

1. Chemotherapy

A wide variety of chemotherapeutic agents may be used in accordance with the present disclosure. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); el eutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran;

spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and can be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of your internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with gen silencing therapy discussed above. In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p9'7), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants, e.g.,*Mycobacterium*

*bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

An emerging immunotherapy is immune checkpoint blockade therapy. Current checkpoint blockage therapy using antibodies to target PD1/PDL1 or/and CTLA4 only have limited success rates from 15% to 35%, suggesting that combining these therapies with other cancer therapies may be advantageous.

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Gene Therapy

In yet another embodiment, the secondary treatment is a gene therapy in which a therapeutic polynucleotide is administered. A variety of proteins are encompassed within the disclosure, some of which are described below.

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present disclosure, it is contemplated that anti-sense mRNA or siRNA directed to a particular inducer of cellular proliferation is used to prevent expression of the inducer of cellular proliferation.

The proteins FMS and ErbA are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

The tumor suppressor oncogenes function to inhibit excessive cellular proliferation. The inactivation of these genes destroys their inhibitory activity, resulting in unregulated proliferation. The tumor suppressors p53, mda-7, FHIT, p16 and C-CAM can be employed.

In addition to p53, another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the p16' has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a class of CDK-inhibitory proteins that also includes $p16^B$, p19, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Mori et al., 1994; Okamoto et al., 1994; Nobori et al., 1995; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

Other genes that may be employed according to the present disclosure include Rb, APC, DCC, NF-1, NF-2, WT-1, MEN-I, MEN-II, zac1, p'73, VHL, MMAC1, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

6. Other Agents

It is contemplated that other agents may be used with the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon α, β, and γ; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present disclosure to improve the anti-hyerproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

E. Dosage

Compounds of the present disclosure be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight. The unit dose, for example, can be administered by injection (e.g., intravenous or intramuscular, intrathecally, intratumorally or directly into an organ), inhalation, or a topical application.

In one embodiment, the unit dose is administered once a day, e.g., or less frequently less than or at about every 2, 4, 8 or 30 days. In another embodiment, the unit dose is not administered with a frequency (e.g., not a regular frequency). For example, the unit dose may be administered a single time. Because oligonucleotide agent can persist for several days after administering, in many instances, it is possible to administer the composition with a frequency of less than once per day, or, for some instances, only once for the entire therapeutic regimen.

A compound as describe herein can be administered in a single dose or in multiple doses. Where the administration of the compound is by infusion, the infusion can be a single sustained dose or can be delivered by multiple infusions. Injection of the compound can be directly into the tissue at or near the site of interest, such as a tumor. Multiple injections of can be made into the tissue at or near the site.

In a particular dosage regimen, the compound is injected at or near a disease site once a day for seven days, for example, into a tumor, a tumor bed, or tumor vasculature. Where a dosage regimen comprises multiple administrations, it is understood that the effective amount of the compound administered to the subject can include the total amount of compound administered over the entire dosage regimen. One skilled in the art will appreciate that the exact individual dosages may be adjusted somewhat depending on a variety of factors, including the specific compound being administered, the time of administration, the route of administration, the nature of the formulation, the rate of excretion, the particular disorder being treated, the severity of the disorder, the pharmacodynamics of the oligonucleotide agent, and the age, sex, weight, and general health of the patient. Wide variations in the necessary dosage level are to be expected in view of the differing efficiencies of the various routes of administration. Variations in these dosage levels can be adjusted using standard empirical routines of optimization, which are well-known in the art. The precise therapeutically effective dosage levels and patterns can be determined by the attending physician in consideration of the above-identified factors.

In one embodiment, a subject is administered an initial dose, and one or more maintenance doses of a compound. The maintenance dose or doses are generally lower than the initial dose, e.g., one-half less of the initial dose. The maintenance doses are generally administered no more than once every 5, 10, or 30 days. Further, the treatment regimen may last for a period of time which will vary depending upon the nature of the particular disease, its severity and the overall condition of the patient. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

Certain factors may influence the dosage required to effectively treat a subject, including but not limited to the severity of the disease or disorder, previous treatments, the general health and/or age of the subject, and other diseases present. It will also be appreciated that the effective dosage of the drug used for treatment may increase or decrease over the course of a particular treatment. Changes in dosage may result and become apparent from the results of diagnostic assays. For example, the subject can be monitored after administering a composition. Based on information from the monitoring, an additional amount of the composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds and can generally be estimated based on $EC_{50}$'s found to be effective in in vitro and in vivo animal models.

VI. EXAMPLES

The following examples are included to demonstrate particular embodiments of the disclosure. It should be appreciated by those of skill in the art that the techniques disclosed in the examples which follow represent techniques discovered by the inventor to function well in the practice of the disclosure, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the disclosure.

Example 1

Materials and Methods

Cell culture. MCF-7 and MDA-MB-231 cell lines were cultured in HyClone Dulbecco's Modified Eagle Medium (DMEM) with high glucose (4.5 g/L) and sodium pyruvate. BT549 cells were cultured in HyClone Roswell Park Memorial Institute (RPMI) 1640 medium. All cell culture media were supplemented with 10% fetal bovine serum (FBS), 1% 200 mM L-glutamine and 0.5% 10000 μg/mL Penicillin/Streptomycin antibiotic, and the cultured cells were maintained in a 37° C. incubator with 5% $CO_2$. All cell lines were purchased from American Type Culture Collection (ATCC, Manassas, Va., USA). Cell culture media and supplements were purchased from Fisher Scientific, MA, U.S.A. unless otherwise indicated.

Construction of one-bead-one-compound (OBOC) combinatorial peptoid library. OBOC combinatorial peptoid library was prepared following the reported procedure (Alluri et al. 2003). 1 g of TentaGel resin beads (Rapp Polymere GmbH; diameter 130 μm; 782,770 beads/g; loading 0.26 mmol/g) was added into a polypropylene fritted cartridge (Applied Separations; Size: 35 mL) and swelled with 4 mL of dimethylformamide (DMF) for 1 hr at room temperature. 5 equivalents of Fmoc-Met-OH (Novabiochem), 5 equivalents of 1-hydroxybenzotriazole hydrate ($HOBT·H_2O$; Creosalus), 5 equivalents of 2-(1H-benzotriazol-1-yl)-1,1,3,3-tetramethyluronium hexafluorophosphate (HBTU; Novabiochem), and 4 mL of dry DMF (Acros) were mixed in a vial. After the reagents were dissolved, 10 equivalents of N, N-diisopropylethylamine (DIPEA; Sigma-Aldrich) was added to the solution, and the solution was incubated for 5 min at room temperature. The DMF in the cartridge was drained. Afterwards, the incubated solution was transferred into the cartridge. After 3 hr of shaking at room temperature, the beads were washed with DMF (Fisher Scientific; 3×4 mL), methanol (Fisher Scientific; 2×4 mL), dichloromethane (DCM; Fisher Scientific; 2×4 mL), and DMF (3×4 mL) respectively. To deprotect Fmoc groups of the beads, 4.5 mL of piperidine solution (Sigma-Aldrich; 20% in DMF v/v) was added into the cartridge, and the cartridge was shaken for 10 min at room temperature. After the beads were washed with DMF (2×4 mL), the piperidine reaction was repeated. After the second piperidine reaction, the beads were washed with DMF (3×4 mL), methanol (2×4 mL), DCM (2×4 mL), and DMF (3×4 mL) respectively. 5 equivalents of Fmoc-ε-aminocaproic acid (Bachem), 5 equivalents of $HOBT·H_2O$, 5 equivalents of HBTU, and 4 mL of dry DMF were mixed in a vial. After the reagents were dissolved, 10 equivalents of DIPEA were added to the solution, and the solution was incubated for 5 min at room temperature. The DMF in the cartridge was drained and the incubated solution was transferred into cartridge. After 3 hr of shaking at room temperature, the solution was drained, and the beads were washed with DMF (3×4 mL), methanol (2×4 mL), DCM (2×4 mL), and DMF (3×4 mL) respectively. After Fmoc deprotection, the Fmoc-ε-aminocaproic acid coupling and the Fmoc deprotection were repeated two times. The beads were divided equally into 11 medium cartridges (Size: 6 mL). For acetylation, 349 μL of 0.4 M chloroacetic acid (CAA; Acros) solution in dry DMF and 82 μL of 2 M N,N'-diisopropylcarbodiimide (DIC; Sigma-Aldrich) solution in dry DMF were added into each cartridge, and the cartridges were shaken at 35° C. for 6 min. Following the reaction, the beads were washed with DMF (3×0.5 mL), methanol (2×0.5 mL), DCM (2×0.5 mL), and N-Methyl-2-pyrrolidone (NMP; Fisher Scientific; 3×0.5 mL) respectively. Each set of beads was shaken with 0.5 mL of N-Boc-1, 4-diaminobutane (Sigma-Aldrich; 2 M in dry NMP) at 35° C. for 3 h. After the beads were washed with DMF (3×0.5 mL), methanol (2×0.5 mL), DCM (2×0.5 mL), and DMF (3×0.5 mL) respectively, split-pool synthetic method was introduced to construct the remaining peptoid residues of the OBOC library. In the split-pool synthetic method, each set of beads was coupled with CAA and DIC solutions at 35° C. for 6 min. After the beads were washed with DMF (3×0.5 mL), methanol (2×0.5 mL), DCM (2×0.5 mL), and NMP (3×0.5 mL) respectively, 11 sets of beads were coupled with 11 different amines (2 M in dry NMP) in 11 medium cartridges at 35° C. for 1.5 h. After each set of beads were washed with DMF (3×0.5 mL), methanol (2×0.5 mL), DCM (2×0.5 mL), and DMF (3×0.5 mL), 11 medium cartridges of beads were pooled in a large cartridge, mixed well and split into 11 medium cartridges again. The split-pool synthetic method was performed seven times to acquire the desired OBOC library.

High-throughput screening to isolate hit beads that bind to breast cancer cells with a $CD24^-/CD44^+$ phenotype. 59 mg of the OBOC library beads was shaken with 1 mL of TFA cleavage cocktail (containing 95% TFA, 2.5% triisopropylsilane, 2.5% $H_2O$) for 2 hr at room temperature and washed with DCM (10×1 mL), H$_2$O (5×1 mL), methanol (5×1 mL), and DCM (5×1 mL) respectively. The beads were swelled in 1 mL of DMF for 1 hr at room temperature and were washed with H$_2$O (5×1 mL) and DMEM (5×1 mL). 5 mL of 10% FBS DMEM w/3% BSA (EMD Millipore Corp) was added into the cartridge. The bead suspension was transferred into a 15-mL centrifuge tube and incubated for 1 hr at room temperature. MCF-7 cells of two 100 mm petri dishes were washed with 5 mL of Dulbecco's phosphate-buffered saline (DPBS; HyClone) per dish and detached using 2 mL of enzyme free cell dissociation buffer (Gibco) per dish. 5 mL of 10% FBS DMEM was used to combine cells from both dishes. The combined cells were centrifuged at 500 rpm at room temperature for 2 min, and the supernatant was removed. The cell pellet was resuspended with 5 mL of 10% FBS DMEM w/3% BSA. The cell suspension was passed through a 70 μm sterile cell strainer (BD) and counted by hemocytometer (Fisher Scientific). The cell suspension was added to a solution of 10% FBS DMEM w/3% BSA such that 2.5×10$^6$ cells were present in 5 mL of 10% FBS DMEM w/3% BSA. The solution containing the OBOC library beads was drained, and the cell suspension was added into the tube containing the OBOC library beads followed by incubation on the rocker at 37° C. After 30 min of incubation, the tube was removed from the rocker, and the supernatant was removed immediately after the beads had settled at the bottom of the tube. 5 mL of 4% formaldehyde solution was added to the OBOC library, and the tube was shaken on the rocker for 15 min at room temperature. The formaldehyde solution was removed, and the beads were washed twice with 5 mL of DPBS w/3% BSA. 6 μL of biotinylated CD24 antibody (R&D System) in 5 mL of DPBS w/3% BSA was added to the OBOC library, and the tube was shaken on the rocker for 10 min at room temperature. After the supernatant was removed, the OBOC library was washed with 5 mL of DPBS w/3% BSA. 25 of MagCellect Streptavidin Ferrofluid (R&D System) in 5 mL of DPBS w/3% BSA was added to the OBOC library, and the tube was shaken on the rocker for 10 min at room temperature. DynaMag™-15 (Life Technologies) was used to remove the beads that bound to CD24$^+$ cells. After the supernatant was removed, the OBOC library was washed with 5 mL of DPBS w/3% BSA. 3 μL of biotinylated CD44 antibody (R&D System) in 5 mL of DPBS w/3% BSA was added to the OBOC library, and the tube was shaken on the rocker for 10 min at room temperature. After the supernatant was removed, the OBOC library was washed with 5 mL of DPBS w/3% BSA. 5 of streptavidin-conjugated Qdot655 (Life Technology) in 5 mL of DPBS w/3% BSA was added to the OBOC library, and the tube was shaken on the rocker for 10 min at room temperature. After the supernatant was removed, the OBOC library was washed with 5 mL of DPBS w/3% BSA, and the beads were transferred to a 100 mm petri dish. The beads bound to red-fluorescent cells were selected under the microscope's DAPI filter as hit beads. The hit beads were boiled in 200 μL of sodium dodecyl sulfate (SDS; Fisher scientific) solution (1% in H$_2$O) for 20 min. Afterwards, the hit beads were washed with 200 μL of H$_2$O and transferred into separate microcentrifuge tubes. Each bead was incubated with 200 μL of 0.725 M dithiothreitol (DTT; Fisher scientific) solution in H$_2$O for 24 hr at 37° C. and washed twice with 200 μL of H$_2$O. The beads were cleaved with cyanogen bromide solution (40 mg in 1 mL of acetonitrile: acetic acid: H$_2$O=5:4:1 solution) overnight at room temperature. The bead was removed from each tube and the remaining solution was evaporated using argon gas. 10 μL of 0.1% TFA solution in H$_2$O and 10 μL of 0.1% TFA solution in acetonitrile were used to dissolve the residual peptoid. The structure of peptoid on each hit bead was analyzed by MALDI-TOF (FIGS. 16A-E).

Hit bead re-synthesis. Each hit bead was re-synthesized using 50 mg of TentaGel resin beads. The beads were coupled with Fmoc-Met-OH, Fmoc-ε-aminocaproic acid under scale-down conditions as the OBOC library synthesis protocol. Based on the hit bead's determined sequence, the eight peptoid residues were coupled in the same manner as described above. 1 mg of hit beads was isolated, treated with CNBr solution and characterized by MALDI-TOF (Table 1).

Cell binding validation using hit beads. 2 mg of each re-synthesized hit bead was transferred into small cartridge (size: 2 mL). Each set of beads was deprotected using 0.2 mL of TFA cleavage cocktail and washed with DCM (10× 0.2 mL), H$_2$O (5×0.2 mL), methanol (5×0.2 mL), and DCM (5×0.2 mL) respectively. After being dried, the beads were swelled with 0.2 mL of DMF for 1 hr at room temperature and washed with H$_2$O (5×0.2 mL) and DMEM (5×0.2 mL). Each set of beads was shaken with 0.5 mL of 10% FBS DMEM w/3% BSA on the rocker for 1 hr at room temperature and divided equally into two tubes, one tube for CD24 and the other tube for CD44. 0.5 mL of single cell suspension (1×10$^5$ cells/mL in 10% FBS DMEM w/3% BSA) was transferred into each tube, and the beads were shaken for 1 hr at 37° C. After the beads settled to the bottom, the supernatant was removed. 0.5 mL of 4% formaldehyde was added into each tube, and the tubes were shaken on the rocker for 15 min at room temperature. The formaldehyde solution was removed, and each set of beads was washed twice with 0.5 mL of DPBS w/3% BSA. 0.5 μL of biotinylated CD24 antibody in 0.5 mL of DPBS w/3% BSA was added into the CD24 tube, and 0.5 μL of biotinylated CD44 antibody in 0.5 mL of DPBS w/3% BSA was added into the CD44 tube. Each set of beads was washed twice with 0.5 mL DPBS w/3% BSA. 0.5 mL of streptavidin-conjugated Qdot655 solution (Concentration: 50 μL in 10 mL DPBS w/3% BSA) was added into each tube and shaken on the rocker for 10 min at room temperature. Each set of beads was washed twice with 120 μL of DPBS w/3% BSA, and then 120 μL of DPBS w/3% BSA was added into each tube. The final suspension was transferred to a 96-well plate, and images were taken under the microscope's transmitted filter and DAPI filter.

Figure 17A:
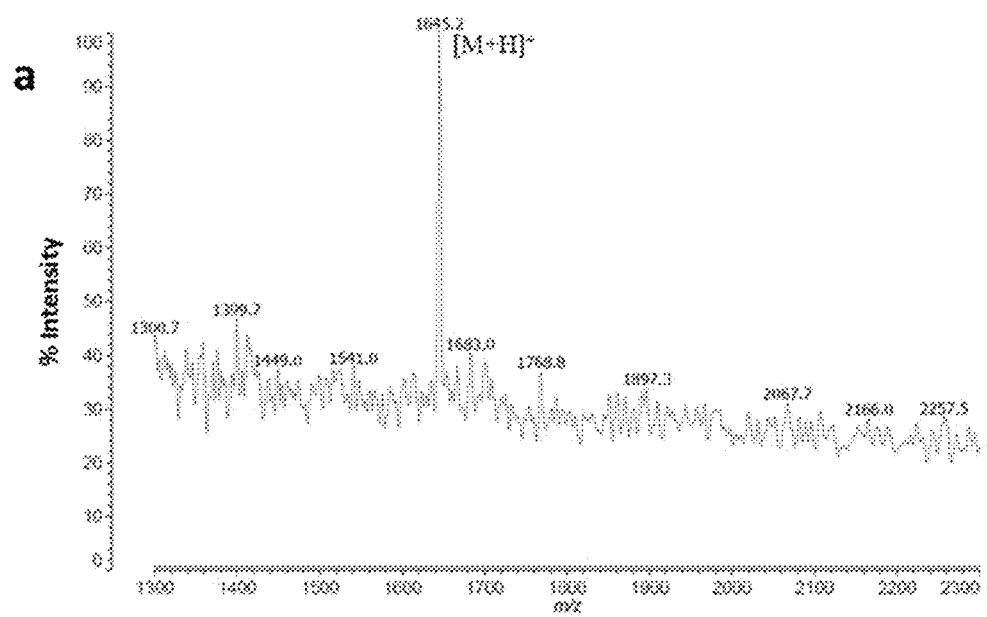
FIGS. 17A-B.
Figure 17B:
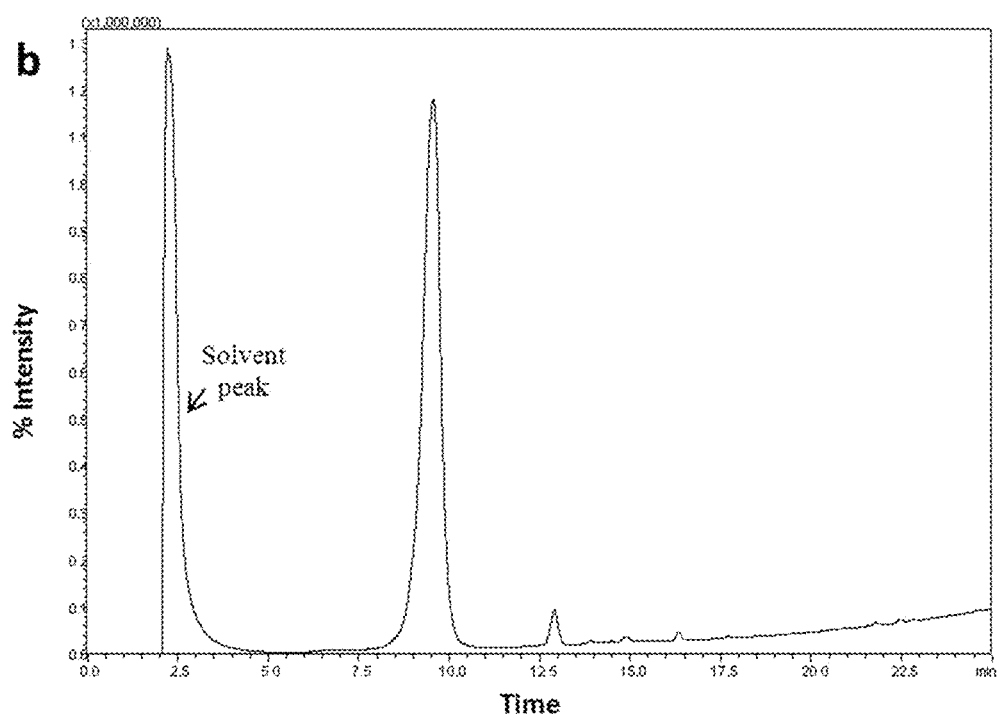
Figure 18A:
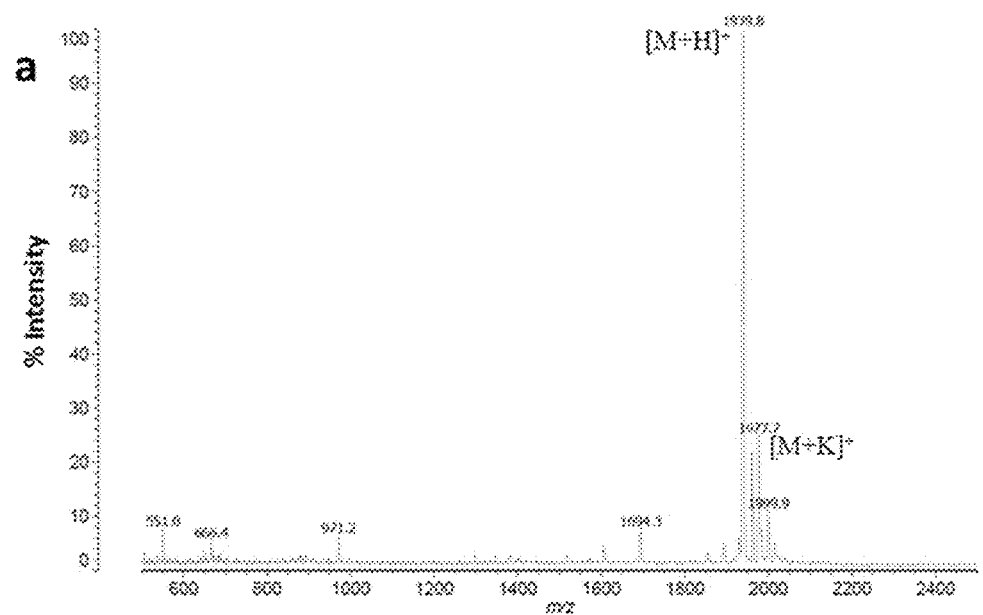
FIGS. 18A-B.
Figure 18B:
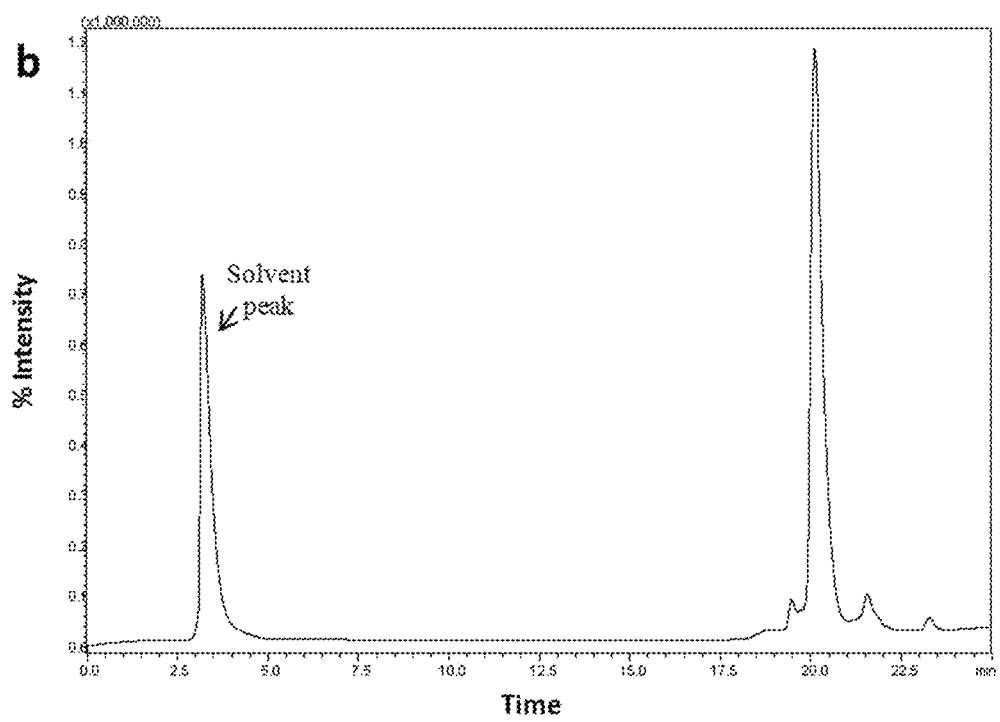
Figure 19:
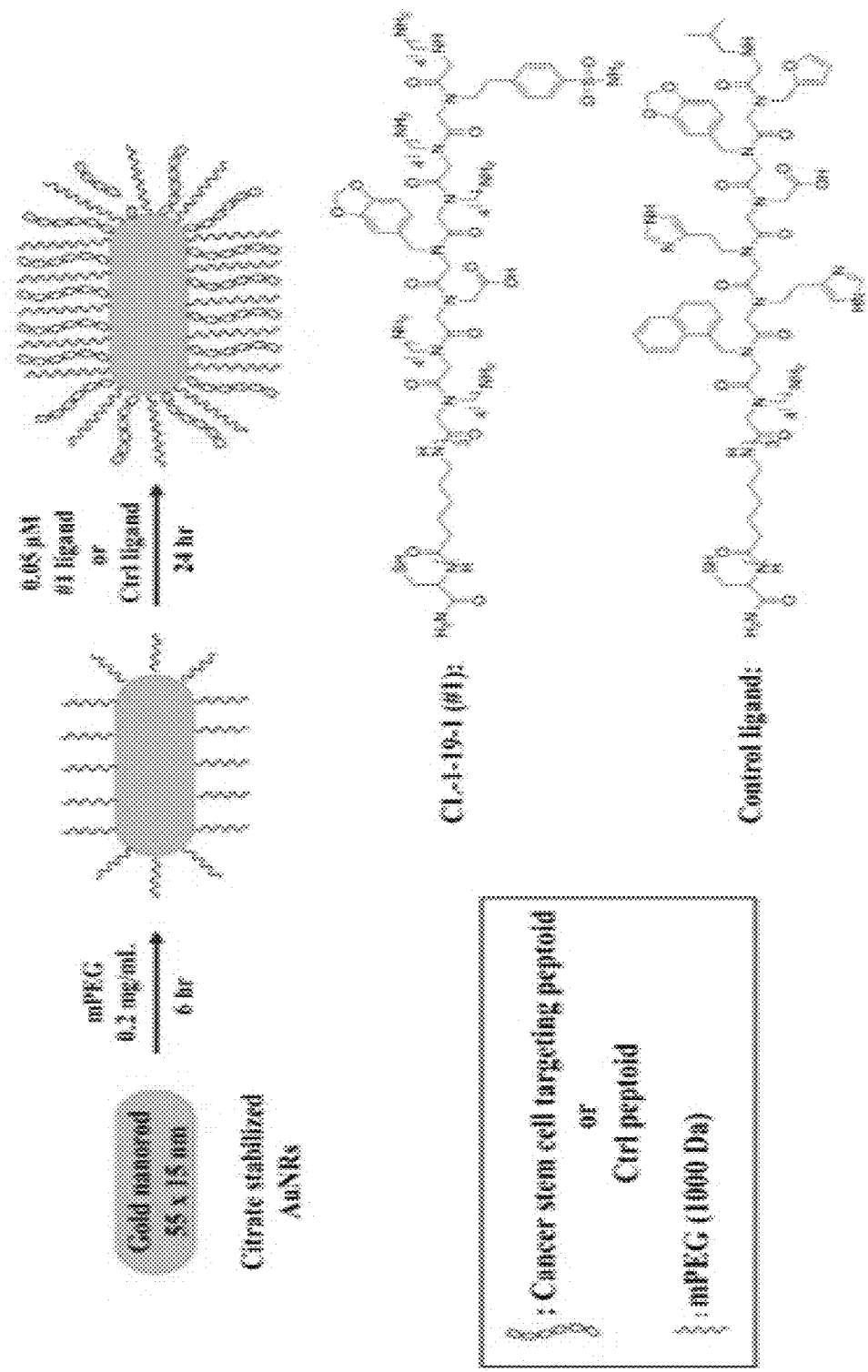
FIG. 19. Preparation of ligand-conjugated AuNRs.

Synthesis and purification of soluble-1 and biotinylated-1. 25 mg of RINK amide MBHA beads (Novabiochem, loading level 0.59 mmol/g) was added into a polypropylene fritted cartridge. The beads were deprotected with 250 μL of piperidine solution. To begin with the synthesis of a soluble derivative, 5 equivalents of Fmoc-Cys(Trt)-OH (Sigma-Aldrich), 5 equivalents of HOBT·H$_2$O, 5 equivalents of HBTU, and 10 equivalents of DIPEA were shaken with deprotected RINK beads in dry DMF at room temperature for 3 h. After Fmoc deprotection, Fmoc-ε-aminocaproic acid and Fmoc deprotection reactions were repeated three times. The beads were coupled with N-Boc-1, 4-diaminobutane under the same conditions as the OBOC library synthesis protocol. Based on the hit bead's determined sequence, the seven remaining residues were coupled in the same manner as described above. For the synthesis of a biotinylated derivative, 5 equivalents of Fmoc-Glu(biotinyl-PEG)-OH (Chem-Impex Int'l. Inc.), 5 equivalents of HOBT·H$_2$O, 5 equivalents of HBTU, and 10 equivalents of DIPEA were shaken with deprotected beads in dry DMF at room temperature for 3 h. After Fmoc deprotection, the RINK beads were shaken with 5 equivalents of Fmoc-DOPA(acetonide)-OH (Novabiochem), 5 equivalents of HOBT·H$_2$O, 5 equivalents of HBTU, 10 equivalents of DIPEA in dry DMF at room temperature for 3 h. After Fmoc deprotection, the beads were coupled with N-Boc-1, 4-diaminobutane under the same conditions as the OBOC library synthesis protocol. Based on the hit bead's determined sequence, the seven remaining residues were coupled in the same manner as described above. Soluble-1 (FIGS. 17A-B) and biotinylated-1 (FIGS. 19A-B) were purified by preparative RP-HPLC and characterized by analytical HPLC and MALDI-TOF.

Isolation of 1-binding population and 1-nonbinding population of MCF-7 or MDA-MB-231. The 1-binding population was isolated by incubating MCF-7 or MDA-MB-231 cells (3 million cells) with 1-immbilized beads (50 mg in dried weight) in DMEM with 5% BSA at 37° C. for 1 h. At the end of incubation, the unbound cells remaining in the incubation medium were collected as the 1-nonbinding population (1-NB). The beads were collected and washed with fresh DMEM to remove any remaining unbound cells, and the bound cells were detached from the beads by incubation with 1X enzyme-free cell dissociation buffer at 37° C. for 5 min. The dissociated cells were collected as the 1-binding population (1-B).

SDS-PAGE and Western blot analysis. For both CSC and EMT markers expression analysis, parental cells (MCF-7 or MDA-MB-231), the isolated 1-binding population and 1-nonbinding population were individually plated in 6-well tissue culture plate, at the seeding density of $2 \times 10^5$ cells per well. When cell confluency reached 80% of plate well surface area, and the adherent cells were washed with ice-cold DPBS and detached from the plate using a cell scrapper, and then transferred into the same tube containing the collected culture medium. After centrifugation to pellet down the cells at 12,500 rpm at 4° C. for 6 min, the cell pellets were resuspended and lysed with 1× Triton-X-100 with 1× protease inhibitor cocktail (Sigma Aldrich). Protein concentration determination of cell lysates was carried out using the Coomassie Dye (PIERCE). 50 µg of total protein per sample was incubated with 5× loading dye containing 2 M DTT at 60° C. for 10 min. Protein samples were then were subjected to SDS-PAGE (Polyacrylamide Gel Electrophoresis). Resolved proteins were then transferred by a wet transfer method to a PVDF membrane (Invitrogen) at 100 V constant voltage for 1 hr using BioRad Mini Trans-Blot Electrophoresis Transfer Cell (BioRad). Upon the completion of wet transfer, the membrane was then blocked with 5% (w/v) fat-free milk in 1× Tris-buffered saline/0.1% (v/v) Tween-20 (TBS-T) for at least 1 h. After three 10 min-washes with 1× TBS-T to remove excess milk, the membrane was incubated with corresponding primary and secondary antibodies. After three 10 min-washes with 1× TB S-T to remove unbound secondary antibodies, the probed proteins were then detected for chemiluminescent signal using SuperSignal Chemiluminescent Substrate (PIERCE).

Aldefluor™ staining for ALDH quantitation. $4 \times 10^4$ MCF-7 or $3 \times 10^4$ MDA-MB-231 cells were seeded on each well of the 8-well chamber well slides (Nunc Lab-Tek) and were incubated for at least 48 hr prior to subsequent treatment. At the end of incubation in 37° C. incubator with 5% $CO_2$, the chamber slide was removed from the incubator, and the wells were washed with DPBS upon aspiration of culture media. Cells were fixed with 4% formaldehyde for 10 min at room temperature. After washing with DPBS, cells were incubated with Aldefluor™ reagent solution from the Aldefluor™ Stem Cell Identification & Isolation kit (Stemcell Technologies). The reagent was diluted in 0.5% BSA in DPBS with 2 mM EDTA. For negative control samples, same amount of DEAB was added instead of the Aldefluor™ reagent. The incubation was performed in dark at 37° C. for 15 min. The stained cells were then washed with cold Aldefluor™ assay buffer. The slide was then examined under fluorescence microscope via GFP filter for imaging. The fluorescence intensities were measured using ImageJ software, and the values were normalized with DAPI.

Aldefluor™ and biotinylated-1 co-localization validation. Following the steps of Aldefluor™ staining, MCF-7 cells were incubated with 500 nM biotinylated-1, and/or 50 µM soluble-1 (100 times more concentrated than conjugated peptoid) for 30 min in dark and on ice. At the end of the incubation, cells were washed with cold Aldefluor™ assay buffer, followed by incubation with 1.25 nM of streptavidin-conjugated Qdot655 (SA-Qdot655) for 20 min in dark and on ice. The stained cells were then washed with cold Aldefluor™ assay buffer provided in the kit. The slide was then examined under fluorescence microscope via GFP filter for imaging. Cell nuclei were stained with 1% Hoechst dye 33342 (Sigma Aldrich) diluted in the 1× assay buffer for 10 min at room temperature and was viewed under fluorescence microscope via DAPI filter. The co-localization significance was calculated using the Pearson correlation coefficient analysis.

Tissue microarray immunofluorescence staining. Tissue microarray slides were purchased from Protein Biotechnologies. The slides were deparaffinized in xylene for 10 min for 3 times, followed by serial rehydration with 100%, 95%, 70%, 50% ethanol, 5 min each for twice. Rehydrated TMA slide was rinsed with deionized water and then DPBS. Antigen retrieval was performed by heating to 100° C. in sodium citrate buffer (pH 6) for 10 min. Cooled slide was then subjected to blocking in 5% BSA in DPBS for 1 hr at room temperature. Incubation with biotinylated-1 diluted with 5% BSA in DPBS was performed on shaker for 1 hr at room temperature. Incubation with 5 nM of streptavidin-conjugated Texas Red (SA-Texas Red, Invitrogen) diluted with 5% BSA in DPBS was performed on shaker for 45 min at room temperature. The slide was then subjected to Hoechst staining (Thermo Scientific) for nucleus for 30 min at room temperature. The slide was then examined under fluorescence microscope via DAPI filter for nucleus imaging, and via Texas Red filter for SA-Texas Red imaging. The fluorescence intensities were measured using ImageJ software, and the values were normalized with DAPI intensities.

Tumor xenograft in nude mice. There are three experimental groups for the mouse xenograft study: the MDA-MB-231 whole population ($W_{231}$), the 1-binding population ($1-B_{231}$), and the 1-nonbinding population ($1-NB_{231}$). 4-week-old homozygous nude female mice (Jackson laboratories) were subjected to subcutaneous injection of 100 µL of the cells ($0.5 \times 10^6$) in HBSS plus 100 µL of Matrigel into the right flank area. Mice were monitored twice a week for tumor growth, weight changes and health conditions. At the end of the xenograft experiment (day 66), all mice were sacrificed in $CO_2$ chamber and the tumors were extracted for further study processing. One representative tumor from each experimental group was isolated, and the isolated tumors were subjected to formalin-fixation paraffin-embedding (FFPE) processing. Tumor tissue micro-sections were then cut and mounted on positively charged microscopic slides for histological study (immunohistological staining procedure follows tissue microarray staining procedure). For tumor tissue microsections staining with Aldefluor™ reagent, tumor microsection slides rinsed with DPBS were incubated with Aldefluor™ reagent solution after the staining procedure with SA-Texas Red. The reagent was diluted in 0.5% BSA in DPBS with 2 mM EDTA. The incubation was performed in dark at 37° C. for 15 min. The stained tissues were then washed with cold Aldefluor™ assay buffer provided in the kit. The slide was examined under fluorescence microscope via GFP filter for Aldefluor™ imaging. The fluorescence intensities were measured using ImageJ software, and the values were normalized with DAPI intensities and compared to the reading of the whole population tumor sample ($W_{231}$-tumor). The co-localization significance was calculated using the Pearson correlation coefficient analysis. The remaining tumors from each experimental group were collected and subjected to cell extraction.

Xenograft tumor cell extraction. Following sacrificing the mice, tumors were isolated from the surrounding tissue and transferred to cold culture medium immediately. Tumor tissues were minced using surgical scissors into small tissue cubes (about 2-4 mm in diameters). The tissue fragments were incubated with enzymatic dissociation solutions in a sequence of collagenase II (200 U/ml; Sigma-Aldrich, St Louis, Mo., USA), DNase I (200 U/ml; Sigma-Aldrich) and then trypsin (5 mg/ml; Invitrogen, Madison, Wis., USA), for 30 min at 37° C. on an orbital rotator. After each incubation period, the fragments were filtered through a 70 μm nylon mesh cell strainer (BD Biosciences, San Diego, Calif., USA). The released cells were centrifuged at 1,200 rpm for 2 min. All the dissociated cells collected from each round of enzymatic dissociation were collected all together and cultured in full growth medium supplied with 10% FBS, 1% additional L-glutamine and 0.5% Penicillin/Streptomycin antibiotic, and the cultured cells were maintained in a 37° C. incubator with 5% $CO_2$.

Wound-healing assay. The "wound" was created by seeding cells in Culture-Insert 2 Well in μ-Dish 35 mm (Ibidi, Germany, catalogue #81176). $2\times10^4$ cells of each experimental group were seeded respectively in each of the two wells and were incubated for 24 hr to allow cell confluence to reach to approximately 100%. The silicone well insert was then carefully removed with tweezers, and the seeding surface was gently rinsed with culture medium to remove floating cells. Cell images were taken at various time points (0 hr, 6 hr, 12 hr and 24 hr respectively) to record and monitor the migration of cells into the "gap". The width of the gap was measured in mm.

Statistical analysis. Statistical significance evaluation of p-values was calculated using paired Student's t-test. A p-value of at least less than 0.05 is considered significant. One-way ANOVA test was used to determine the statistically significant differences between the means of the experimental groups in the mouse tumor xenograft study.

Example 2

Results

The inventors constructed an 8-residue one-bead-one-compound (OBOC) combinatorial peptoid library (Lam et al., 2010; Alluri et al., 2003; Lee et al., 2010) (FIGS. 4A-B). About 46,000 library beads were incubated with MCF-7 cells for 30 min when about 10% of the beads showed bound cells (FIG. 1A). MCF-7 was chosen as a source of CSCs as it presents a small population of breast CSC with a $CD24^-/CD44^+$ phenotype (Phillips et al., 2006). The excessive non-CSC populations such as cells with a $CD24^+/CD44^-$ phenotype in MCF-7 cells can work as competing cells that display cell surface biomolecules competing for ligand binding and thus increase specificity of CSC-specific hit ligands. The hit beads with putative CSCs bound were selected in 2-steps where $CD24^-/CD44^+$ phenotype of bound cells was evaluated. First, the beads with bound cells were incubated with biotinylated CD24 antibody, followed by streptavidin-coupled magnetic nanoparticles. The magnetized beads were removed so that the cells on the remaining beads had a $CD24^-$ phenotype. The remaining beads were incubated with biotinylated CD44 antibody, followed by streptavidin-conjugated Qdot655 (SA-Qdot655). The hit beads with high red fluorescent cells were manually selected under a fluorescence microscope (FIG. 1B and FIG. 5). The inventors isolated 5 hits as breast CSC-specific ligands (FIG. 1C and FIG. 6).

Figure 7:
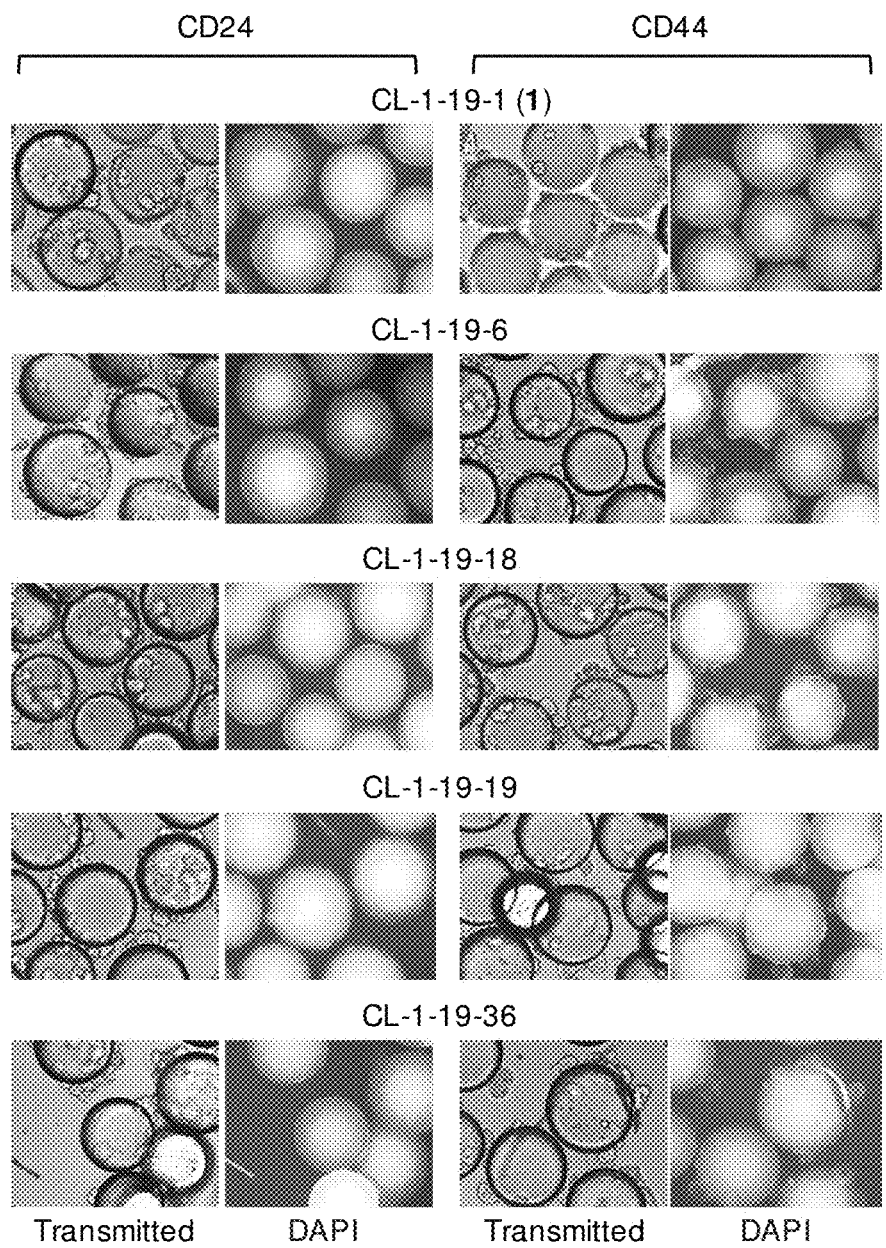
FIG. 7. Resynthesized hit beads were incubated with MCF-7 cells and excess unbound cells were washed off. The resulting cell-bound beads were incubated with biotinylated CD24 antibody or biotinylated CD44 antibody followed by streptavidin-conjugated Qdot655. Transmitted and fluorescence (DAPI for QDot655) images were shown.
Figure 16B:
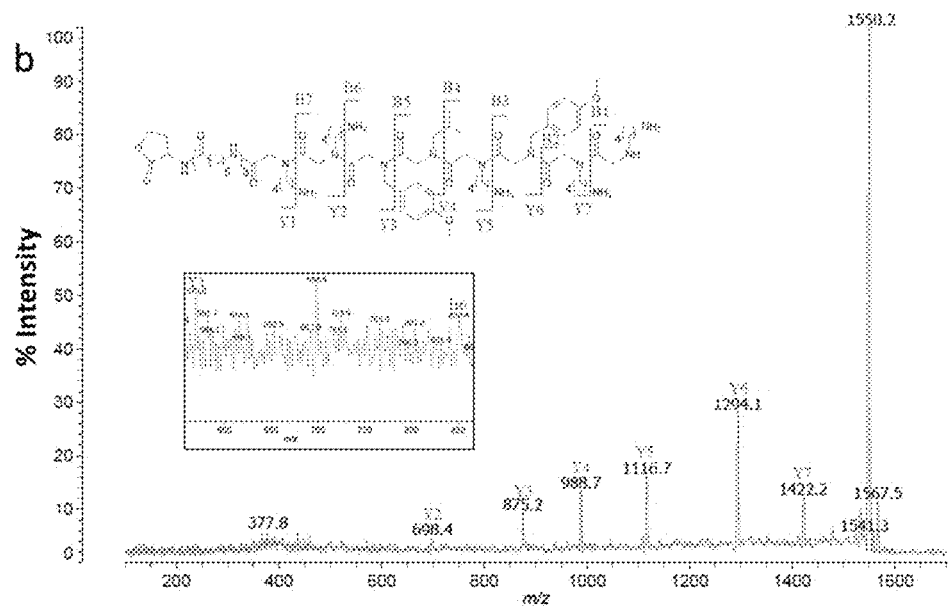
Figure 16C:
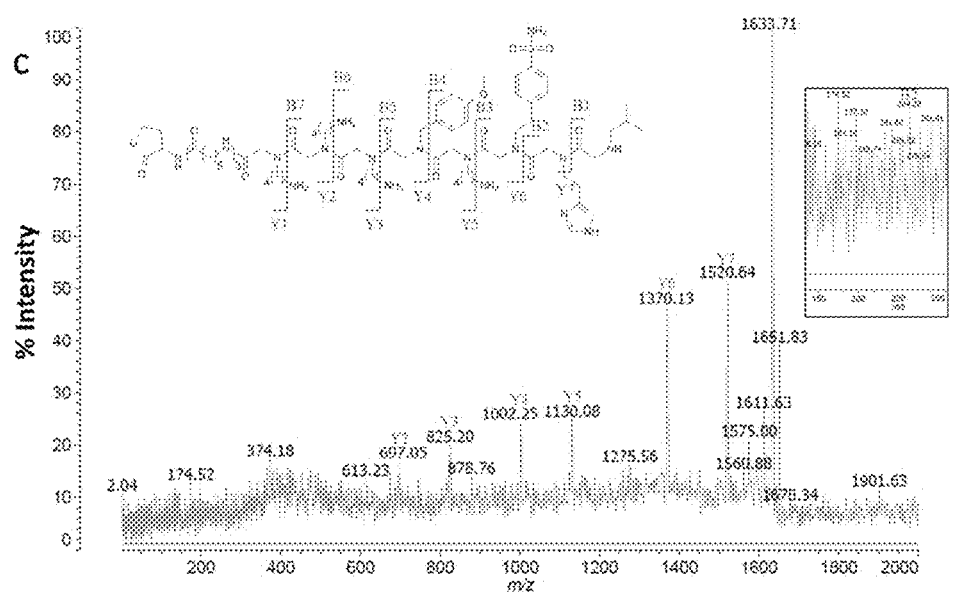
Figure 16D:
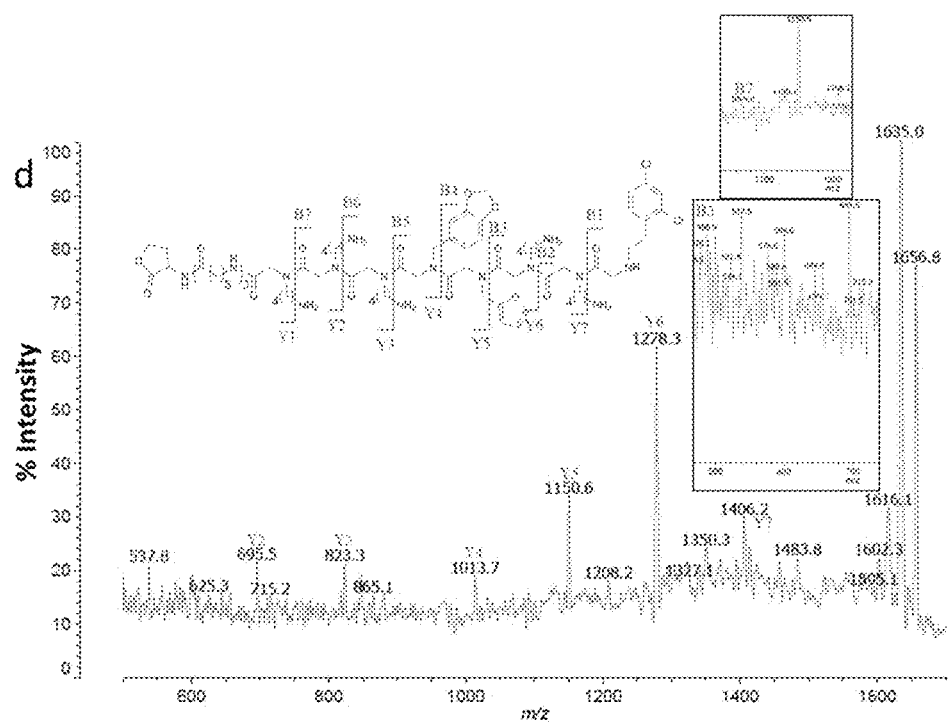
Figure 16E:
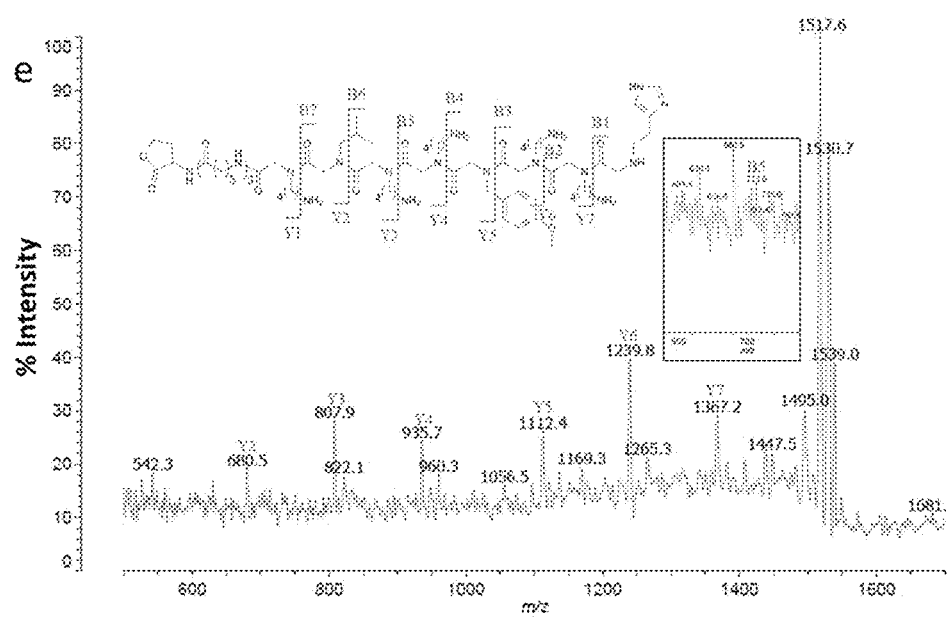

The hit beads were re-synthesized and incubated with MCF-7 cells. Immunofluorescence analysis revealed that all the hits bound to cells with a $CD24^-/CD44^+$ phenotype (FIG. 7) without any significant difference in their binding activity. Among hits, the inventors selected CL-1-19-1 (FIG. 1C, hereafter 1) for further characterization in this study. Characterization of other 4 hits are currently underway and will be published elsewhere. To demonstrate that hit 1 can bind to CSC population of MCF-7 cells even though it is not immobilized on solid support, MCF-7 cells were incubated with biotinylated-1 (FIG. 8A, 0.5 μM), followed by SA-Qdot655. The dihydroxyphenylalanine (DOPA) moiety of the biotinylated-1 is for the future use in periodate-mediated crosslinking (Burdine et al., 2004) of binding receptor(s) for target identification (currently underway and will be published elsewhere). The biotinylated-1 was shown to bind to only small portion (12.5 area % by ImageJ analysis) of MCF-7 cells (FIG. 1D and FIG. 9). Excessive soluble-1 (FIG. 8B, 50 μM) was able to compete with the binding of biotinylated-1 to MCF-7 cells (FIG. 9) indicating the binding was specific to 1. To examine if the ligand-bound cell population represents CSCs, the cells were co-stained with the Aldefluor™, a green fluorescence indicator of aldehyde dehydrogenase (ALDH) activity (Ginestier et al., 2007). Recent studies have suggested that the increased ALDH activity is a hallmark of CSC of various cancer types (Al-Hajj et al., 2003; Ginestier et al., 2007; Zhong et al., 2014). As shown in FIG. 1D, ligand-bound cells showed significant overlap with the $ALDH^+$ cells, indicating the ligand bound to $ALDH^+$ CSC population of MCF-7.

To directly characterize CSC activity of ligand-bound cell population, the inventors utilized 1-immobilized beads as matrices for affinity isolation of the putative CSC population from whole MCF-7 cell population (FIG. 1E). MCF-7 cells were incubated with 1-immobilized beads and 1-binding population (1-B) were isolated in 6.6% yield from the whole MCF-7 population (W). The cells remained unbound to the beads were referred to 1-nonbinding population (1-NB). Aldefluor$^{Tm}$ staining was performed on these populations to show that 1-B displayed 2-fold increase in ALDH activity compared to W (FIG. 1F and FIG. 10A). In contrast, the 1-NB showed 2-fold decrease in ALDH activity compared to W. These data suggest that 1-immobilized bead was able to capture and enrich ALDH CSC population from MCF-7 cells. Next, to examine if the 1-B displays a stemness phenotype, the inventors evaluated the expression level of stemness-associated transcription factors (c-Myc, Klf4, Sox2 and Nanog) (FIG. 1G and FIG. 10B). The inventors found that 1-B displayed a significant increase in the expression level of these transcription factors compared to whole population; ~2 fold of Sox2, ~4.5-fold of c-Myc, ~4-fold of Klf4, and ~7-fold of Nanog. In contrast, 1-NB displayed a decreased level of these transcription factors compared to W, with the exception of Nanog that did not show any change.

Collectively, these results provide strong evidence that 1 captures the CSC population in MCF-7.

To further examine clinical applicability of the ligand 1, the inventors evaluated its binding to triple-negative breast cancer (TNBC) cell lines. TNBC, characterized by mammary tumors that lack detectable expression of estrogen receptor (ER), progesterone receptor (PR) and human epidermal growth receptor 2 (HER2), represents 15% to 20% of all breast cancers (Bauer et al., 2007; Rakha et al., 2009; Dent et al., 2007; Choi et al., 2012; Lehmann et al., 2011). TNBC has a higher rate of early recurrence and poor clinical outcome. However, TNBC lacks defined targeted therapies and molecular markers for detection, thus imposes a greatest challenge in breast cancer treatment. Recent studies suggest that TNBC is enriched with CSCs with a $CD24^-/CD44^+$ phenotype (Idowu et al., 2012). Therefore, the inventors reasoned that 1 would display higher binding to TNBC cells compared to other subtypes of breast cancer cells. Such property of 1 can be utilized to develop TNBC-specific imaging/diagnostic agents. The bead-based binding assay result showed that two TNBC cell lines, MDA-MB-231 and BT549 bound to 1-immobilized beads and the bound cells were found to display a $CD24^-/CD44^+$ phenotype (FIG. 11). To further validate if the bound cells display CSC properties, the inventors isolated 1-binding population ($1\text{-}B_{231}$) and 1-nonbinding population ($1\text{-}NB_{231}$) from the whole population of MDA-MB-231 ($W_{231}$). The isolation yield of CSCs ($1\text{-}B_{231}$) isolation from MDA-MB-231 cells was 18.2% which is about 3-times higher than that from MCF-7, implying higher $CD24^-/CD44^+$ cell population in MDA-MB-231 compared to MCF-7, which is consistent with previous studies (Idowu et al., 2012). Aldefluor™ staining shows that the $1\text{-}B_{231}$ and the $1\text{-}NB_{231}$ display 8-fold increase and 0.5-fold decrease in ALDH activity, respectively compared to $W_{231}$ (FIG. 2A and FIG. 12A). In addition, Western blot analysis reveals that the stemness markers (c-Myc, Klf4, and Nanog) are enriched in $1\text{-}B_{231}$; about 4-9-fold increase compared to $W_{231}$ (FIG. 2B and FIG. 12B). From these results, the inventors concluded that 1 captures CSC population in MDA-MB-231 cells.

To evaluate the binding property of the 1 ligand to patient-derived breast tumors, the inventors utilized a tissue microarray (TMA) comprising tissues of TNBC and non-TNBC tumors. Non-TNBC tumors were further categorized into $HR^+$ and HER2-overexpressed tumors. As the ligand was isolated from in vitro screening using cell lines, it is important to validate it's binding to patient-derived tumors to prove that 1 binding to cancer cells is not simply cell line-dependent but also phenotype-dependent. Incubation of TMA with biotinylated-1, followed by streptavidin-conjugated Texas Red (SA-Texas Red) has revealed that TNBC tumor tissues have highest binding to 1 amongst the tissue sections in the TMA. TNBC tumor sections have 8-fold and 4-fold higher binding to 1 than HER2-overexpressed and $HR^+$ tissues, respectively (FIGS. 2C-D).

CSC population is known to be tumorigenic while non-CSC population does not support tumor growth significantly (Al-Hajj et al., 2003). Therefore, it has been hypothesized that elimination of CSC population will result in tumor degeneration, as new cell growth cannot be initiated from the remaining non-CSC population. A half-million cells of $1\text{-}B_{231}$, $1\text{-}NB_{231}$ or $W_{231}$ were injected into nude mice and tumor growth was monitored over 66 days. As shown in FIG. 3A, $1\text{-}B_{231}$ induced accelerated tumor growth compared to $W_{231}$ and also resulted in bigger tumor size. In contrast, the $1\text{-}NB_{231}$ failed to support any significant tumor formation. These results indicate that 1 captures highly tumorigenic CSC population in MDA-MB-231. Analysis of tumor sections by biotinylated-1 reveals that $1\text{-}B_{231}$-derived tumor contains higher population of 1-binding cells compared to other population-derived tumors (FIG. 3B and FIG. 13A). Importantly, Aldefluor™ staining reveals that the 1-binding cells of the tumors are ALDH, suggesting that the $1\text{-}B_{231}$ is the CSC population responsible for the increased tumorigenicity (FIG. 3B and FIG. 13B). On the contrary, the tumors derived from the $1\text{-}NB_{231}$ showed marked reduction in 1-binding $ALDH^+$ population (FIG. 3B and FIGS. 13A-B). These results are consistent with the CSC tumor hierarchy mode (Kreso & Dick, 2014).

Next, cells harvested from the tumors were used for in vitro assays to further characterize CSC properties of tumor cells from different populations. The cells from the $1\text{-}B_{231}$-derived tumors migrate faster than the cells from $1\text{-}NB_{231}$-, $W_{231}$-derived tumors or parental MDA-MB-231 cells, indicating the tumor derived from the 1-B contains higher migratory activity (FIG. 3C and FIGS. 14A-B). In addition, the cells from $1\text{-}B_{231}$-derived tumor showed markedly increased level of stemness-associated transcription factors, c-Myc, Klf-4 and Nanog (FIG. 3D and FIG. 15A). Recent studies suggest epithelial-mesenchymal transition (EMT) is associated with CSC activity (Kong et al., 2011; Mani et al., 2008). The inventors found that $1\text{-}B_{231}$-derived tumor shows increased level of mesenchymal markers such as N-cadherin and vimentin while $1\text{-}NB_{231}$-derived tumor displays decreases in mesenchymal markers (N-cadherin and vimentin) and increase in epithelial marker, E-cadherin (FIG. 3E and FIG. 15B).

Example 3

Discussion

The inventors isolated a breast CSC-specific ligand 1 by a cell-binding screen of a OBOC combinatorial chemical library. It is important to note that OBOC libraries have been previously utilized to isolate ligands that bind specifically to cancer cells over normal cells (Yao et al., 2009; Matharage et al., 2015; Udugamasooriya et al., 2008). However, utilization of OBOC screen to isolate ligands that bind to the sub-population of the cancer cells such as CSC was first demonstrated in this study. The ligand 1 showed specific binding to the $CD241CD44^+/ALDH^+$ CSC population of MCF-7 and MDA-MB-231 cells. In addition, the 1-binding cell population of MCF-7 and MDA-MB-231 cells displayed a significant increase in CSC markers compared to 1-nonbinding cell populations. Importantly, the 1-binding cell population of MDA-MB-231 cells demonstrated accelerated tumor growth in vivo. These results provide strong evidence indicating that the synthetic ligand 1 binds to CSC population of breast cancer cells. To the best of the inventors' knowledge, this is the first synthetic ligand that was identified to bind directly to breast CSC. Several small molecules have been reported to modulate signaling pathway(s) associated with CSCs (Abetov et al., 2015) but none of them display direct binding to CSC. It is also important to emphasize that the use of ligand 1 alone is sufficient to capture the breast CAC population, which otherwise requires the combination of multiple markers. Taken together, this study provides the first synthetic binder of breast CSC which can be utilized to advance the knowledge of CSCs and develop novel imaging/diagnostic/therapeutic agents to target breast CSC in vivo.

TABLE 1

MS (MALDI-TOF) of all the synthetic compounds

| Compound | Mass calculated ($[M + H]^+$) | Mass observed ($[M + H]^+$) |
|---|---|---|
| CL-1-19-1 (1) | 1627.9 | 1629.0 |
| CL-1-19-6 | 1549.0 | 1551.9 |
| CL-1-19-18 | 1635.0 | 1635.9 |
| CL-1-19-19 | 1638.9 | 1640.9 |
| CL-1-19-36 | 1523.0 | 1524.0 |
| Soluble-1 | 1646.9 | 1645.2 |
| Biotinylated-1 | 1941.0 | 1939.8 |

TABLE 2

One-Way ANOVA Test Analysis on Mouse Xenograft Tumor Growth Rates

Summary of Data

| | Experimental groups | | | |
|---|---|---|---|---|
| | Whole population | 1-Nonbidning population | 1-Binding population | Total |
| N | 17 | 17 | 17 | 51 |
| ΣX | 2114.18 | 1412.02 | 4460.67 | 7986.88 |
| Mean | 124.36 | 83.06 | 262.39 | 156.61 |
| ΣX² | 310893.37 | 129284.94 | 1279697.47 | 9381.75 |
| Standard Deviation | 54.75 | 27.39 | 6828.32 | 96.86 |

Result Details

| Source | SS | df | MS | |
|---|---|---|---|---|
| Between-groups | 299867.38 | 2 | 149933.69 | F = 42.53 |
| Within-groups | 169219.96 | 48 | 3525.42 | P < 0.0001 |
| Total | 469087.34 | 50 | | |

N = number of observations; ΣX = sum of observation values; ΣX² = square of sum of observation values; SS = sum of squares of deviations; df = degree of freedom; MS = mean sum of squares of deviations; F = F-ratio; P = p-value.

Example 4

Hyperthermic Therapy

The efficiency of hyperthermia may also have a great potential to eliminate CSCs and sensitize them to conventional therapies, such as radiotherapy and chemotherapy. Activated heat shock protein by hyperthermia can trigger protein unfolding, thereby inducing cell death (Dubois et al., 1991). Stein et al. reported that the combination of hyperthermia and drug treatment abrogated drug resistance of colon cancer by inactivation of ATP-driven efflux transporters, which are overexpressed in CSCs (Stein et al., 2001). It has been studied that hyperthermia treatment can impede DNA damage repair pathway so that under the hyperthermia treatment, DNA damaging agent and/or radiotherapy can induce excessive DNA damage and can kill CSCs (Oei et al., 2015; Pelicci et al., 2011). Furthermore, hyperthermia can stimulate blood flow, resulting in a decrease of hypoxia. This re-oxygenation changes the microenvironment and decreases the number of quiescent CSCs (Carnero and Lleonart, 2015). Despite conventional hyperthermia therapy has been showing promising results to treat cancer and eradicate CSCs, there are only a few case of hyperthermia therapy in clinical practice possibly due to inadequate hyperthermia applicator tips and delivery systems. Thus, improved technology is necessary for making hyperthermia therapy possible to achieve therapeutic gain.

Comprehensive research of nanotechnologies has progressed and has identified nanoparticles, such as gold nanomaterials, iron oxide nanoparticles, and carbon-based nanomaterials, possessing unique capabilities to enable generation of heat in a desired site (Zhang et al., 2013; Li et al., 2012; Jin et al., 2018; Yao et al., 2014). Plasmonic gold nanomaterials have attracted more attention because they have shown a unique combination of thermal and optical properties. Plasmonic gold nanomaterials convert absorb light into heat, called the photothermal effect. With this consideration, gold nanomaterials with various shapes, such as gold nanorods, gold nanoshells, gold nanoprism, gold nanocages have been studied in the field of photothermal CSCs therapy (Zhang et al., 2016; Xu et al., 2014; Perez-Hernandez et al., 2015; Sun et al., 2014a,b). Atkinson et al. reported that gold nanoshell-mediated hyperthermia therapy can sensitize breast cancer stem cells to radiation therapy (Atkinson et al., 2010).

However, there are limitations in CSC targeted nanomaterials-mediated photothermal therapies. This could be the lack of absolute biomarkers and the need for a combination of multiple markers to target the CSCs. For this reason, many studies have tried to deliver their nanomaterials thorough an enhanced permeability and retention (EPR) effect, but this can also lead to side effects through non-specific targeting (Xu et al., 2014; Atkinson et al., 2010). In 2018, the inventors have reported a synthetic ligand that selectively binds to CSC subpopulation over non-CSC subpopulation (Chen et al., 2018). Through cell-based screening using on bead one compound library the inventors identified the ligand. The ligand showed that it can selectively bind to $CD24^-/CD44^+/ALDH^+$ CSC population of breast cancer cells, MCF-7 and MDA-MB-231. It is noteworthy that the ligand alone is sufficient to identify the CSC population, whereas the combination of multiple markers was required for it (Chen et al., 2018).

In this study, CL-1-19-1 was employed to develop the novel strategy for CSC elimination. The AuNR conjugated with CL-1-19-1 and mPEG was explored its capacity in vitro. This AuNR exhibited high selectively toward to $ALDH^+$ subpopulation, considered CSCs. Under the nano-second laser irradiation (532 nm), MCF cells showed more than 50% decreased number of $ALDI-1^+$ cell populations versus control groups, suggesting that the #1-AuNR (#1: CL-1-19-1) can selectively eliminate CSC subpopulation from pool of cancer cells.

Figure 20:
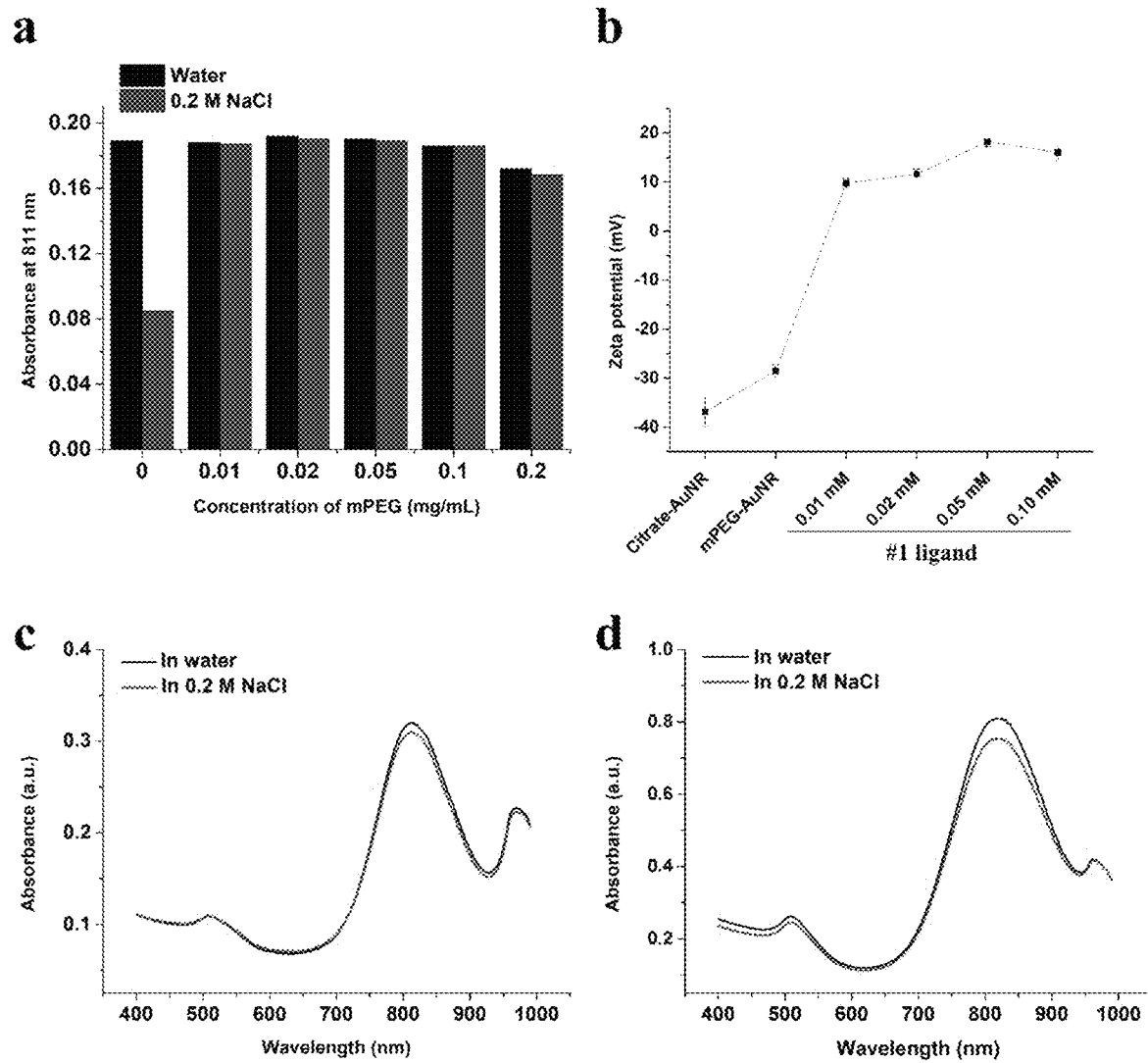
FIGS. 20A-D. Optimization of ligand concentrations and stability of AuNRs in high salt solution.

Preparation and characterization of AuNRs. Because citrate is known to be less toxic to cells and animals than CTAB, citrate-coated AuNR having maximum localized surface plasmon resonance at 808 nm was employed as the starting AuNR (Alkilany et al., 2009). The procedure for the preparation of ligand-conjugated AuNRs is showed in FIG. 19. To improve biocompatibility, the inventors conjugated mPEG on the AuNR surface by ligand exchange. According to the calculation of ligand coverage per gold nanoparticle's surface (Conde et al., 2015), 0.02 mg/mL of mPEG could occupy 30% of 2,590 nm² AuNR's surface. AuNRs modified with varying concentrations of mPEG (from 0.01 to 0.2 mg/mL) were mixed with 0.2 M NaCl to find the optimal concentration for dual conjugations on the surface. Although all AuNRs with different concentrations of mPEG exhibited excellent stability in high salt solution, the inventors have selected 0.02 mg/mL of mPEG to save the space for #1-ligand conjugation (FIG. 20A). Afterward, the inventors conjugated them with CSC targeting #1-ligand. In this study, the inventors synthesized #1 ligand containing thiol in cysteine at N-terminal, allowing a strong interaction with the surface of AuNR. Additionally, the #1 ligand contains spacers between the cysteine and the binding ligand. The presence of spacers could allow for an increase in the accessibility to a binding site. To find optimal concentration of #1-ligand, the inventors added varying amount of #1-ligand to mPEGylated AuNRs. After #1-ligand modification, ζ-potential were change from negative to positive due to the existence of primary amine in #1-ligand (FIG. 20B). Since they obtained highest positive charge from 0.05 mM #1 ligand, the inventors chose this concentration as an optimal condition. The inventors applied this condition to the synthesis of control ligand-conjugated AuNR (Ctrl-AuNR). They observed that resulting AuNRs maintained their stability in high salt solution (FIGS. 20C-D).

Figure 21:
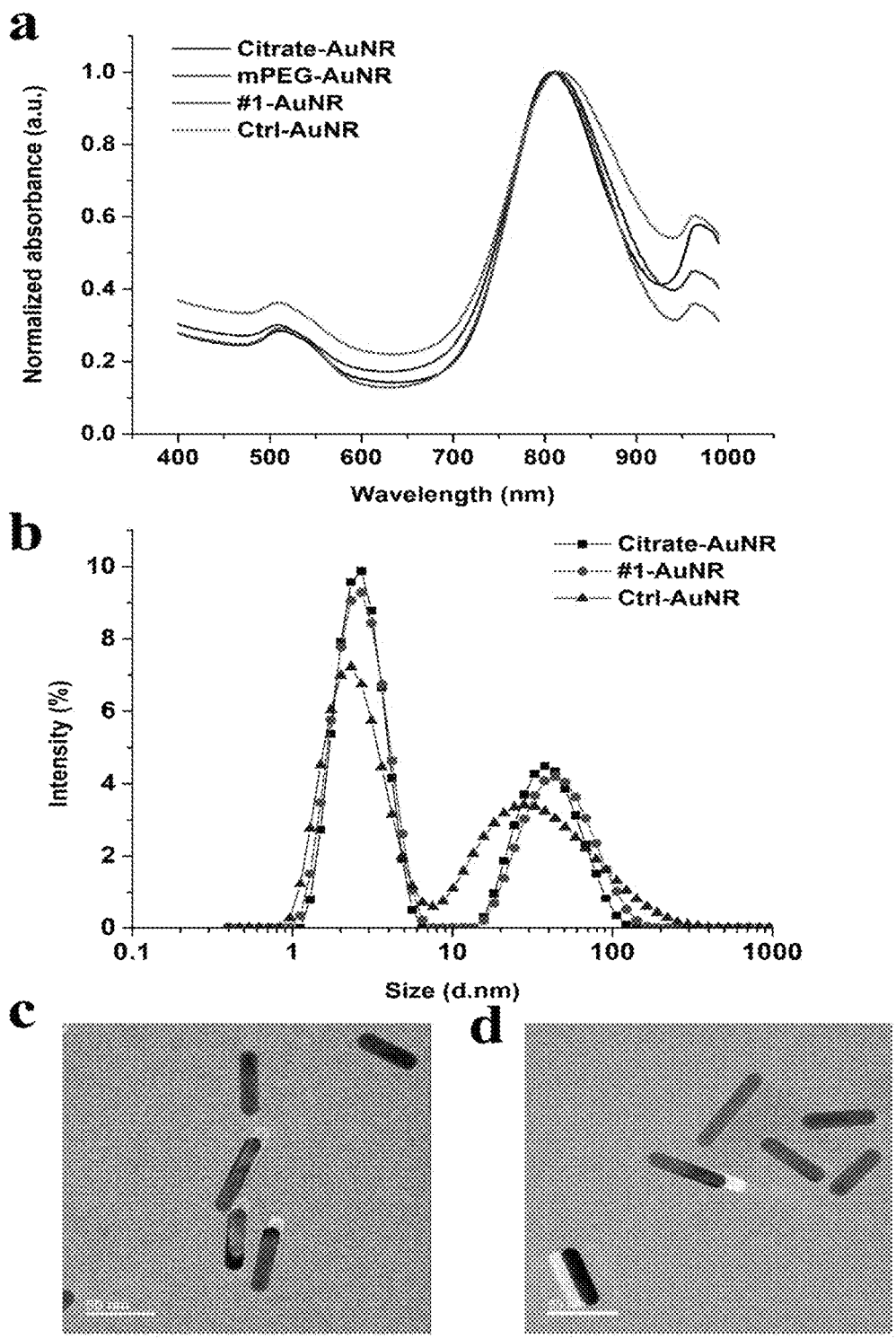
FIGS. 21A-D. Characterization of AuNRs.

The longitudinal surface plasmon resonance red shifed in UV-Vis spectra (FIG. 21A and Table 3), because the ligand conjugation changed the dielectric constant of the surrounding environment of AuNRs (Ali et al., 2017). Compared to #1-ligand, Ctrl-ligand has a lesser number of primary amines resulting in a neutral ζ-potential (Table3). As-prepared AuNRs sustained good stability in aqueous condition (FIG. 21B) and consistent physical shape after modification (FIGS. 21C-D).

Figure 22:
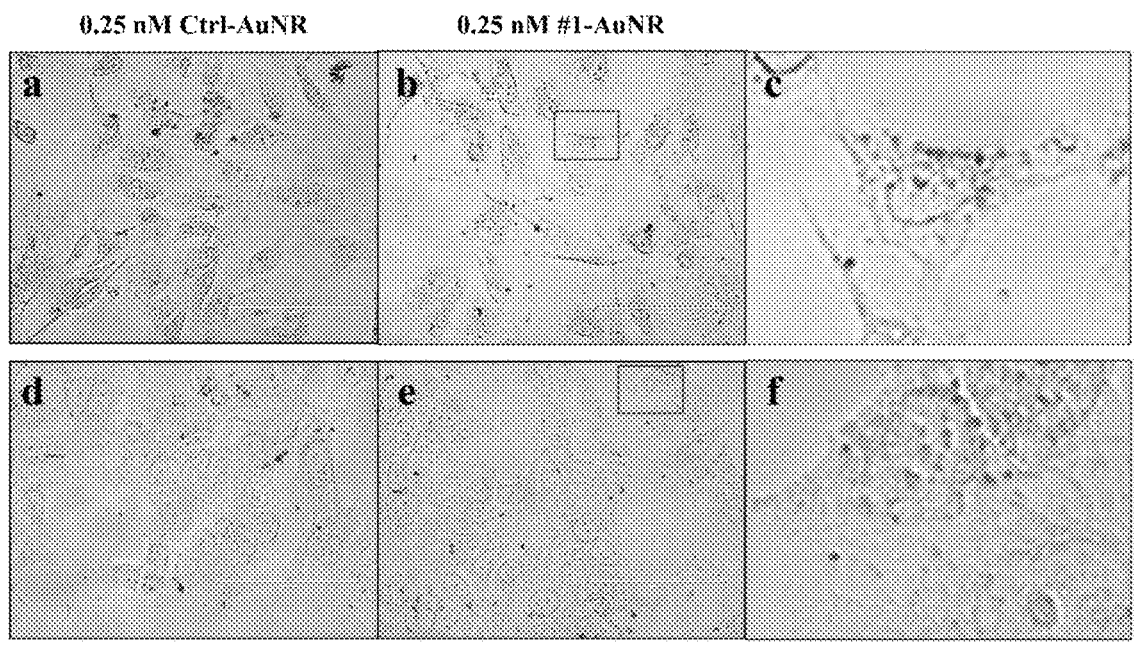
FIGS. 22A-F. Binding distribution of AuNRs in breast cancer cells. MDA-MB-231 (FIGS. 22A-C) and MCF-7 (FIGS. 22D-F). Images of cells treated with 0.25 nM Ctrl-AuNR (FIGS. 22A and 22D) and #1-AuNR (FIGS. 22B and 22E). Red box is zoom-in images of cells treated with #1-AuNR (FIG. 22C and 22F). Blue dot is corresponding the position of AuNR.
Figure 23:
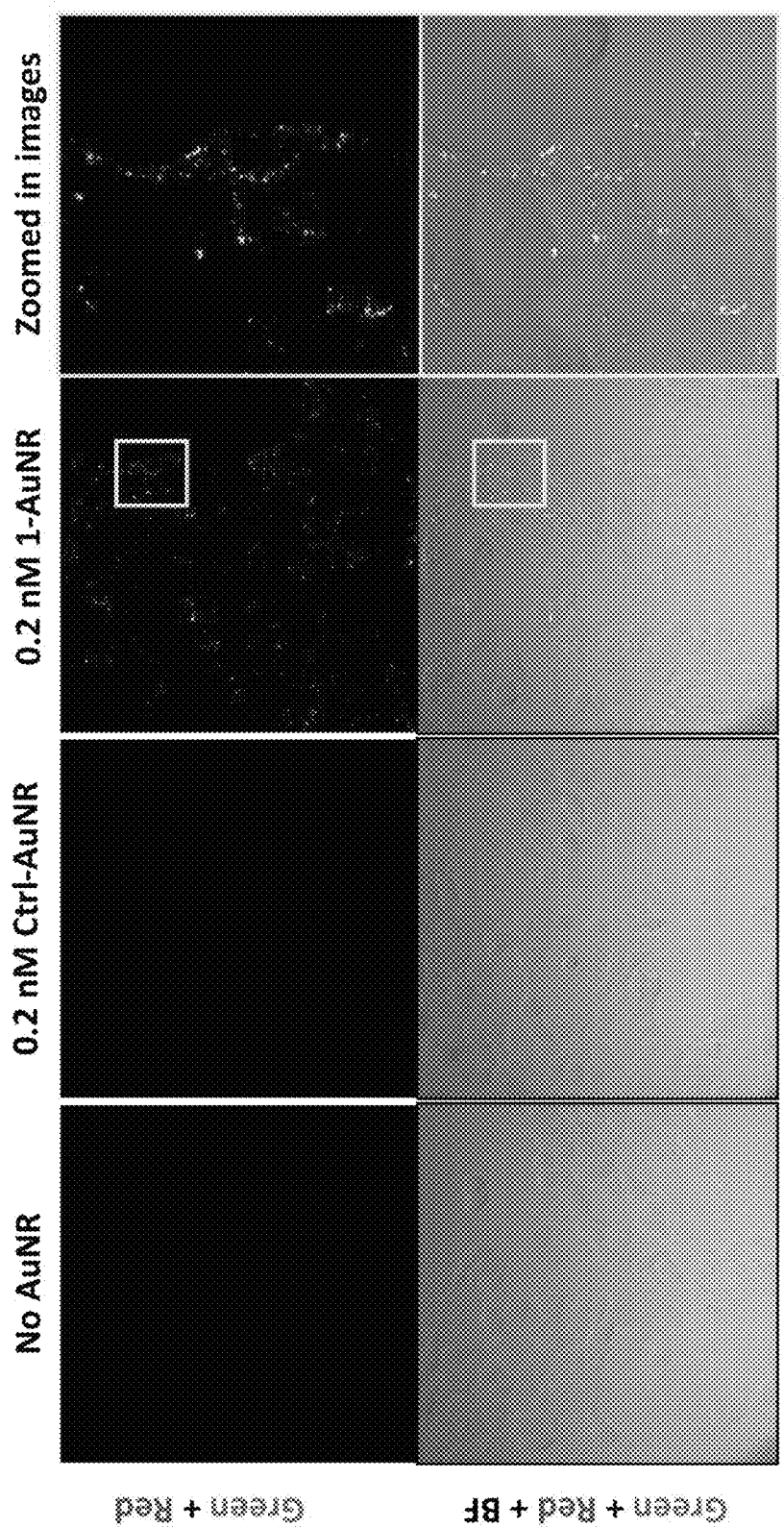
FIG. 23. Intact cell binding distribution of AuNRs in MCF-7. Two-photon luminescence images of cells treated with ctrl, 0.2 nM Ctrl- and #1-AuNRs. Luminescence of AuNR is green, red and yellow colors.

Cell binding study. The binding ability of #1-AuNR was then evaluated in breast cancer cells. Silver enhancement reagent was employed to visualize AuNR in cells. The identical conditions of silver staining were applied to MDA-MB-231 and MCF-7 cell lines. In FIGS. 22B and 22E, the blue dots indicate positions where the AuNRs are present. It observed that MDA-MB-231 and MCF-7 cells treated by #1-AuNR showed blue dots under the microscope. On the contrary, only negligible number of blue dots was observed in the cell treated with the Ctrl-AuNRs. In addition to silver staining, the inventors also conducted two-photon luminescence microscope in MCF-7 by utilizing intrinsic two-photon-induced photoluminescence of AuNR to investigate intact binding distribution of AuNRs. The strong luminescence of AuNR was observed at a power as low as 0.65 mW without autofluorescence, which can be detected above 0.6 mW (data not shown). In accordance with the result of silver enhancement staining, the cells treated by #1-AuNR showed high density of AuNR but not in Ctrl-AuNR (FIG. 23).

Cytotoxicity of AuNR mediated hyperthermia. To examine the photothermal effect of AuNRs on the elimination of CSCs, the inventors employed a nanosecond pulse laser because pulsed radiation generates high heat bubble formation and following cavitation within nano- and microscale causing single cell ablation. According to the literature, a laser illumination at longitudinal plasmon absorption peak between 650 and 950 nm did not result in lethal damage to the cells because the thermal reshaping of AuNRs occurs in 100 ps resulting in which laser pulse will no longer be absorbed by the AuNRs (Ungureanu et al., 2011). On the contrary, green laser, the transverse peak (532 nm), caused the cell-death with moderate change of shape. Based on these results, the inventors decided to utilize a nanosecond pulsed laser at 532 nm at 100 mJ cm$^{-2}$ per pulse to investigate the photothermal treatment of the CSCs mediated by AuNRs.

Figure 24:
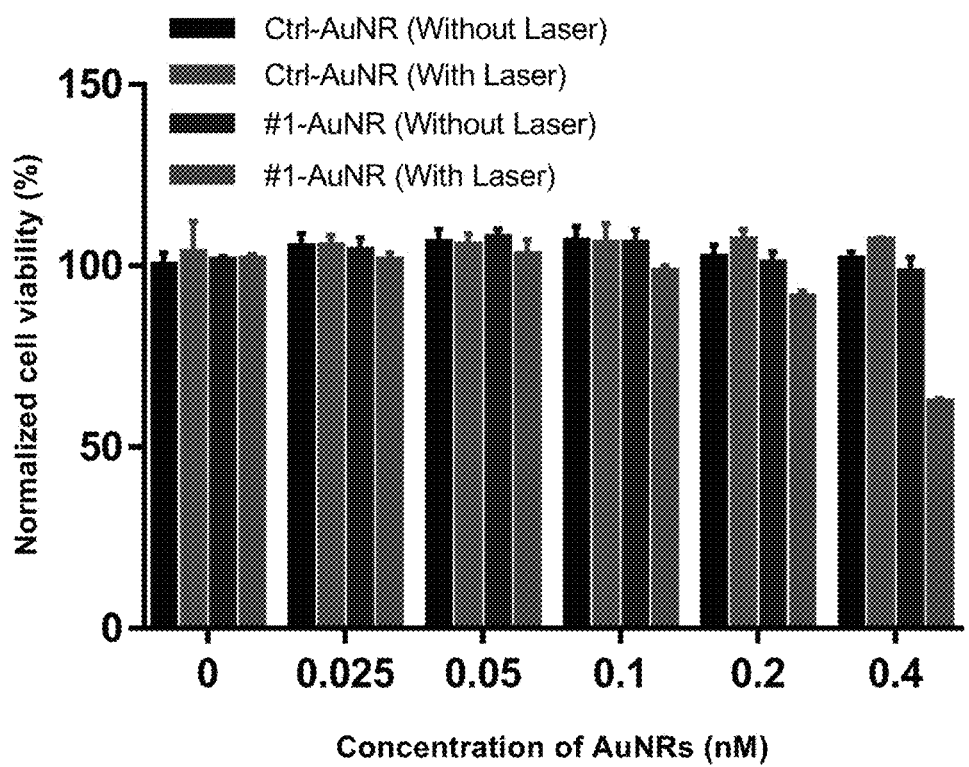
FIG. 24. Effect of the AuNR-mediated hyperthermia on cell viability. MCF-7 cells after 24 h of laser irradiation or non-irradiation. The cells incubated with increasing concentration of AuNRs (0-0.4 nM). Error bars indicate standard deviation of three samples.

The inventors performed MTT assay to examine whether the laser irradiation condition is sufficient to kill the cells. For this, the MCF-7 cells after incubation with different concentrations of #1-AuNR or Ctrl-AuNR (equal to 0.025, 0.05, 0.1, 0.2, and 0.4 nM) were irradiated by nanosecond laser. They also used non-irradiation control groups to examine the cytotoxicity of AuNRs. Irradiated and non-irradiated cells were maintained with fresh medium for 24 hr. The inventors observed that the cells treated by only higher concentrations of #1-AuNRs (0.2 and 0.4 nM) with laser irradiation decreased viable cells by 8.7% and 37.8% respectively, whereas other groups did not show any cell death (FIG. 24). These results are indicating that the condition of laser irradiation is suitable to kill cells and AuNRs themselves do not have a cytotoxicity. Thus, considering that the population of cancer stem cells in MCF-7 cells is around 2%, the cell death of 8% from treatment of 0.2 nM #1-AuNR was determined to be the optimal concentration for the elimination of cancer stem cells with minimized non-specific cell death.

Targeting ability of #1-AuNR to CSCs. Next, the inventors designed the experiment to validate that #1 ligand still maintains CSC targeting activity even on the surface of AuNR. If it does, the AuNRs will be able to bind selectively to the CSC subpopulation than non-CSC subpopulation. For this, the inventors isolated ALDH$^+$ (aldehyde dehydrogenase) subpopulation, which has been identified as cancer stem cells, being capable of self-renewal and of initiating tumor growth (Ginestier et al., 2007). For isolating ALDH$^+$ subpopulation, MCF-7 cells were stained using ALDEL-FUOR™ assay, and ALDH$^+$ subpopulation was sorted via FACS. As shown in FIG. 25B, population of ALDH$^+$ was 1.8% in MCF-7 cells, which is consistent with previous studies (Xu et al., 2014; Yu et al., 2011). To confirm whether sorted subpopulation is cancer stem cell population, the inventors conducted Western blot analysis to see the expression of cancer stem cell markers (FIG. 25B). Levels of KLF4 and Nanog were much higher in ALDH$^+$ subpopulation than whole MCF-7 population and ADLH$^-$ subpopulation, which is also consistent with previous studies (Yu et al., 2011). After sorting the ALDH$^+$ and ALDH" subpopulations, each populations including whole MCF-7 cells (16,000 cell per dishes) were seeded on 35 mm glass bottom dishes and incubated for 12 h at 37° C. Afterward, the cells were incubated with 0.2 nM AuNR for 30 min, and two photon luminescence images of each sample were obtained. The highest density of #1-AuNRs was observed in the ALDH$^+$ cells. In contrast, the ALDH$^-$ cells and whole MCF-7 cells showed very few luminescence signal (FIG. 26A). To quantify the fluorescence signal of each sample, the area occupied with AuNRs was divided by cell surface area in each image using imageJ software, and the values were normalized to the value of whole MCF-7. The ALDH$^+$ cells had more than 9 times the AuNRs than the ALDH$^-$ cells. In the case of whole MCF-7 cells, 2 times more AuNRs were detected than ALDH$^-$ cells, and 5 times less AuNRs were observed than the ALDH$^+$ cells (FIG. 26B). Thus, it is noteworthy that this noble of AuNR can be suitable mediator for photothermal therapy of CSCs.

Figure 28:
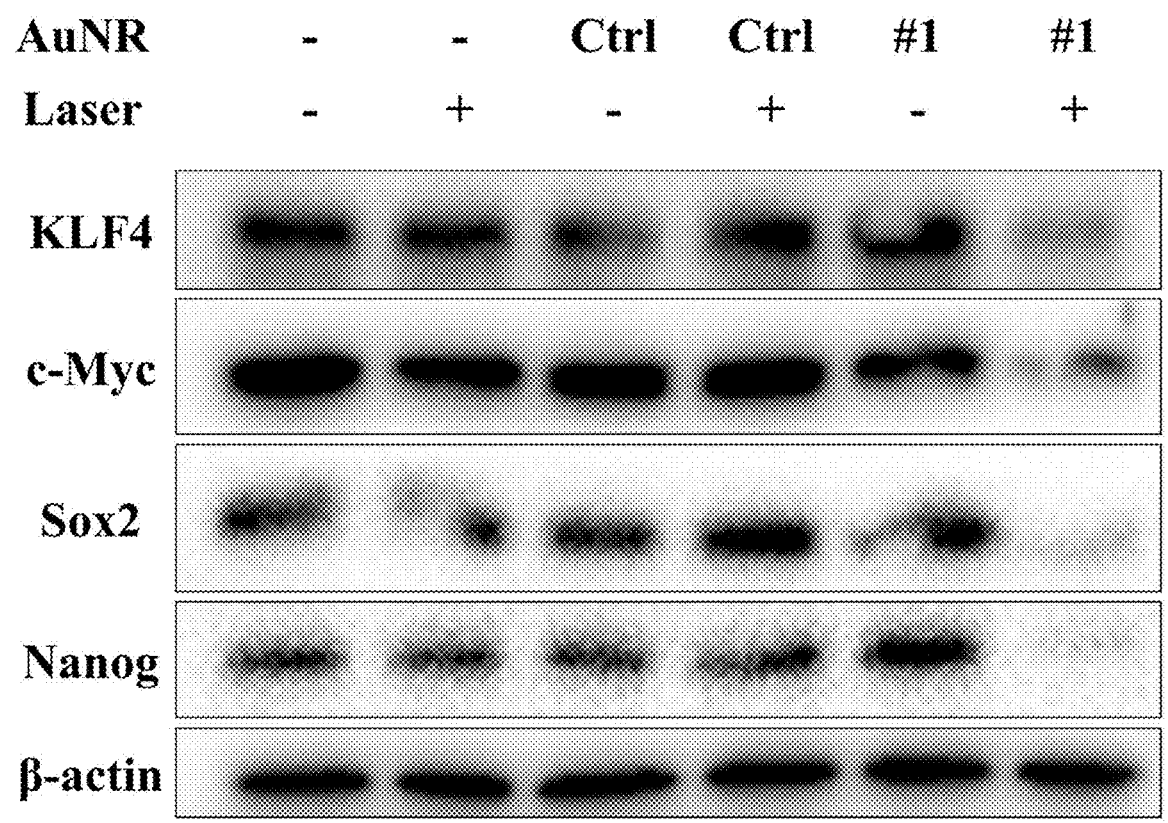
FIG. 28. Effect of AuNR-mediated hyperthermia on expression of stemness-associated transcription factors. Western blot analysis of CSC-associated transcription factors in MCF-7 cells treated with or without AuNRs and with or without laser irradiation.

Effect of the AuNR-mediated hyperthermia on CSC. To evaluate the hyperthermia effect of AuNR on CSCs, the inventors conducted in situ ALDELFUOR™ assay for visualizing CSCs in six different groups (cells only, cells-laser, Ctrl-AuNR, Ctrl-AuNR-laser, #1-AuNR, #1-AuNR-laser). As shown in FIG. 27A, the validity of CSCs labeling by ALDEFLUOR™ assay kit was confirmed by observing diminished green fluorescence upon treatment of DEAB. Fluorescence images in FIG. 27A demonstrated that Ctrl-AuNR or laser irradiation itself does not affect the fate of CSCs, whereas following treatment of #1-AuNRs and laser irradiation, the CSCs population in the cells was dramatically decreased versus the control groups. To quantify the number of ALDH⁺ cells, the inventors counted ALDH⁺ cells and DAPI-stained cells, and then the inventors divided ADLH⁺ cell by total number of cells in each image. The ALDH⁺ cell population is around 4% in the control group, which are higher than the result from FACS analysis because FACS excludes small particles that cannot pass the threshold such as cell debris, cell doublets, and dead cells. The inventors observed that the ALDH cells were decreased by >50% in #1-AuNR-laser group versus control group (FIG. 27B). They also carried out Western blot analysis to assess CSC associated transcription factors, KLF4, c-Myc, Nanog and Sox2 after treatments. The results showing in FIG. 28 are very correlated with the result of ALDEFLUOR™ assay. Taken together, the results indicate that #1-AuNR-mediated photo-induced hyperthermia affects the fate of CSCs.

Conclusions. In summary, the inventors have successfully designed and fabricated cancer stem cell-targeting AuNR by conjugating the #1 ligand identified from high-throughput screening. The resulting AuNR possess high selectivity toward CSCs population and the capacity to serve as mediator photothermal treatment upon irradiation of nanosecond laser. These results demonstrate that the #1-AuNR selectively binds to ALDH⁺ subpopulation, which is considered as CSCs population and upon the laser irradiation the heat generated from the AuNR diminished CSC population. Furthermore, levels of proteins that closely related with stemness of cancer were significantly decreased after #1-AuNR mediated heat treatment. Taken together, this study introduced a novel therapeutic potential of the AuNR-mediated hyperthermia treatment in elimination of breast CSCs. The inventors believed that in combination with conventional chemo- or radio-therapy, this novel nanotherapeutic system could lead to significant reduction of metastasis, recurrence, and resistance of cancer.

TABLE 3

Summary of wavelength at maximum OD and ζ-potential with different surface ligands

| AuNRs | Wavelength at Maximum OD (nm) | Zeta potential (mV) |
| --- | --- | --- |
| Citrate-AuNRs | 808 | −36.87 ± 2.90 |
| mPEG-AuNRs | 811 | −28.53 ± 1.27 |
| #1-AuNRs | 812 | 11.37 ± 1.45 |
| Con-AuNRs | 815 | 1.30 ± 0.62 |

All of the methods and apparatus disclosed and claimed herein can be made and executed without undue experimentation in light of the present disclosure. While the compositions and methods of this disclosure have been described in terms of particular embodiments, it will be apparent to those of skill in the art that variations may be applied to the methods and apparatus and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

P. G. Alluri, M. M. Reddy, K. Bachhawat-Sikder, H. J. Olivos, T. Kodadek, *Journal of the American Chemical Society* 2003, 125, 13995-14004

A. Aditya, T. Kodadek, *ACS combinatorial science* 2012, 14, 164-169.

A. M. Gonzalez-Angulo, F. Morales-Vasquez, G. N. Hortobagyi, *Advances in experimental medicine and biology* 2007, 608, 1-22.

A. M. Brewster, G. N. Hortobagyi, K. R. Broglio, S. W. Kau, C. A. Santa-Maria, B. Arun, A. U. Buzdar, D. J. Booser, V. Valero, M. Bondy, F. J. Esteva, *Journal of the National Cancer Institute* 2008, 100, 1179-1183.

J. E. Dick, *Blood* 2008, 112, 4793-4807.

H. Clevers, *Nature medicine* 2011, 17, 313-319.

T. Reya, S. J. Morrison, M. F. Clarke, I. L. Weissman, *Nature* 2001, 414, 105-111.

C. T. Jordan, M. L. Guzman, M. Noble, *N. Engl. J. Med.* 2006, 355, 1253-1261.

D. R. Pattabiraman, R. A. Weinberg, *Nature reviews. Drug discovery* 2014, 13, 497-512.

M. Al-Hajj, M. S. Wicha, A. Benito-Hernandez, S. J. Morrison, M. F. Clarke, *Proceedings of the National Academy of Sciences of the United States of America* 2003, 100, 3983-3988.

K. S. Lam, M. Lebl, V. Krchnak, *Chemical reviews* 1997, 97, 411-448.

J. Lee, M. M. Reddy, T. Kodadek, *Chemical science* 2010, 1, 48-54.

T. M. Phillips, W. H. McBride, F. Pajonk, *Journal of the National Cancer Institute* 2006, 98, 1777-1785.

L. Burdine, T. G. Gillette, H. J. Lin, T. Kodadek, *J Am Chem Soc* 2004, 126, 11442-11443.

C. Ginestier, M. H. Hur, E. Charafe-Jauffret, F. Monville, J. Dutcher, M. Brown, J. Jacquemier, P. Viens, C. G. Kleer, S. Liu, A. Schott, D. Hayes, D. Birnbaum, M. S. Wicha, G. Dontu, *Cell stem cell* 2007, 1, 555-567.

Y. Zhong, S. Shen, Y. Zhou, F. Mao, J. Guan, Y. Lin, Y. Xu, Q. Sun, *Medical oncology (Northwood, London, England)* 2014, 31, 864.

K. R. Bauer, M. Brown, R. D. Cress, C. A. Parise, V. Caggiano, *Cancer* 2007, 109, 1721-1728.

E. A. Rakha, S. E. Elsheikh, M. A. Aleskandarany, H. O. Habashi, A. R. Green, D. G. Powe, M. E. El-Sayed, A. Benhasouna, J. S. Brunet, L. A. Akslen, A. J. Evans, R. Blarney, J. S. Reis-Filho, W. D. Foulkes, I. O. Ellis, *Clinical cancer research: an official journal of the American Association for Cancer Research* 2009, 15, 2302-2310.

R. Dent, M. Trudeau, K. I. Pritchard, W. M. Hanna, H. K. Kahn, C. A. Sawka, L. A. Lickley, E. Rawlinson, P. Sun, S. A. Narod, *Clin. Cancer Res.* 2007, 13, 4429-4434.

J. Choi, W.-H. Jung, J. S. Koo, *Histology and histopathology* 2012, 27, 1481-1493.

B. D. Lehmann, J. A. Bauer, X. Chen, M. E. Sanders, A. B. Chakravarthy, Y. Shyr, J. A. Pietenpol, *The Journal of clinical investigation* 2011, 121, 2750-2767.

M. O. Idowu, M. Kmieciak, C. Dumur, R. S. Burton, M. M. Grimes, C. N. Powers, M. H. Manjili, *Human pathology* 2012, 43, 364-373.

A. Kreso, J. E. Dick, *Cell Stem Cell* 2014, 14, 275-291.

D. Kong, Y. Li, Z. Wang, F. H. Sarkar, *Cancers* 2011, 3, 716-729.

S. A. Mani, W. Guo, M. J. Liao, E. N. Eaton, A. Ayyanan, A. Y. Zhou, M. Brooks, F. Reinhard, C. C. Zhang, M. Shipitsin, L. L. Campbell, K. Polyak, C. Brisken, J. Yang, R. A. Weinberg, *Cell* 2008, 133, 704-715.

N. Yao, W. Xiao, X. Wang, J. Marik, S. H. Park, Y. Takada, K. S. Lam, *J. Med. Chem.* 2009, 52, 126-133.

J. M. Matharage, J. D. Minna, R. A. Brekken, D. G. Udugamasooriya, *ACS Chem. Biol.* 2015, 10, 2891-2899.

D. G. Udugamasooriya, S. P. Dineen, R. A. Brekken, T. Kodadek, *Journal of the American Chemical Society* 2008, 130, 5744-5752.

D. Abetov, Z. Mustapova, T. Saliev, D. Bulanin, K. Batyrbekov, C. P. Gilman, *Stem Cell Rev* 2015, 11, 909-918.

Sancho, P.; Burgos-Ramos, E.; Tavera, A.; Kheir, T. B.; Jagust, P.; Schoenhals, M.; Barneda, D.; Sellers, K.; Campos-Olivas, R.; Grafia, O.; Viera C. R.; Yuneva, M.; Sainz, B. Jr.; Heeschen, C. Cell Metab. 2015, 22, 590-605.

Borah, A.; Raveendran, S.; Rochani, A.; Maekawa, T.; Kumar, D. S. *Oncogenesis* 2015, 4, 1-11.

Ye, X.; Tam, W. L.; Shibue, T.; Kaygusuz, Y.; Reinhardt, F.; Ng Eaton, E.; Weinberg, R. A. *Nature* 2015, 525, 256-260.

Bonnet, D.; Dick, J. E. *Nat. Med.* 1997, 3, 730-738.

Al-Hajj, M.; Wicha, M. S.; Benito-Hernandez, A.; Morrison, S. J.; Clarke, M. F. *Proc. Natl. Acad. Sci. U.S.A.* 2003, 100, 3983-3988.

Dontu, G.; Abdallah, W. M.; Foley, J. M.; Jackson, K. W.; Clarke, M. F.; Kawamura, M. J.; Wicha, M. S. *Genes Dev.* 2003, 17, 1253-1270.

Ginestier, C.; Hur, M. H.; Charafe-Jauffret, E.; Monville, F.; Dutcher, J.; Brown, M.; Jacquemier, J.; Viens, P.; Kleer, C. G.; Liu, S.; Schott, A.; Hayes, D.; Birnbaum, D.; Wicha, M. S.; Dontu, G. *Cell Stem Cell* 2007, 1, 555-567.

Fang, D.; Nguyen, T. K.; Leishear, K.; Finko, R.; Kulp, A. N.; Hotz, S.; Van Belle, P. A.; Xu, X.; Elder, D. E.; Herlyn, M. *Cancer Research* 2005, 65 (20), 9328-9337.

Collins, A. T.; Berry, P. A.; Hyde, C.; Stower, M. J.; Maitland, N. J. *Cancer Research* 2005, 65, 10946-10951.

Wilson, R. J.; Thomas, C. D.; Fox, R.; Roy, D. B.; Kunin, W. E. *Nature* 2004, 432, 393-396.

O'Brien, C. A.; Pollett, A.; Gallinger, S.; Dick, J. E. *Nature* 2006, 445, 106-110.

Li, C.; Heidt, D. G.; Dalerba, P.; Burant, C. F.; Zhang, L.; Adsay, V.; Wicha, M.; Clarke, M. F.; Simeone, D. M. *Cancer Research* 2007, 67, 1030-1037.

Prince, M. E.; Sivanandan, R.; Kaczorowski, A.; Wolf, G. T.; Kaplan, M. J.; Dalerba, P.; Weissman, I. L.; Clarke, M. F.; Ailles, L. E. *Proc. Natl. Acad. Sci. U.S.A.* 2007, 104, 973-978.

Skvortsov, S.; Debbage, P.; Lukas, P.; Skvortsova, I. *Seminars in Cancer Biology* 2015, 31, 36-42.

Maugeri-Sacca, M.; Bartucci, M.; De Maria, R. *Molecular Cancer Therapeutics* 2012, 11, 1627-1636.

Tothova, Z.; Kollipara, R.; Huntly, B. J.; Lee, B. H.; Castrillon, D. H.; Cullen, D. E.; McDowell, E. P.; Lazo-Kallanian, S.; Williams, I. R.; Sears, C.; Armstrong, S. A.; Passegue, E.; DePinho, R. A.; Gilliland, D. G. *Cell* 2007, 128, 325-339.

Ryall, J. G.; Dell'Orso, S.; Derfoul, A.; Juan, A.; Zare, H.; Feng, X.; Clermont, D.; Koulnis, M.; Gutierrez-Cruz, G.; Fulco, M.; Sartorelli, V. *Stem Cell* 2015, 16, 171-183.

Simsek, T.; Kocabas, F.; Zheng, J.; DeBerardinis, R. J.; Mahmoud, A. I.; Olson, E. N.; Schneider, J. W.; Zhang, C. C.; Sadek, H. A. *Stem Cell* 2010, 7, 380-390.

Rodriguez-Colman, M. J.; Schewe, M.; Meerlo, M.; Stigter, E.; Gerrits, J.; Pras-Raves, M.; Sacchetti, A.; Hornsveld, M.; Oost, K. C.; Snippert, H. J.; Verhoeven-Duif, N.; Fodde, R.; Burgering, B. M. T. *Nature* 2017, 543, 424-427.

Beerling, E.; Seinstra, D.; de Wit, E.; Kester, L.; van der Velden, D.; Maynard, C.; Schafer, R.; van Diest, P.; Voest, E.; van Oudenaarden, A.; Vrisekoop, N.; van Rheenen, *J. Cell Reports* 2016, 14, 2281-2288.

Spranger, S.; Bao, R.; Gajewski, T. F. *Nature* 2015, 523, 231-235.

Tan, I.; Storelvmo, T.; Zelinka, M. D. *Science* 2016, 352, 224-227.

Driessens, G.; Beck, B.; Caauwe, A.; Simons, B. D.; Blanpain, C. *Nature* 2012, 488, 527-530.

Boiko, A. D.; Razorenova, O. V.; van de Rijn, M.; Swetter, S. M.; Johnson, D. L.; Ly, D. P.; Butler, P. D.; Yang, G. P.; Joshua, B.; Kaplan, M. J.; Longaker, M. T.; Weissman, I. L. *Nature* 2010, 466, 133-137.

Pascual, G.; Avgustinova, A.; Mejetta, S.; Martin, M.; Castellanos, A.; Attolini, C. S.-O.; Berenguer, A.; Prats, N.; Toll, A.; Hueto, J. A.; Bescos, C.; Di Croce, L.; Benitah, S. A. *Nature* 2017, 541, 41-45.

de Goeij, B. E.; Lambert, J. M. *Curr. Opin. Immunol.* 2016, 40, 14-23.

Mullard, A. *Nat. Rev. Drug Discov.* 2013, 12, 329-332.

Junttila, M. R.; Mao, W.; Wang, X.; Wang, B.-E.; Pham, T.; Flygare, J.; Yu, S.-F.; Yee, S.; Goldenberg, D.; Fields, C.; Eastham-Anderson, J.; Singh, M.; Vij, R.; Hongo, J.-A.; Firestein, R.; Schutten, M.; Flagella, K.; Polakis, P.; Polson, A. G. *Sci. Transl. Med.* 2015, 7, 314ra186.

Roesch, A.; Vultur, A.; Bogeski, I.; Wang, H.; Zimmermann, K. M.; Speicher, D.; Korbel, C.; Laschke, M. W.; Gimotty, P. A.; Philipp, S. E.; Krause, E.; Patzold, S.; Villanueva, J.; Krepler, C.; Fukunaga-Kalabis, M.; Hoth, M.; Bastian, B. C.; Vogt, T.; Herlyn, M. *Cancer Cell* 2013, 23, 811-825.

Viale, A.; Pettazzoni, P.; Lyssiotis, C. A.; Ying, H.; Sanchez, N.; Marchesini, M.; Carugo, A.; Green, T.; Seth, S.; Giuliani, V.; Kost-Alimova, M.; Muller, F.; Colla, S.; Nezi, L.; Genovese, G.; Deem, A. K.; Kapoor, A.; Yao, W.; Brunetto, E.; Kang, Y.; Yuan, M.; Asara, J. M.; Wang, Y. A.; Heffernan, T. P.; Kimmelman, A. C.; Wang, H.; Fleming, J. B.; Cantley, L. C.; DePinho, R. A.; Draetta, G. F. *Nature* 2014, 514, 628-632.

Takebe, N.; Miele, L.; Harris, P. J.; Jeong, W.; Bando, H.; Kahn, M.; Yang, S. X.; Ivy, S. P. *Nat. Rev. Clin. Oncol.* 2015, 12, 1-20.

Saunders, L. R.; Bankovich, A. J.; Anderson, W. C.; Aujay, M. A.; Bheddah, S.; Black, K.; Desai, R.; Escarpe, P. A.; Hampl, J.; Laysang, A.; Liu, D.; Lopez-Molina, J.; Milton, M.; Park, A.; Pysz, M. A.; Shao, H.; Slingerland, B.; Torgov, M.; Williams, S. A.; Foord, O.; Howard, P.; Jassem, J.; Badzio, A.; Czapiewski, P.; Harpole, D. H.; Dowlati, A.; Massion, P. P.; Travis, W. D.; Pietanza, M. C.; Poirier, J. T.; Rudin, C. M.; Stull, R. A.; Dylla, S. J. *Sci. Transl. Med.* 2015, 7, 302ra136-302ra136.

Hoff, Von, D. D.; LoRusso, P. M.; Rudin, C. M.; Reddy, J. C.; Yauch, R. L.; Tibes, R.; Weiss, G. J.; Borad, M. J.; Hann, C. L.; Brahmer, J. R.; Mackey, H. M.; Lum, B. L.; Darbonne, W. C.; Marsters, J. C., Jr.; de Sauvage, F. J.; Low, J. *N. Engl. J. Med.* 2009, 361, 1164-1172.

Frank, N. Y.; Schatton, T.; Frank, M. H. *J. Clin. Invest.* 2010, 120, 41-50.

Ramos, E. K.; Hoffmann, A. D.; Gerson, S. L.; Liu, H. *Trends Cancer* 2017, 3, 1-17.

Qin, Z.; Bischof, J. C. *Chem. Soc. Rev.* 2012, 41, 1191-1217.

Rasulov, A. O.; Gordeyev, S. S.; Barsukov, Y. A.; Tkachev, S. I.; Malikhov, A. G.; Balyasnikova, S. S.; Fedyanin, M. Y. *Int. J. Hyperthermia* 2016, 33, 465-470.

Dewhirst, M. W.; Vujaskovic, Z.; Jones, E.; Thrall, D. *Int. J. Hyperthermia* 2011, 21, 779-790.

Pantano, P.; Harrison, C. D.; Poulose, J.; UrrabazoJr, D.; Norman, T. Q.; Braun, E. I.; Draper, R. K.; Overzet, L. J. *Appl. Spectrosc. Rev.* 2017, 0, 1-16.

van Valenberg, H.; Colombo, R.; Witjes, F. *Int. J. Hyperthermia* 2016, 32, 351-362.

Hurwitz, M. D.; Kaplan, I. D.; Hansen, J. L.; Prokopios-Davos, S.; Topulos, G. P.; Wishnow, K.; Manola, J.; Bornstein, B. A.; Hynynen, K. Int. J. Hyperthermia 2009, 21, 649-656.

Huang, S.-C.; Huang, Y.-Y.; PhD, K.-W. L.; PhD, M. K. M.; MD, K.-H. C. *Int. J. Radiat. Oncol. Biol. Phys.* 2018, 100, 78-87.

Overgaard, J.; Gonzalez Gonzalez, D.; Hulshof, M. C. C. H.; Arcangeli, G.; Dahl, O.; Mella, O.; Bentzen, S. M. *Int. J. Hyperthermia* 2009, 25, 323-334.

Hurwitz, M. D.; Hansen, J. L.; Prokopios-Davos, S.; Manola, J.; Wang, Q.; Bornstein, B. A.; Hynynen, K.; Kaplan, I. D. *Cancer* 2010, 117, 510-516.

Datta, N. R.; Rogers, S.; Klingbiel, D.; Gomez, S.; Puric, E.; Bodis, S. *Int. J. Hyperthermia* 2016, 32, 809-821.

Zwirner, Z. et al., *Int. J. Hyperthermia* 2019, 34, 455-460.

Harima, Y.; Ohguri, T.; Imada, H.; Sakurai, H.; Ohno, T.; Hiraki, Y.; Tuji, K.; Tanaka, M.; Terashima, H. *Int. J. Hyperthermia* 2016, 32, 801-808.

Refaat, T.; Sachdev, S.; Sathiaseelan, V.; Helenowski, I.; Abdelmoneim, S.; Pierce, M. C.; Woloschak, G.; Small, W., Jr; Mittal, B.; Kiel, K. D. *The Breast* 2015, 24, 418-425.

Mantso, T.; Vasileiadis, S.; Anestopoulos, I.; Voulgaridou, G. P.; Lampri, E.; Botaitis, S.; Kontomanolis, E. N.; Simopoulos, C.; Goussetis, G.; FRANCO, R.; et al. *Sci Rep* 2018, 8, 1-16.

Hoopes, P. J.; Wagner, R. J.; Duval, K.; Kang, K.; Gladstone, D. J.; Moodie, K. L.; Crary-Burney, M.; Ariaspulido, H.; Veliz, F. A.; Steinmetz, N. F.; Fiering, S. N. *Mol. Pharmaceutics* 2018, 15, 3717-3722.

ten Hove, I; M, F.; van Rhoon G C; M, P. M. *Int. J. Hyperthermia* 2019, 34, 994-1001.

Mu, C.; Wu, X.; Zhou, X.; Wolfram, J.; Shen, J.; Zhang, D.; Mai, J.; Xia, X.; Holder, A. M.; Ferrari, M.; Liu, X.; Shen, H. *Clin. Cancer Res.* 2018, 24, 4900-4912.

Ozhinsky, E.; Salgaonkar, V. A.; Diederich, C. J.; Rieke, V. J. *Ther. Ultrasound* 2018, 6, 1-10.

Dubois, M. F.; Hovanessian, A. G.; Bensaude, O. *J. Biol. Chem.* 1991, 266, 9707-9711.

Stein, U.; Jürchott, K.; Walther, W.; Bergmann, S.; Schlag, P. M.; Royer, H. D. *J. Biol. Chem.* 2001, 276, 28562-28569.

Oei, A. L.; Vriend, L. E. M.; Crezee, J.; Franken, N. A. P.; Krawczyk, P. M. *Radiat. Oncol.* 2015, 10, 1-13.

Pelicci, P. G.; Dalton, P.; Orecchia, R. *Breast Cancer Res.* 2011, 13, 105-2.

Carnero, A.; Lleonart, M. *Inside the Cell* 2015, 1, 96-105.

Zhang, Z.; Wang, J.; Chen, C. *Adv. Mater.* 2013, 25, 3869-3880.

Li, J.-L.; Bao, H.-C.; Hou, X.-L.; Sun, L.; Wang, X.-G.; Gu, M. *Angew. Chem. Int. Ed.* 2012, 51, 1830-1834.

Jin, G.; He, R.; Liu, Q.; Dong, Y.; Lin, M.; Li, W.; Xu, F. *ACS Appl. Mater. Interfaces* 2018, 10, 10634-10646.

Yao, H.-J.; Zhang, Y.-G.; Sun, L. *Biomaterials* 2014, 35, 9208-9223.

Zhang, L.; Su, H.; Cai, J.; Cheng, D.; Ma, Y.; Zhang, J.; Zhou, C.; Liu, S.; Shi, H.; Zhang, Y.; Zhang, C. *ACS Nano* 2016, 10, 10404-10417.

Xu, Y.; Wang, J.; Li, X.; Liu, Y.; Dai, L.; Wu, X.; Chen, C. *Biomaterials* 2014, 35, 4667-4677.

Pérez-Hernandez, M.; del Pino, P.; Mitchell, S. G.; Moros, M.; Stepien, G.; Pelaz, B.; Parak, W. J.; Galvez, E. M.; Pardo, J.; la Fuente, de, J. M. *ACS Nano* 2015, 9, 52-61.

Sun, T.; Wang, Y.; Wang, Y.; Xu, J.; Zhao, X.; Vangveravong, S.; Mach, R. H.; Xia, Y. *Adv. Healthcare Mater.* 2014, 3, 1283-1291.

Sun, T.-M.; Wang, Y.-C.; Wang, F.; Du, J.-Z.; Mao, C.-Q.; Sun, C.-Y.; Tang, R.-Z.; Liu, Y.; Zhu, J.; Zhu, Y.-H.; Yang, X.-Z.; Wang, *J. Biomaterials* 2014, 35, 836-845.

Atkinson, R. L.; Zhang, M.; Diagaradjane, P.; Peddibhotla, S.; Contreras, A.; Hilsenbeck, S. G.; Woodward, W. A.; Krishnan, S.; Chang, J. C.; Rosen, J. M. *Sci. Transl. Med.* 2010, 2, 55ra79-55ra79.

Chen, L.; Long, C.; Tran, K. A. M.; Lee, J. *Chem. Eur. 1* 2018, 24, 3694-3698.

Alkilany, A. M.; Nagaria, P. K.; Hexel, C. R.; Shaw, T. J.; Murphy, C. J.; Wyatt, M. D. *Small* 2009, 5, 701-708.

Conde, J.; Oliva, N.; Artzi, N. *Proc. Natl. Acad. Sci. U.S.A.* 2015, 112, E1278-E1287.

Ali, M. R. K.; Wu, Y.; Tang, Y.; Xiao, H.; Chen, K.; Han, T.; Fang, N.; Wu, R.; El-Sayed, M. A. *Proc. Natl. Acad. Sci. U.S.A.* 2017, 114, E5655-E5663.

Ungureanu, C.; Kroes, R.; Petersen, W.; Groothuis, T. A. M.; Ungureanu, F.; Janssen, H.; van Leeuwen, F. W. B.; Kooyman, R. P. H.; Manohar, S.; van Leeuwen, T. G. *Nano Lett.* 2011, 11, 1887-1894.

Yu, F.; Li, J.; Chen, H.; Fu, J.; Ray, S.; Huang, S.; Zheng, H.; Ai, W. *Oncogene* 2011, 30, 2161-2172.

U.S. Pat. No. 5,739,169
U.S. Pat. No. 5,801,005
U.S. Pat. No. 5,824,311
U.S. Pat. No. 5,830,880
U.S. Pat. No. 5,846,945
Arap et al., *Cancer Res.*, 55(6):1351-1354, 1995.
Austin-Ward and Villaseca, *Revista Medica de Chile*, 126(7):838-845, 1998.
Bakhshi et al., *Cell*, 41(3):899-906, 1985.
Bukowski et al., *Clinical Cancer Res.*, 4(10):2337-2347, 1998.
Caldas et al., *Cancer Res.*, 54:3568-3573, 1994.
Cheng et al., *Cancer Res.*, 54(21):5547-5551, 1994.
Christodoulides et al., *Microbiology*, 144(Pt 11):3027-3037, 1998.
Cleary and Sklar, *Proc. Natl. Acad. Sci. USA*, 82(21):7439-7443, 1985.
Cleary et al., *J. Exp. Med.*, 164(1):315-320, 1986.
Davidson et al., *J. Immunother* 21(5):389-398, 1998.
Hanibuchi et al., *Int. J. Cancer*, 78(4):480-485, 1998.
Hellstrand et al., *Acta Oncologica*, 37(4):347-353, 1998.
Hui and Hashimoto, *Infection Immun.*, 66(11):5329-5336, 1998.
Hussussian et al., *Nat. Genet.*, 8(1):15-21, 1994.
Ju et al., *Gene Ther.*, 7(19):1672-1679, 2000.
Kamb et al., *Nat. Genet.*, 8(1):23-26, 1994.
Kamb et al., *Science*, 2674:436-440, 1994.
Kerr et al., *Br. J. Cancer*, 26(4):239-257, 1972.
Lin et al., *Intl. J. Cancer*, 123:372-379, 2008.
Mitchell et al., *Ann. NY Acad. Sci.*, 690:153-166, 1993.
Mitchell et al., *J. Clin. Oncol.*, 8(5):856-869, 1990.
Mori et al., *Cancer Res.*, 54(13):3396-3397, 1994.
Morton et al., *Arch. Surg.*, 127:392-399, 1992.
Nobori et al., *Nature (London)*, 368:753-756, 1995.
Okamoto et al., *Proc. Natl. Acad. Sci. USA*, 91(23):11045-11049, 1994.
Orlow et al., *Cancer Res*, 54(11):2848-2851, 1994.
Pietras et al., *Oncogene*, 17(17):2235-2249, 1998.

Qin et al., *Proc. Natl. Acad. Sci. USA,* 95(24):14411-14416, 1998.
Rakha and Ellis, *Pathology,* 41:40-47, 2009.
Ravindranath and Morton, *Intern. Rev. Immunol.,* 7: 303-329, 1991.
Rosenberg et al., *Ann. Surg.* 210(4):474-548, 1989.
Rosenberg et al., *N. Engl. J. Med.,* 319:1676, 1988.
Serrano et al., *Nature,* 366:704-707, 1993.
Serrano et al., *Science,* 267(5195):249-252, 1995.
Tsujimoto and Croce, *Proc. Natl. Acad. Sci. USA,* 83(14): 5214-5218, 1986.
Tsujimoto et al., *Nature,* 315:340-343, 1985.

What is claimed:

1. A compound having the formula:

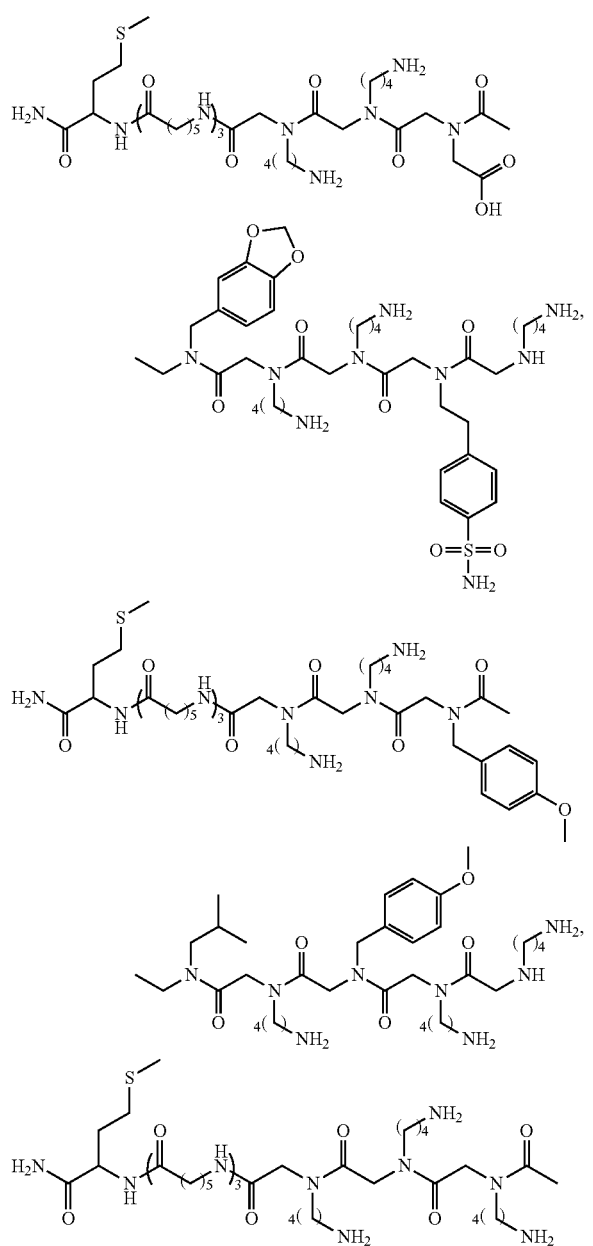
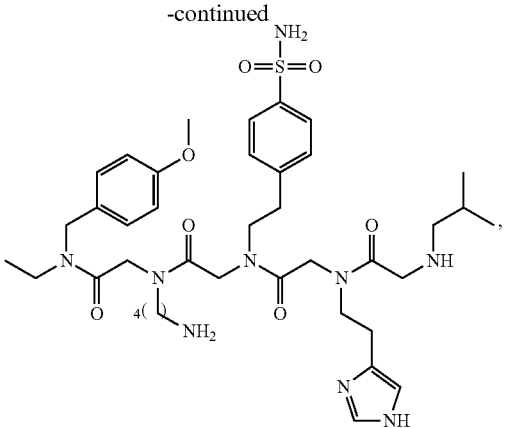
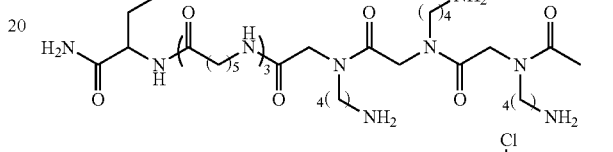
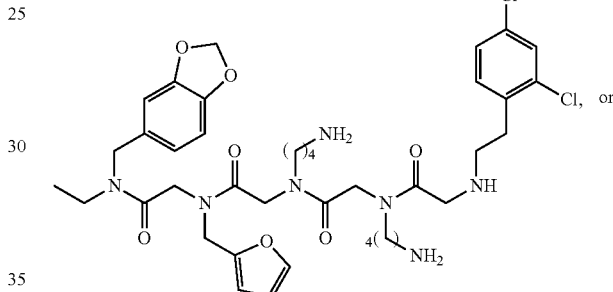
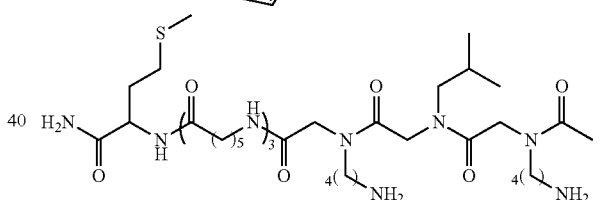
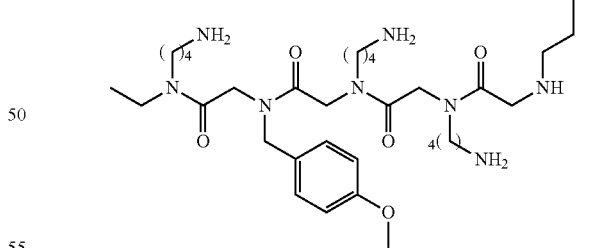

2. The compound of claim 1, wherein said compound is linked through the terminal amide group to a detectable agent, a therapeutic agent, or a scaffold.

3. The compound of claim 1, wherein said compound is modified to contain a sulfhydryl functional group and conjugated to a detectable agent, a therapeutic agent, or a scaffold via a thioether linkage, wherein the detectable agent, therapeutic agent, or scaffold comprise sulfhydryl reactive molecules.

4. The compound of claim 3, wherein the sulfhydryl functional group is from a cysteine.

5. The compound of claim 3, wherein the detectable agent, therapeutic agent, or scaffold is attached via a maleimide.

6. A method of binding a compound to a cancer stem cell (CSC) comprising contacting a composition of claims 1-3 with a CSC.

7. The method of claim 6, wherein the CSC exhibits a phenotype of CD24⁻, CD44+ and/or ALDH+.

8. The method of claim 6, wherein the CSC is a breast CSC.

9. The method of claim 8, wherein the breast CSC is Her2/Neu negative or hormone receptor negative.

10. The method of claim 8, wherein the breast CSC is hormone receptor negative and Her2/Neu negative.

11. A method of identifying a cancer stem cell (CSC) in a subject with breast cancer comprising contacting said subject or a sample from said subject with a compound having the formula:

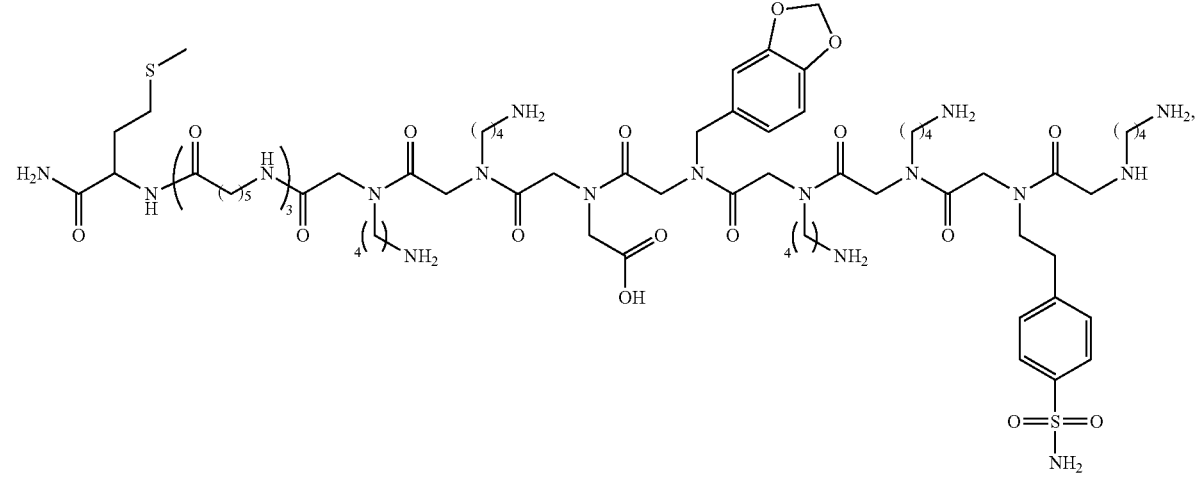

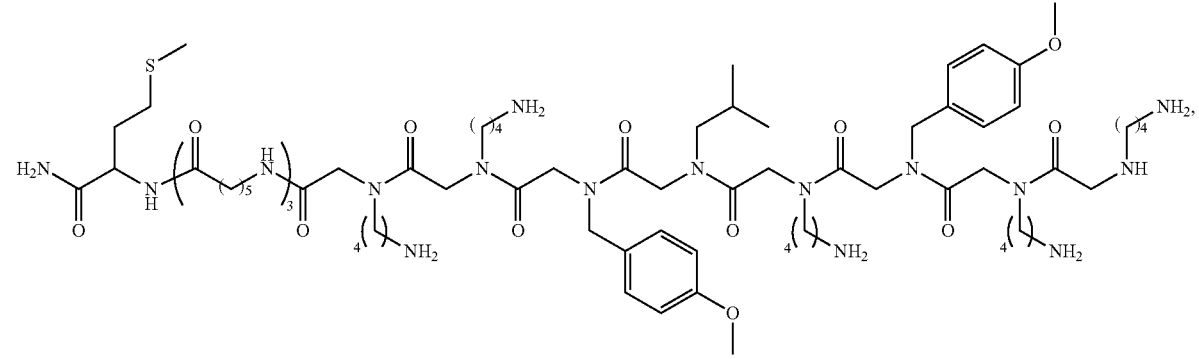

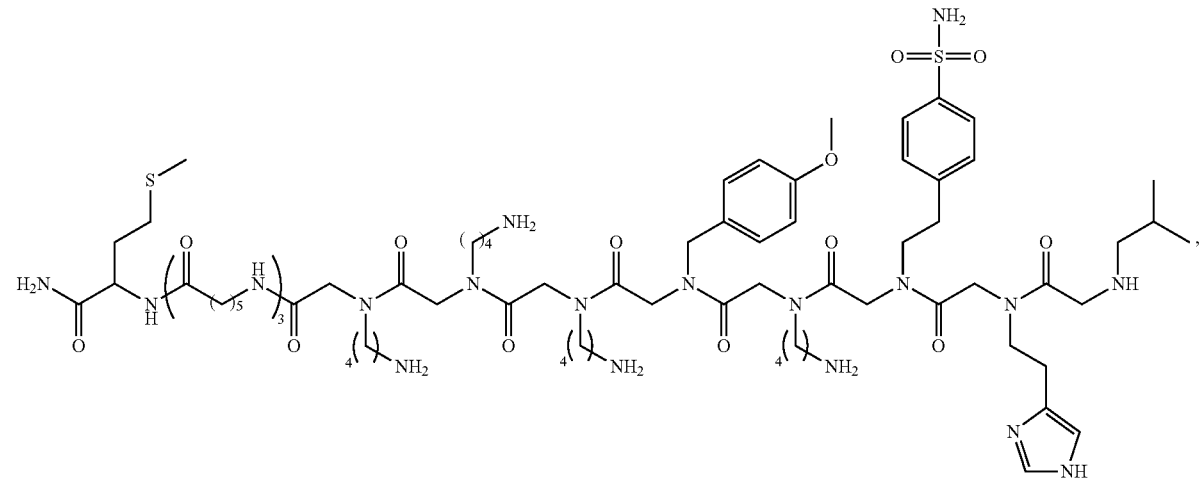

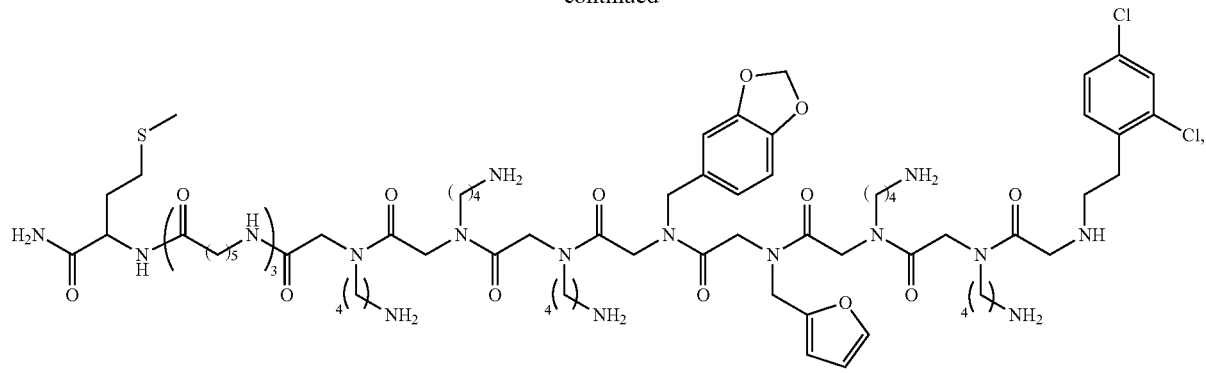
or
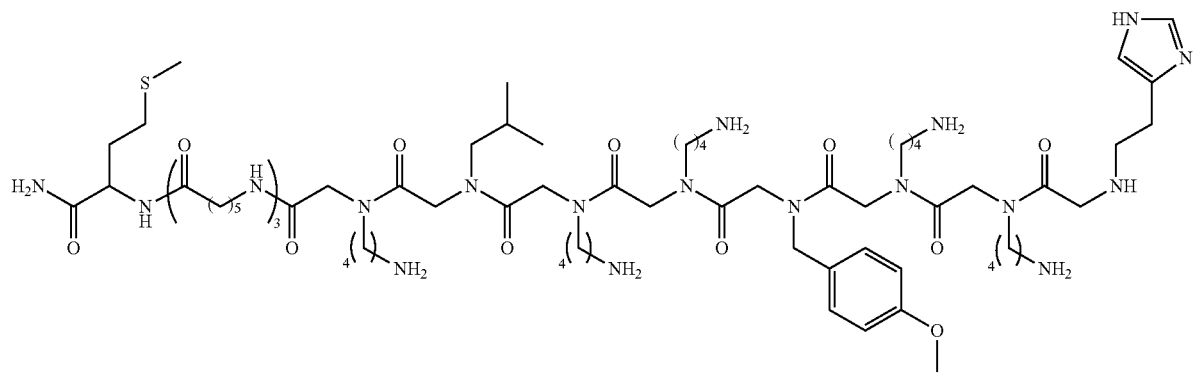
conjugated to a detectable agent.
12. The method of claim 11, further comprising treating said subject for cancer following detection of a CSC.
13. A method of treating a subject with breast cancer comprising contacting said subject with a compound or compounds having the formula:
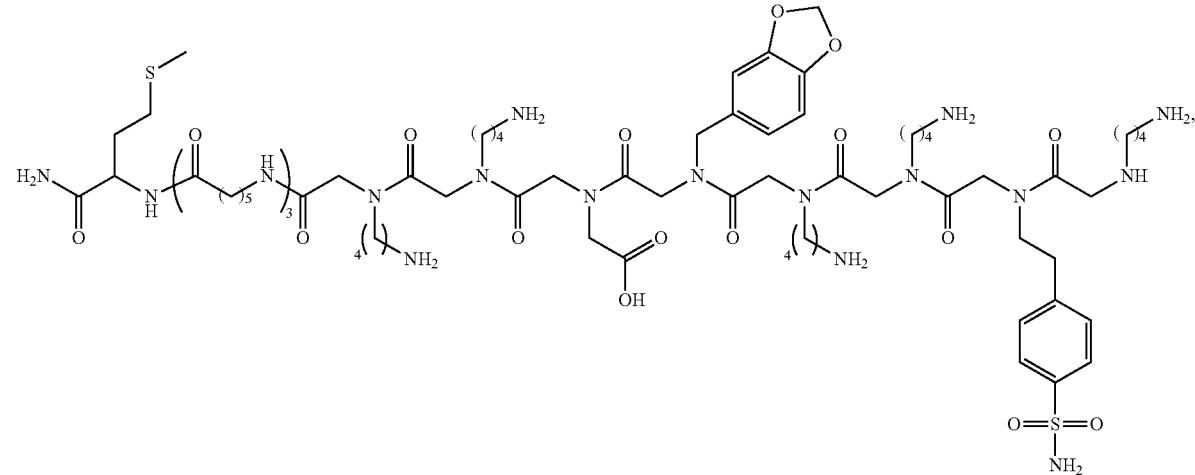

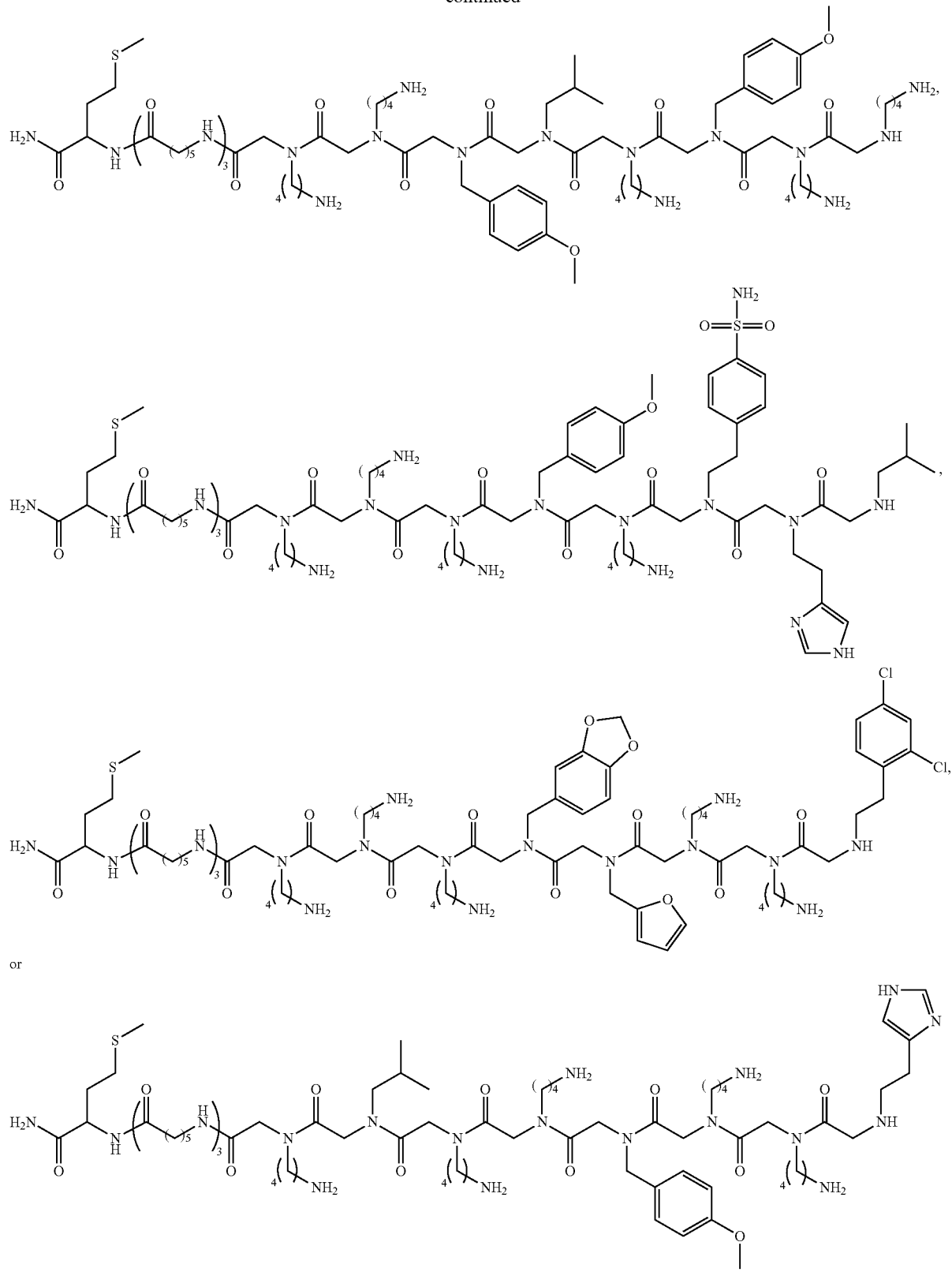
conjugated to a therapeutic agent.
14. The method of claim 13, wherein said breast cancer is primary, recurrent, metastatic or drug resistant.

15. The method of claim 13, wherein said breast cancer is hormone receptor negative.

16. The method of claim 13, wherein the breast cancer is Her2/Neu negative.

17. The method of claim 13, wherein the breast cancer is hormone receptor negative and Her2/Neu negative.

18. The method of claim 13, further comprising treating said subject with a second cancer therapy.

19. The method of claim 18, wherein said second distinct cancer therapy is radiotherapy, chemotherapy, immunotherapy, toxin therapy, hormonal therapy or surgery.

20. The method of claim 13, wherein said therapeutic agent is a radioisotope, chemotherapeutic agent, immunotherapeutic agent, a toxin, or hormonal therapeutic.

21. The method of claim 13, wherein said therapeutic agent is a hyperthermal therapeutic agent.

22. The method of claim 21, wherein the hyperthermal therapeutic agent is a gold nanorod.

23. The method of claim 13, wherein said subject is treated with more than one of said compounds.

24. The method of claim 23, wherein said subject is treated weekly, monthly or chronically.

\* \* \* \* \*